United States Patent [19]

Desrosiers

[11] Patent Number: 5,851,813
[45] Date of Patent: Dec. 22, 1998

[54] PRIMATE LENTIVIRUS ANTIGENIC COMPOSITIONS

[75] Inventor: Ronald C. Desrosiers, Hudson, Mass.

[73] Assignee: President and Fellows of Harvard College, Cambridge, Mass.

[21] Appl. No.: 188,583

[22] Filed: Jan. 27, 1994

Related U.S. Application Data

[63] Continuation-in-part of Ser. No. 727,494, Jul. 9, 1991, abandoned, which is a continuation-in-part of Ser. No. 551,945, Jul. 12, 1990, abandoned.

[51] Int. Cl.$^6$ .............................. C12N 7/00; C12N 7/01; C07K 1/00; A61K 39/12
[52] U.S. Cl. ............................. 435/235.1; 424/199.1; 424/208.1; 530/350; 530/395
[58] Field of Search .......................... 424/199.1, 208.1; 530/350, 395; 435/235.1

[56] References Cited

PUBLICATIONS

Kestler III et al., *Cell*, vol. 65, pp. 651–662, May 17, 1991.
Desrosiers, *Annual Rev. Immunol.*, vol. 8, pp. 557–578, (1990).
Putney et al., *AIDS Vaccine Research and Clinical Trials*, pp. 361–367 (1990).
Zagury et al., *AIDS Research and Human Retroviruses*, vol. 6, No. 9, pp. 1079–1085, Sep. 1990.
Regier et al., *AIDS Research and Human Retroviruses*, vol. 6, No. 11, pp. 1221–1231, (1990).
Hattori et al., *Proc. Natl. Acad. Sci. USA*, vol. 87, pp. 8080–8084, Oct. 1990.
Palca, *Science*, vol. 248, p. 1078.
Cohen et al., *Journal of Virology*, vol. 64, No. 6, pp. 3097–3099, Jun. 1990.
Kestler et al., *Science*, vol. 248, pp. 1109–1112, Jun. 1990.
Lu et al., *Journal of Virology*, vol. 64, No. 10, pp. 5226–5229, Oct. 1990.
Desrosiers, *Nature*, vol. 345, pp. 288–289, May 24, 1990.
Huet et al., *Nature*, vol. 345, pp. 356–359, May 24, 1990.
Koff et al., *AIDS*, vol. 3 (suppl 1), pp. s125–s129, (1989).
Hu et al., *Virology*, vol. 173, pp. 624–630, Dec. 1989.
Trono et al., *Cell*, vol. 59, pp. 113–120, Oct. 6, 1989.
Lu et al., *Journal of Virology*, vol. 63, No. 9, pp. 4115–4119, Sep. 1989.
Desrosiers et al., *Proc. Nat. Acad. Sci. USA*, vol. 86, pp. 6353–6357, Aug. 1989.
Cullen et al., *Cell*, vol. 58, pp. 423–426, Aug. 11, 1989.
Terwilliger et al., *Proc. Natl. Acad. Sci. USA*, vol. 86, pp. 5163–5167, (1989).
Green et al., *Cell*, vol. 58, pp. 215–223, Jul. 14, 1989.
"The Scientific and Social Challenge", *AIDS*, Montreal, Quebec, Canada, p. 219, Jun. 1989.
Guyader et al., *The EMBO Journal*, vol. 8, No. 4, pp. 1169–1175, Apr. 1989.
Fauci et al., *Annals of Internal Medicine*, vol. 110, No. 5, pp. 373–385, Mar. 1, 1989.
Niederman et al., *Proc. Natl. Acad. Sci. USA*, vol. 86, pp. 1128–1132, Feb. 1989.
Malim et al., *Cell*, vol. 58, pp. 205–214, Jul. 14, 1989.
Desrosiers, *Annual Review of Microbiology*, vol. 42, pp. 607–625, (1988).
Naidu et al., *Journal of Virology*, vol. 62, No. 12, pp. 4691–4696, Dec. 1988.
Matthews et al., *Scientific American*, pp. 120–127, Oct. 1988.
Baltimore, *Nature*, vol. 335, pp. 395–396, Sep. 29, 1988.
Ahmad et al., *Science*, vol. 241, pp. 1481–1485, Sep. 16, 1988.
Zagury et al., *Nature*, vol. 332, pp. 728–731, Apr. 21, 1988.
Fauci, *Science*, vol. 329, pp. 617–622, Feb. 5, 1988.
Guy et al., *Nature*, vol. 330, pp. 266–269, Nov. 19, 1987.
Chakrabarti et al., *Nature*, vol. 328, pp. 543–547, Aug. 6, 1987.
Franchini et al., *Nature*, vol. 328, pp. 539–543, Aug. 6, 1987.
Hirsch et al., *Cell*, vol. 49, pp. 307–319, May 8, 1987.
Clavel et al., *The New England Journal of Medicine*, vol. 316, No. 19, pp. 1180–1185, May 7, 1987.
Luciw et al., *Proc. Natl. Acad. Sci, USA*, vol. 84, pp. 1434–1438, Mar. 1987.
Franchini et al., *Virology*, vol. 155, pp. 593–599 (1986).
Terwilliger et al., *Journal of Virology*, vol. 60, No. 2, pp. 754–760, Nov. 1986.
Quinn et al., *Science*, vol. 234, pp. 955–963, Nov. 21, 1986.
Fisher, *Science*, vol. 233, pp. 655–659, Aug. 8, 1986.
Macdonald, *Public Health Reports*, vol. 101, No. 4, pp. 341–348, Jul.–Aug. 1986.
Curran, *Science*, vol. 229, pp. 1352–1357, Sep. 27, 1985.
Crowl et al., *Cell*, vol. 41, pp. 979–986, Jul. 1985.
Daniel et al., *Science*, vol. 228, pp. 1201–1204, Jun. 7, 1985.
Allan et al., *Science*, vol. 228, pp. 1091–1093, May 31, 1985.
Barin et al., *Science*, vol. 228, pp. 1094–1096, May 31, 1985.
Robey et al., *Science*, vol. 228, pp. 593–595, May 3, 1985.
Muesing et al., *Nature*, vol. 313, pp. 450–458, Feb. 7, 1985.
Ratner et al., *Nature*, vol. 313, pp. 277–284, Jan. 24, 1985.
Wain–Hobson et al., *Cell*, vol. 40, pp. 9–17, Jan. 1985.
Shaw et al., *Science*, vol. 226, pp. 1165–1171, Dec. 7, 1984.
Hahn et al., *Nature*, vol. 312, pp. 166–169, Nov. 8, 1984.
Sarngadharan et al., *Science*, vol. 224, No. 4648, pp. 506–508, May 4, 1984.
Schupbach et al., *Science*, vol. 224, pp. 503–505, May 4, 1984.

(List continued on next page.)

*Primary Examiner*—Lynette F. Smith
*Attorney, Agent, or Firm*—Fish & Richardson P. C.

[57] ABSTRACT

Molecular clones of primate lentiviruses that harbor an engineered non-revertible null mutation in the nef gene and which may further include a non-revertible null mutation in one or more non-essential genetic elements, vif, vpr, vpx, vpu, Negative Regulatory Element, nuclear factor κB-binding element, or Sp1 binding element sequences are disclosed. Intact viruses containing such mutant genomes are also disclosed. These infectious, nonpathogenic viruses are capable of eliciting a protective host immune response and, thus, are useful as a vaccine that protects against AIDS in human subjects.

33 Claims, 60 Drawing Sheets

OTHER PUBLICATIONS

Gallo et al, *Science*, vol. 224, pp. 500–503, May 4, 1984.

Essex et al., *Science*, vol. 220, pp. 859–862, May 20, 1983.

Chermann et al., *Science*, vol. 220, pp. 868–871, May 20, 1983.

Haynes, 1993, "Scientific and Social Issues of Human . . ." Science 260: 1279–1286.

Fast, et al., 1994, "Efficacy trials of AIDS vaccines: how science . . ." Current Biology 691–697.

Brown, 1993, "AIDS vaccine trials viewed . . . " The Washington Post Newspaper, Jun. 10, 1993.

Greene, 1993, "AIDS and the immune system . . ." Scientific American, Sep. 1993, pp. 99–105.

Shibata et al., 1990, "Mutational analysis of . . ." J. Virol. 64(2): 742–747.

FIG. 1
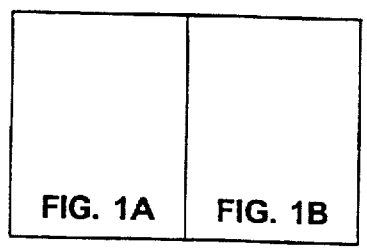
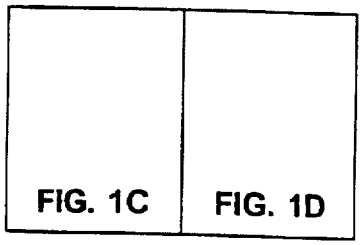
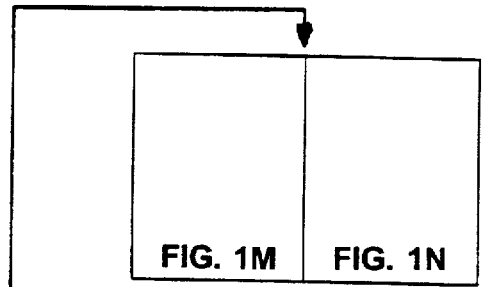
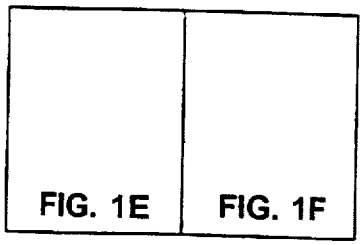
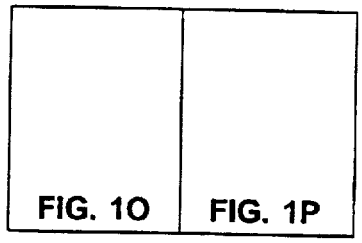
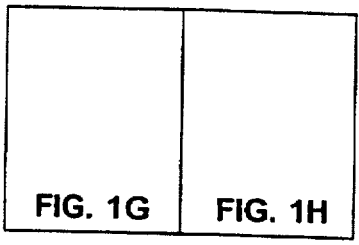
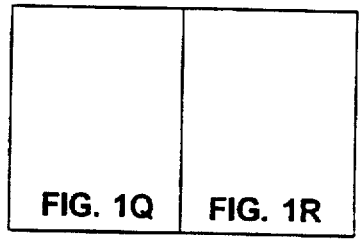
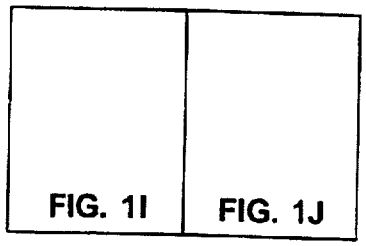
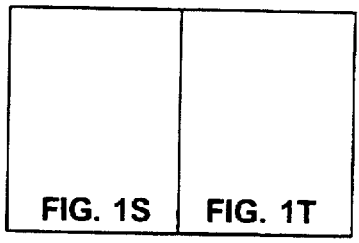
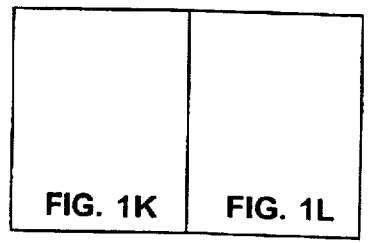
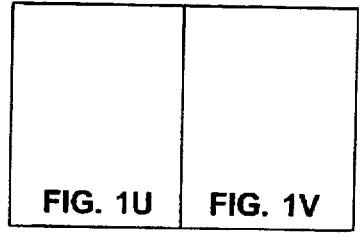

```
           10        20        30        40        50
TGGAAGGGATTTATTACAGTGCAAGAAGACATAGAATCTTAGACATATACT
U3->
           110       120       130       140       150
ACCAGGAATTAGATACCCAAAGACATTTGGCTGGCTATGGAAATTAGTCCC 210       220       230       240       250
CATCCAGCTCAAACTTCCCAGTGGGATGACCCTTGGGGAGAGGTTCTAGCA 310       320       330       340       350
ACCCAGAAGAGTTTGGAAGCAAGTCAGGCCTGTCAGAGGAAGAGGTTAGAA 410       420       430       440       450
TCGCTGAAACAGCAGGGACTTTCCACAAGGGGATGTTACGGGGAGGTACT
                NF Kappa B         Sp1         Sp1

510       520       530       540       550
GCATTTCGCTCTGTATTCAGTCGCTCTGCGGAGAGGCTGGCAGATTGAGC
R->

610       620       630       640       650
TAGACTCTCACCAGCACTTGGCCGGTGCTGGGCAGAGTGACTCCACGCTT
U5->

710       720       730       740       750
TGTGTGTTCCCATCTCTCCTAGCCGCCGCCTGGTCAACTCGGTACTCAAT 810       820       830       840       850
GCAGGAAAATCCCTAGCAGATTGGCGCCTGAACAGGGACTTGAAGGAGAG
                       ᴸRNA primer binding site 910       920       930       940       950
CAACCACGACGGAGTGCTCCTATAAAGGCGCGGGTCGGTACCAGACGGCG 1010      1020      1030      1040
AAAGAAATAGCTGTCTTTTATCCAGGAAGGGGTAATAAGATAGAG
```

FIG. 1A

```
             60         70        80        90       100
      TAGAAAAGGAAGAAGGCATCATACCAGATTGGCAGGATTACACCTCAGG 160        170       180       190       200
      TGTAAATGTATCAGATGAGGCACAGGAGGATGAGGAGCATTATTTAATG 260        270       280       290       300
      TGGAAGTTTGATCCAACTCTGGCCTACACTTATGAGGCATATGTTAGAT 360        370       380       390       400
      .GAAGGCTAACCGCAAGAGGCCTTCTTAACATGGCTGACAAGAAGGAAAC 460        470       480       490       500
      .GGGGAGGAGCCGGTCGGGAACGCCCACTTTCTTGATGTATAAATATCACT
         Sp1          Sp1                      TATA 560        570       580       590       600
      CCTGGGAGGTTCTCTCCAGCACTAGCAGGTAGAGCCTGGGTGTTCCCTGC 660        670       680       690       700
      GCTTGCTTAAAGCCCTCTTCAATAAAGCTGCCATTTTAGAAGTAAGCTAG 760        770       780       790       800
      .AATAAGAAGACCCTGGTCTGTTAGGACCCTTTCTGCTTTGGGAAACCGAA 860        870       880       890       900
      TGAGAGACTCCTGAGTACGGCTGAGTGAAGGCAGTAAGGGCGGCAGGAAC 960        970       980       990      1000
      TGAGGAGCGGGAGAGGAAGAGGCCTCCGGTTGCAGGTAAGTGCAACACAA 1050       1060       1070      1080      1090      1100
TGGGAGATGGGCGTGAGAAACTCCGTCTTGTCAGGGAAGAAAGCAGATGAATTA
gag-> MetGlyValArgAsnSerValLeuSerGlyLysLysAlaAspGluLeu
```

FIG. 1B

```
        1110      1120      1130      1140      1150
GAAAAAATTAGGCTACGACCCAACGGAAAGAAAAAGTACATGTTGAAGCATG
GluLysIleArgLeuArgProAsnGlyLysLysLysTyrMetLeuLysHis 1210      1220      1230      1240      1250
TGTTGGAGAACAAAGAAGGATGTCAAAAATACTTTCGGTCTTAGCTCCAT
euLeuGluAsnLysGluGlyCysGlnLysIleLeuSerValLeuAlaPro 1310      1320      1330      1340      1350
CGTCATCTGGTGCATTCACGCAGAAGAGAAAGTGAAACACACTGAGGAAGCA
sValIleTrpCysIleHisAlaGluGluLysValLysHisThrGluGluAla 1410      1420      1430      1440      1450
ACTATGCCAAAAACAAGTAGACCAACAGCACCATCTAGCGGCAGAGGAGGA
ThrMetProLysThrSerArgProThrAlaProSerSerGlyArgGlyGly 1510      1520      1530      1540      1550
GCCCGAGAACATTAAATGCCTGGGTAAAATTGATAGAGGAAAAGAAATTTG
erProArgThrLeuAsnAlaTrpValLysLeuIleGluGluLysLysPhe 1610      1620      1630      1640      1650
CTATGACATTAATCAGATGTTAAATTGTGTGGGAGACCATCAAGCGGCTATG
oTyrAspIleAsnGlnMetLeuAsnCysValGlyAspHisGlnAlaAlaMet 1710      1720      1730      1740      1750
CAGCACCCACAACCAGCTCCACAACAAGGACAACTTAGGGAGCCGTCAGGA
GlnHisProGlnProAlaProGlnGlnGlyGlnLeuArgGluProSerGly 1810      1820      1830      1840      1850
TGTACAGACAACAGAACCCCATACCAGTAGGCAACATTTACAGGAGATGG
etTyrArgGlnGlnAsnProIleProValGlyAsnIleTyrArgArgTrp 1910      1920      1930      1940      1950
TCTAGATGTAAAACAAGGGCCAAAAGAGCCATTTCAGAGCTATGTAGACAGG
eLeuAspValLysGlnGlyProLysGluProPheGlnSerTyrValAspArg 2010      2020      2030      2040      2050
TGGATGACTCAAACACTGCTGATTCAAAATGCTAACCCAGATTGCAAGCTA
TrpMetThrGlnThrLeuLeuIleGlnAsnAlaAsnProAspCysLysLeu
```

FIG. 1C

```
            1160      1170      1180      1190      1200
       TAGTATGGGCAGCAAATGAATTAGATAGATTTGGATTAGCAGAAAGCC
        ValValTrpAlaAlaAsnGluLeuAspArgPheGlyLeuAlaGluSerL 1260      1270      1280      1290      1300
       TAGTGCCAACAGGCTCAGAAAATTTAAAAGCCTTTATAATACTGTCTG
        LeuValProThrGlySerGluAsnLeuLysSerLeuTyrAsnThrValCy 1360      1370      1380      1390      1400
       AAACAGATAGTGCAGAGACACCTAGTGGTGGAAACAGGAACAACAGAA
        LysGlnIleValGlnArgHisLeuValValGluThrGlyThrThrGlu 1460      1470      1480      1490      1500
       AATTACCCAGTACAACAAATAGGTGGTAACTATGTCCACCTGCCATTAA
        AsnTyrProValGlnGlnIleGlyGlyAsnTyrValHisLeuProLeuS 1560      1570      1580      1590      1600
      GAGCAGAAGTAGTGCCAGGATTTCAGGCACTGTCAGAAGGTTGCACCCC
       GlyAlaGluValValProGlyPheGlnAlaLeuSerGluGlyCysThrPr 1660      1670      1680      1690      1700
       CAGATTATCAGAGATATTATAAACGAGGAGGCTGCAGATTGGGACTTG
        GlnIleIleArgAspIleIleAsnGluGluAlaAlaAspTrpAspLeu 1760      1770      1780      1790      1800
       TCAGATATTGCAGGAACAACTAGTTCAGTAGATGAACAAATCCAGTGGA
        SerAspIleAlaGlyThrThrSerSerValAspGluGlnIleGlnTrpM 1860      1870      1880      1890      1900
       ATCCAACTGGGGTTGCAAAAATGTGTCAGAATGTATAACCCAACAAACAT
        IleGlnLeuGlyLeuGlnLysCysValArgMetTyrAsnProThrAsnIl 1960      1970      1980      1990      2000
       TTCTACAAAAGTTTAAGAGCAGAACAGACAGATGCAGCAGTAAAGAAT
        PheTyrLysSerLeuArgAlaGluGlnThrAspAlaAlaValLysAsn 2060      2070      2080      2090      2100
       GTGCTGAAGGGGCTGGGTGTGAATCCCACCCTAGAAGAAATGCTGACGG
        ValLeuLysGlyLeuGlyValAsnProThrLeuGluGluMetLeuThrA
```

FIG. 1D

```
           2110        2120        2130        2140        2150
        CTTGTCAAGGAGTAGGGGGGCCGGGACAGAAGGCTAGATTAATGGCAGAA
        laCysGlnGlyValGlyGlyProGlyGlnLysAlaArgLeuMetAlaGlu 2210        2220        2230        2240        2250
        ACAGAGGGGACCAAGAAAGCCAATTAAGTGTTGGAATTGTGGGAAAGAGGGA
        nGlnArgGlyProArGlysProIleLysCysTrpAsnCysGlyLysGluGly
                        pol-> ValLeuGluLeuTrpGluArgGly 2310        2320        2330        2340        2350
        TGTGGAAAAATGGACCATGTTATGGCCAAATGCCCAGACAGACAGGCGGGT
        CysGlyLysMetAspHisValMetAlaLysCysProAspArgGlnAlaGly
        etTrpLysAsnGlyProCysTyrGlyGlnMetProArgGlnThrGlyGly 2410        2420        2430        2440        2450
        CTCAAGTGCATCAGGGGCTGATGCCAACTGCTCCCCCAGAGGACCCAGCT
        laGlnValHisGlnGlyLeuMetProThrAlaProProGluAspProAla
        ySerSerAlaSerGlyAlaAspAlaAsnCysSerProArgGlyProSer 2510        2520        2530        2540        2550
        GCAGAGAGAAAGCAGAGAGAAGCCTTACAAGGAGGTGACAGAGGATTTGCTG
        sGlnArgGluSerArgGluLysProTyrLysGluValThrGluAspLeuLeu
        AlaGluArGlysGlnArgGluAlaLeuGlnGlyGlyAspArgGlyPheAla 2610        2620        2630        2640        2650
        AAGGACAGCCTGTAGAAGTATTACTGGATACAGGGGCTGATGATTCTATT
        luGlyGlnProValGluValLeuLeuAspThrGlyAlaAspAspSerIle 2710        2720        2730        2740        2750
        AATAGGAGGTTTTATTAATACTAAAGAATACAAAAATGTAGAAATAGAAGTT
        yIleGlyGlyPheIleAsnThrLysGluTyrLysAsnValGluIleGluVal 2810        2820        2830        2840        2850
        AACATTTTTGGTAGAAATTTGCTAACAGCTCTGGGGATGTCTCTAAATTTT
        AsnIlePheGlyArgAsnLeuLeuThrAlaLeuGlyMetSerLeuAsnPhe 2910        2920        2930        2940        2950
        ATGGACCAAAATTGAAGCAGTGGCCATTATCAAAAGAAAAGATAGTTGCA
        spGlyProLysLeuLysGlnTrpProLeuSerLysGluLysIleValAla
```

FIG. 1E

```
              2160      2170      2180      2190      2200
       GCCCTGAAAGAGGCCCTCGCACCAGTGCCAATCCCTTTTGCAGCAGCCCA
       AlaLeuLysGluAlaLeuAlaProValProIleProPheAlaAlaAlaGl 2260      2270      2280      2290      2300
       CACTCTGCAAGGCAATGCAGAGCCCCAAGAAGACAGGGATGCTGGAAA
         HisSerAlaArgGlnCysArgAlaProArgArgGlnGlyCysTrpLys
        ThrLeuCysLysAlaMetGlnSerProLysLysThrGlyMetLeuGluM 2360      2370      2380      2390      2400
       TTTTTAGGCCTTGGTCCATGGGGAAAGAAGCCCCGCAATTTCCCCATGG
        PheLeuGlyLeuGlyProTrpGlyLysLysProArgAsnPheProMetA
        PhePheArgProTrpSerMetGlyLysGluAlaProGlnPheProHisGl 2460      2470      2480      2490      2500
       GTGGATCTGCTAAAGAACTACATGCAGTTGGGCAAGCAGCAGAGAGAAAA
       ValAspLeuLeuLysAsnTyrMetGlnLeuGlyLysGlnGlnArgGluLy
        CysGlySerAlaLysGluLeuHisAlaValGlnAlaAlaGluArGlys 2560      2570      2580      2590      2600
        CACCTCAATTCTCTCTTTGGAGGAGACCAGTAGTCACTGCTCATATTG
         HisLeuAsnSerLeuPheGlyGlyAspGlnEnd
         AlaProGlnPheSerLeuTrpArgArgProValValThrAlaHisIleG 2660      2670      2680      2690      2700
       GTAACAGGAATAGAGTTAGGTCCACATTATACCCCAAAAATAGTAGGAGG
       ValThrGlyIleGluLeuGlyProHisTyrThrProLysIleValGlyGl 2760      2770      2780      2790      2800
        TTAGGCAAAAGGATTAAAGGGACAATCATGACAGGGGACACCCCGATT
        LeuGlyLysArgIleLysGlyThrIleMetThrGlyAspThrProIle 2860      2870      2880      2890      2900
       CCCATAGCTAAAGTAGAGCCTGTAAAAGTCGCCTTAAAGCCAGGAAAGG
        ProIleAlaLysValGluProValLysValAlaLeuLysProGlyLysA 2960      2970      2980      2990      3000
       TTAAGAGAAATCTGTGAAAAGATGGAAAAGGATGGTCAGTTGGAGGAAGC
       LeuArgGluIleCysGluLysMetGluLysAspGlyGlnLeuGluGluAl
```

FIG. 1F

```
         3010      3020      3030      3040      3050
TCCCCCGACCAATCCATACAACACCCCACATTTGCTATAAAGAAAAGGAT
aProProThrAsnProTyrAsnThrProThrPheAlaIleLysLysLysAsp 3110      3120      3130      3140      3150
ACTCAGGACTTTACGGAAGTCCAATTAGGAATACCACACCCTGCAGGACTA
ThrGlnAspPheThrGluValGlnLeuGlyIleProHisProAlaGlyLeu 3210      3220      3230      3240      3250
CCATACCTCTAGATGAAGAATTTAGGCAGTACACTGCCTTTACTTTACCA
erIleProLeuAspGluGluPheArgGlnTyrThrAlaPheThrLeuPro 3310      3320      3330      3340      3350
TCAGGGATGGAAGGGGTCACCAGCCATCTTCCAATACACTATGAGACATGTG
oGlnGlyTrpLysGlySerProAlaIlePheGlnTyrThrMetArgHisVal 3410      3420      3430      3440      3450
ATGGATGACATCTTAATAGCTAGTGACAGGACAGACCTGGAACATGACAGG
MetAspAspIleLeuIleAlaSerAspArgThrAspLeuGluHisAspArg 3510      3520      3530      3540      3550
CAGAAGAGAAATTCCAAAAGATCCCCCATTTCAATGGATGGGGTACGAA
roGluGluLysPheGlnLysAspProProPheGlnTrpMetGlyTyrGlu 3610      3620      3630      3640      3650
GACCTGGACAGTGAATGATATACAGAAGTTAGTAGGAGTATTAAATTGGCA
uThrTrpThrValAsnAspIleGlnLysLeuValGlyValLeuAsnTrpAla 3710      3720      3730      3740      3750
AGAGGAAAAATGACTCTAACAGAGGAAGTTCAGTGGACTGAGATGGCAGAA
ArgGlyLysMetThrLeuThrGluGluValGlnTrpThrGluMetAlaGlu 3810      3820      3830      3840      3850
GTTATTACCAAGAAGGCAAGCCATTAGAAGCCACGGTAATAAAGAGTCAG
ysTyrTyrGlnGluGlyLysProLeuGluAlaThrValIleLysSerGln 3910      3920      3930      3940      3950
AGGAAAATTTGCAAAGATAAAGAATACACATACCAATGGAGTGAGACTATTA
lGlyLysPheAlaLysIleLysAsnThrHisThrAsnGlyValArgLeuLeu
```

FIG. 1G

```
         3060      3070      3080      3090      3100
      AAGAACAAATGGAGAATGCTGATAGATTTTAGGGAACTAAATAGGGTC
      LysAsnLysTrpArgMetLeuIleAspPheArgGluLeuAsnArgVal 3160      3170      3180      3190      3200
      GCAAAAGGAAAAGAATTACAGTACTGGATATAGGTGATGCATATTTCT
      AlaLysArGlysArgIleThrValLeuAspIleGlyAspAlaTyrPheS 3260      3270      3280      3290      3300
      TCAGTAAATAATGCAGAGCCAGGAAAACGATACATTTATAAGGTTCTGCC
      SerValAsnAsnAlaGluProGlyLysArgTyrIleTyrLysValLeuPr 3360      3370      3380      3390      3400
      CTAGAACCCTTCAGGAAGGCAAATCCAGATGTGACCTTAGTCCAGTAT
      LeuGluProPheArGlysAlaAsnProAspValThrLeuValGlnTyr 3460      3470      3480      3490      3500
      GTAGTTTTACAGTCAAAGGAACTCTTGAATAGCATAGGGTTTTCTACCC
      ValValLeuGlnSerLysGluLeuLeuAsnSerIleGlyPheSerThrP 3560      3570      3580      3590      3600
      TTGTGGCCAACAAAATGGAAGTTGCAAAGATAGAGTTGCCACAAAGAGA
      LeuTrpProThrLysTrpLysLeuGlnLysIleGluLeuProGlnArgGl 3660      3670      3680      3690      3700
      GCTCAAATTTATCCAGGTATAAAAACCAAACATCTCTGTAGGTTAATT
      AlaGlnIleTyrProGlyIleLysThrLysHisLeuCysArgLeuIle 3760      3770      3780      3790      3800
      GCAGAATATGAGGAAAATAAAATAATTCTCAGTCAGGAACAAGAAGGAT
      AlaGluTyrGluGluAsnLysIleIleLeuSerGlnGluGlnGluGlyC 3860      3870      3880      3890      3900
      GACAATCAGTGGTCTTATAAAATTCACCAAGAAGACAAAATACTGAAAGT
      AspAsnGlnTrpSerTyrLysIleHisGlnGluAspLysIleLeuLysVa 3960      3970      3980      3990      4000
      GCACATGTAATACAGAAAATAGGAAAGGAAGCAATAGTGATCTGGGGA
      AlaHisValIleGlnLysIleGlyLysGluAlaIleValIleTrpGly
```

FIG. 1H

```
       4010      4020      4030      4040      4050
CAGGTCCCAAAATTCCACTTACCAGTTGAGAAGGATGTATGGGAACAGTGG
GlnValProLysPheHisLeuProValGluLysAspValTrpGluGlnTrp 4110      4120      4130      4140      4150
CAACACCACCGCTAGTAAGATTAGTCTTCAATCTAGTGAAGGACCCTATA
erThrProProLeuValArgLeuValPheAsnLeuValLysAspProIle 4210      4220      4230      4240      4250
AGAAGGGAAAGCAGGATATATCACAGATAGGGGCAAAGACAAAGTAAAAGTG
sGluGlyLysAlaGlyTyrIleThrAspArgGlyLysAspLysValLysVal 4310      4320      4330      4340      4350
GCATTGACAGACTCAGGGCCAAAGGCAAATATTATAGTAGATTCACAATAT
AlaLeuThrAspSerGlyProLysAlaAsnIleIleValAspSerGlnTyr 4410      4420      4430      4440      4450
TTAATCAAATAATAGAAGAAATGATTAAAAAGTCAGAAATTTATGTAGCA
aAsnGlnIleIleGluGluMetIleLysLysSerGluIleTyrValAla 4510      4520      4530      4540      4550
AGTTAGTCAAGGGATTAGACAAGTTCTCTTCTTGGAAAAGATAGAGCCAGCA
uValSerGlnGlyIleArgGlnValLeuPheLeuGluLysIleGluProAla 4610      4620      4630      4640      4650
AAATTTGGATTACCCAGAATAGTGGCCAGACAGATAGTAGACACCTGTGAT
LysPheGlyLeuProArgIleValAlaArgGlnIleValAspThrCysAsp 4710      4720      4730      4740      4750
TAGGGACTTGGCAAATGGATTGTACCCATCTAGAGGGAAAAATAATCATA
euGlyThrTrpGlnMetAspCysThrHisLeuGluGlyLysIleIleIle 4810      4820      4830      4840      4850
AGAGACAGGAAGACAGACAGCACTATTTCTGTTAAAATTGGCAGGCAGATGG
nGluThrGlyArgGlnThrAlaLeuPheLeuLeuLysLeuAlaGlyArgTrp 4910      4920      4930      4940      4950
GAAGTAAAGATGGTTGCATGGTGGGCAGGGATAGAGCACACCTTTGGGGTA
GluValLysMetValAlaTrpTrpAlaGlyIleGluHisThrPheGlyVal
```

FIG. 1I

```
     4060      4070      4080      4090      4100
TGGACAGACTATTGGCAGGTAACCTGGATACCGGAATGGGATTTTATCT
TrpThrAspTyrTrpGlnValThrTrpIleProGluTrpAspPheIleS 4160      4170      4180      4190      4200
GAGGGAGAAGAAACCTATTATACAGATGGATCATGTAATAAACAGTCAAA
GluGlyGluGluThrTyrTyrThrAspGlySerCysAsnLysGlnSerLy 4260      4270      4280      4290      4300
TTAGAACAGACTACTAATCAACAAGCAGAATTGGAAGCATTTCTCATG
LeuGluGlnThrThrAsnGlnGlnAlaGluLeuGluAlaPheLeuMet 4360      4370      4380      4390      4400
GTTATGGGAATAATAACAGGATGCCCTACAGAATCAGAGAGCAGGCTAG
ValMetGlyIleIleThrGlyCysProThrGluSerGluSerArgLeuV 4460      4470      4480      4490      4500
TGGGTACCAGCACACAAAGGTATAGGAGGAAACCAAGAAATAGACCACCT
TrpValProAlaHisLysGlyIleGlyGlyAsnGlnGluIleAspHisLe 4560      4570      4580      4590      4600
CAAGAAGAACATGATAAATACCATAGTAATGTAAAAGAATTGGTATTC
GlnGluGluHisAspLysTyrHisSerAsnValLysGluLeuValPhe 4660      4670      4680      4690      4700
AAATGTCATCAGAAAGGAGAGGCTATACATGGGCAGGCAAATTCAGATC
LysCysHisGlnLysGlyGluAlaIleHisGlyGlnAlaAsnSerAspL 4760      4770      4780      4790      4800
GTTGCAGTACATGTAGCTAGTGGATTCATAGAAGCAGAGGTAATTCCACA
ValAlaValHisValAlaSerGlyPheIleGluAlaGluValIleProG 4860      4870      4880      4890      4900
CCTATTACACATCTACACACAGATAATGGTGCTAACTTTGCTTCGCAA
ProIleThrHisLeuHisThrAspAsnGlyAlaAsnPheAlaSerGln 4960      4970      4980      4990      5000
CCATACAATCCACAGAGTCAGGGAGTAGTGGAAGCAATGAATCACCACC
ProTyrAsnProGlnSerGlnGlyValValGluAlaMetAsnHisHisL
```

FIG. 1J

```
          5010       5020       5030       5040       5050
       TGAAAAATCAAATAGATAGAATCAGGGAACAAGCAAATTCAGTAGAAACCATA
       euLysAsnGlnIleAspArgIleArgGluGlnAlaAsnSerValGluThrIle 5110       5120       5130       5140       5150
       AGGGGATATGACTCCAGCAGAAAGATTAATTAACATGATCACTACAGAACAA
       eGlyAspMetThrProAlaGluArgLeuIleAsnMetIleThrThrGluGln 5210       5220       5230       5240       5250
       GTCTATTACAGAGAAGGCAGAGATCAACTGTGGAAGGGACCCGGTGAGCTA
       ValTyrTyrArgGluGlyArgAspGlnLeuTrpLysGlyProGlyGluLeu 5310       5320       5330       5340       5350
       AGGTAGTACCCAGAAGAAAGGCTAAAATTATCAAAGATTATGGAGGAGGAA
       ysValValProArgArGlysAlaLysIleIleLysAspTyrGlyGlyGly
                                         vlf-> MetGluGluGlu 5410       5420       5430       5440       5450
       GGTGGCATAGCCTCATAAAATATCTGAAATATAAAACTAAAGATCTACAAA
       uValAlaEnd
       rgTrpHisSerLeuIleLysTyrLeuLysTyrLysThrLysAspLeuGln 5510       5520       5530       5540       5550
       CAGCAGAGTAATCTTCCCACTACAGGAAGGAAGCCATTTAGAAGTACAAGGG
       sSerArgValIlePheProLeuGlnGluGlySerHisLeuGluValGlnGly 5610       5620       5630       5640       5650
       AGGATAACCTGGTACTCAAAGAACTTTTGGACAGATGTAACACCAAACTAT
       ArgIleThrTrpTyrSerLysAsnPheTrpThrAspValThrProAsnTyr 5710       5720       5730       5740       5750
       AAGTGAGAAGGGCCATCAGGGGAGAACAACTGCTGTCTTGCTGCAGGTTC
       luValArgArgAlaIleArgGlyGluGlnLeuLeuSerCysCysArgPhe 5810       5820       5830       5840       5850
       AGTAGTAAGCGATGTCAGATCCCAGGGAGAGAATCCCACCTGGAAACAGTGG
       sValValSerAspValArgSerGlnGlyGluAsnProThrTrpLysGlnTrp
              vpx-> MetSerAspProArgGluArgIleProProGlyAsnSer
```

FIG. 1K

```
       5060      5070      5080      5090      5100
   GTATTAATGGCAGTTCATTGCATGAATTTTAAAAGAAGGGGAGGAAT
   ValLeuMetAlaValHisCysMetAsnPheLysArgArgGlyGlyIl 5160      5170      5180      5190      5200
   GAGATACAATTTCAACAATCAAAAACTCAAAATTTAAAAATTTTCGG
   GluIleGlnPheGlnGlnSerLysAsnSerLysPheLysAsnPheArg 5260      5270      5280      5290      5300
   TTGTGGAAAGGGGAAGGAGCAGTCATCTTAAAGGTAGGGACAGACATTA
   LeuTrpLysGlyGluGlyAlaValIleLeuLysValGlyThrAspIleL 5360      5370      5380      5390      5400
   AAGAGGTGGATAGCAGTTCCCACATGGAGGATACCGGAGAGGCTAGAGA
   LysGluValAspSerSerSerHisMetGluAspThrGlyGluAlaArgI
   LysArgTrpIleAlaValProThrTrpArgIleProGluArgLeuGluA 5460      5470      5480      5490      5500
   AGGTTTGCTATGTGCCCCATTTTAAGGTCGGATGGGCATGGTGGACCTG

LysValCysTyrValProHisPheLysValGlyTrpAlaTrpTrpThrCy 5560      5570      5580      5590      5600
   TATTGGCATTTGACACCAGAAAAAGGGTGGCTCAGTACTTATGCAGTG
   TyrTrpHisLeuThrProGluLysGlyTrpLeuSerThrTyrAlaVal 5660      5670      5680      5690      5700
   GCAGACATTTTACTGCATAGCACTTATTTCCCTTGCTTTACAGCGGGAG
   AlaAspIleLeuLeuHisSerThrTyrPheProCysPheThrAlaGlyG 5860      5770      5780      5790      5800
   CCGAGAGCTCATAAGTACCAGGTACCAAGCCTACAGTACTTAGCACTGAA
   ProArgAlaHisLysTyrGlnValProSerLeuGlnTyrLeuAlaLeuLy 5860      5870      5880      5890      5900
   AGAAGAGACAATAGGAGAGGCCTTCGAATGGCTAAACAGAACAGTAGA
   ArgArgAspAsnArgArgGlyLeuArgMetAlaLysGlnAsnSerArg
   GlyGluGluThrIleGlyGluAlaPheGluTrpLeuAsnArgThrValGl
```

FIG. 1L

```
         5910      5920      5930      5940      5950
    GGAGATAAACAGAGAGGCGGTAAACCACCTACCAAGGGAGCTAATTTTCCA
    GlyAspLysGlnArgGlyGlyLysProProThrLysGlyAlaAsnPhePro
   uGluIleAsnArgGluAlaValAsnHisLeuProArgGluLeuIlePheGln 6010      6020      6030      6040      6050
    CCAAGCTATGTAAAATACAGATACTTGTGTTTAATACAAAAGGCTTTATTTA
    ProSerTyrValLysTyrArgTyrLeuCysLeuIleGlnLysAlaLeuPhe 6110      6120      6130      6140      6150
    GGGGATGGAGACCAGGACCTCCTCCTCCTCCCCCTCCAGGACTAGCATAA
    lyGlyTrpArgProGlyProProProProProProGlyLeuAlaEnd
                                                  vpr->

6210      6220      6230      6240      6250
    TGAATGGGTAGTGGAGGTTCTGGAAGAACTGAAAGAAGAAGCTTTAAAACA.
   pGluTrpValValGluValLeuGluGluLeuLysGluGluAlaLeuLysHis 6310      6320      6330      6340      6350
    CATGGAGACACCCTTGAGGGAGCAGGAGAACTCATTAGAATCCTCCAACGA
    HisGlyAspThrLeuGluGlyAlaGlyGluLeuIleArgIleLeuGlnArg
     MetGluThrProLeuArgGluGlnGluAsnSerLeuGluSerSerAsnGlu 6410      6420      6430      6440      6450
    AACCTGGGGGAGGAAATCCTCTCTCAGCTATACCGCCCTCTAGAAGCATG
    lnProGlyGlyGlyAsnProLeuSerAlaIleProProSerArgSerMet
    AsnLeuGlyGluGluIleLeuSerGlnLeuTyrArgProLeuGluAlaCys 6510      6520      6530      6540      6550
    TTCTTAAAAAAGGCTTGGGGATATGTTATGAGCAATCACGAAAGAGAAGA
    heLeuLysLysGlyLeuGlyIleCysTyrGluGlnSerArglysArgArg
                           rev-> MetSerAsnHisGluArgGluGlu 6610      6620      6630      6640      6650
    AGTATGGGATGTCTTGGGAATCAGCTGCTTATCGCCATCTTGCTTTTAAG
    MetGlyCysLeuGlyAsnGlnLeuLeuIleAlaIleLeuLeuLeu
```

FIG. 1M

```
            5960      5970      5980      5990      6000
      GGTTTGGCAAAGGTCTTGGGAATACTGGCATGATGAACAAGGGATGTCA
      GlyLeuAlaLysValLeuGlyIleLeuAlaEnd>
        ValTrpGlnArgSerTrpGluTyrTrpHisAspGluGlnGlyMetSer 6060      6070      6080      6090      6100
         TGCATTGCAAGAAAGGCTGTAGATGTCTAGGGGAAGGACATGGGGCAG
         MetHisCysLysLysGlyCysArgCysLeuGlyGluGlyHisGlyAlaG 6160      6170      6180      6190      6200
      ATGGAAGAAAGACCTCCAGAAAATGAAGGACCACAAAGGGAACCATGGA

MetGluGluArgProProGluAsnGluGlyProGlnArgGluProTrpAs 6260      6270      6280      6290      6300
         TTTTGATCCTCGCTTGCTAACTGCACTTGGTAATCATATCTATAATAGA
         PheAspProArgLeuLeuThrAlaLeuGlyAsnHisIleTyrAsnArg
                                                   tat->

6360      6370      6380      6390      6400
         GCGCTCTTCATGCATTTCAGAGGCGGATGCATCCACTCCAGAATCGGCC
         AlaLeuPheMetHisPheArgGlyGlyCysIleHisSerArgIleGlyG
           ArgSerSerCysIleSerGluAlaAspAlaSerThrProGluSerAla 6460      6470      6480      6490      6500
      CTATAACACATGCTATTGTAAAAGTGTTGCTACCATTGCCAGTTTTGTT
      LeuEnd
        TyrAsnThrCysTyrCysLysLysCysCysTyrHisCysGlnPheCysP 6560      6570      6580      6590      6600
       AGAACTCCGAAAAAGGCTAAGGCTAATACATCTTCTGCATCAAACAAGTA
       ArgThrProLysLysAlaLysAlaAsnThrSerSerAlaSerAsnAs>
        GluLeuArGlysArgLeuArgLeuIleHisLeuLeuHisGlnThrT>
                                                   env->

6660      6670      6680      6690      6700
         TGTCTATGGGATCTATTGTACTCTATATGTCACAGTCTTTTATGGTGTAC
         SerValTyrGlyIleTyrCysThrLeuTyrValThrValPheTyrGlyValP
```

FIG. 1N

```
       6710      6720      6730      6740      6750
CAGCTTGGAGGAATGCGACAATTCCCCTCTTTTGTGCAACCAAGAATAGGGAT
roAlaTrpArgAsnAlaThrIleProLeuPheCysAlaThrLysAsnArgAsp 6810      6820      6830      6840      6850
AGTGGCCCTTAATGTTACAGAAAGCTTTGATGCCTGGAATAATACAGTCACA
uValAlaLeuAsnValThrGluSerPheAspAlaTrpAsnAsnThrValThr 6910      6920      6930      6940      6950
CCTTGTGTAAAATTATCCCCATTATGCATTACTATGAGATGCAATAAAAGT
ProCysValLysLeuSerProLeuCysIleThrMetArgCysAsnLysSer 7010      7020      7030      7040      7050
CAACATCAACGACAGCATCAGCAAAAGTAGACATGGTCAATGAGACTAGTTCT
hrThrSerThrThrAlaSerAlaLysValAspMetValAsnGluThrSerSer 7110      7120      7130      7140      7150
AAGCTGTAAATTCAACATGACAGGGTTAAAAAGAGACAAGAAAAAGAGTAC
eSerCysLysPheAsnMetThrGlyLeuLysArgAspLysLysLysGluTyr 7210      7220      7230      7240      7250
ACTGGTAATGAAAGTAGATGTTACATGAACCACTGTAACACTTCTGTTATC
ThrGlyAsnGluSerArgCysTyrMetAsnHisCysAsnThrSerValIle 7310      7320      7330      7340      7350
GTGCACCTCCAGGTTATGCTTTGCTTAGATGTAATGACACAAATTATTCAGGC
ysAlaProProGlyTyrAlaLeuLeuArgCysAsnAspThrAsnTyrSerGly 7410      7420      7430      7440      7450
GATGGAGACACAGACTTCTACTTGGTTTGGCTTTAATGGAACTAGAGCAGAA
tMetGluThrGlnThrSerThrTrpPheGlyPheAsnGlyThrArgAlaGlu 7510      7520      7530      7540      7550
AGTTTAAATAAGTATTATAATCTAACAATGAAATGTAGAAGACCAGGAAAT
SerLeuAsnLysTyrTyrAsnLeuThrMetLysCysArgArgProGlyAsn 7610      7620      7630      7640      7650
AACCAATCAATGATAGGCCAAAGCAGGCATGGTGTTGGTTTGGAGGAAAA
lnProIleAsnAspArgProLysGlnAlaTrpCysTrpPheGlyGlyLys
```

FIG. 10

```
      6760        6770        6780        6790        6800
ACTTGGGGAACAACTCAGTGCCTACCAGATAATGGTGATTATTCAGA
ThrTrpGlyThrThrGlnCysLeuProAspAsnGlyAspTyrSerGl 6860        6870        6880        6890        6900
GAACAGGCAATAGAGGATGTATGGCAACTCTTTGAGACCTCAATAAAG
GluGlnAlaIleGluAspValTrpGlnLeuPheGluThrSerIleLys 6960        6970        6980        6990        7000
GAGACAGATAGATGGGGATTGACAAAATCAATAACAACAACAGCATCAA
GluThrAspArgTrpGlyLeuThrLysSerIleThrThrThrAlaSerT 7060        7070        7080        7090        7100
TGTATAGCCCAGGATAATTGCACAGGCTTGGAACAAGAGCAAATGAT
CysIleAlaGlnAspAsnCysThrGlyLeuGluGlnGluGlnMetIl 7160        7170        7180        7190        7200
AATGAAACTTGGTACTCTGCAGATTTGGTATGTGAACAAGGGAATAAC
AsnGluThrTrpTyrSerAlaAspLeuValCysGluGlnGlyAsnAsn 7260        7270        7280        7290        7300
CAAGAGTCTTGTGACAAACATTATTGGGATGCTATTAGATTTAGGTATT
GlnGluSerCysAspLysHisTyrTrpAspAlaIleArgPheArgTyrC 7360        7370        7380        7390        7400
TTTATGCCTAAATGTTCTAAGGTGGTGGTCTCTTCATGCACAAGGAT
PheMetProLysCysSerLysValValValSerSerCysThrArgMe 7460        7470        7480        7490        7500
AATAGAACTTATATTTACTGGCATGGTAGGGATAATAGGACTATAATT
AsnArgThrTyrIleTyrTrpHisGlyArgAspAsnArgThrIleIle 7560        7570        7580        7590        7600
AAGACAGTTTTACCAGTCACCATTATGTCTGGATTGGTTTTCCACTCAC
LysThrValLeuProValThrIleMetSerGlyLeuValPheHisSerG 7660        7670        7680        7690        7700
TGGAAGGATGCAATAAAAGAGGTGAAGCAGACCATTGTCAAACATCCCAG
TrpLysAspAlaIleLysGluValLysGlnThrIleValLysHisProAr
```

FIG. 1P

```
        7710        7720        7730        7740        7750
GTATACTGGAACTAACAATACTGATAAAATCAATTTGACGGCTCCTGGAGGA
gTyrThrGlyThrAsnAsnThrAspLysIleAsnLeuThrAlaProGlyGly 7810        7820        7830        7840        7850
CTCTACTGTAAAATGAATTGGTTTCTAAATTGGGTAGAAGATAGGAATACA
LeuTyrCysLysMetAsnTrpPheLeuAsnTrpValGluAspArgAsnThr 7910        7920        7930        7940        7950
ATATTAGACAAATAATCAACACTTGGCATAAAGTAGGCAAAAATGTTTAT
isIleArgGlnIleIleAsnThrTrpHisLysValGlyLysAsnValTyr 8010        8020        8030        8040        8050
CATAGCAAACATAGATTGGATTGATGGAAACCAAACTAATATCACCATGAGT
uIleAlaAsnIleAspTrpIleAspGlyAsnGlnThrAsnIleThrMetSer 8110        8120        8130        8140        8150
GTAGAGATCACTCCAATTGGCTTGGCCCCCACAGATGTGAAGAGGTACACT
ValGluIleThrProIleGlyLeuAlaProThrAspValLysArgTyrThr 8210        8220        8230        8240        8250
TGGGTTTTCTCGCAACGGCAGGTTCTGCAATGGGCGCGGCGTCGTTGACGCTG
euGlyPheLeuAlaThrAlaGlySerAlaMetGlyAlaAlaSerLeuThrLeu 8310        8320        8330        8340        8350
ACAGCTGTTGGACGTGGTCAAGAGACAACAAGAATTGTTGCGACTGACCGTC
nGlnLeuLeuAspValValLysArgGlnGlnGluLeuLeuArgLeuThrVal 8410        8420        8430        8440        8450
TTAAAGGACCAGGCGCAGCTGAATGCTTGGGGATGTGCGTTTAGACAAGTC
LeuLysAspGlnAlaGlnLeuAsnAlaTrpGlyCysAlaPheArgGlnVal 8510        8520        8530        8540        8550
ACAATGAGACTTGGCAAGAGTGGGAGCGAAAGGTTGACTTCTTGGAAGAA
snAsnGluThrTrpGlnGluTrpGluArgLysValAspPheLeuGluGlu
```

FIG. 1Q

```
        7760      7770      7780      7790      7800
    GGAGATCCGGAAGTTACCTTCATGTGGACAAATTGCAGAGGAGAGTTC
    GlyAspProGluValThrPheMetTrpThrAsnCysArgGlyGluPhe 7860      7870      7880      7890      7900
    GCTAACCAGAAGCCAAAGGAACAGCATAAAAGGAATTACGTGCCATGTC
    AlaAsnGlnLysProLysGluGlnHisLysArgAsnTyrValProCysH 7960      7970      7980      7990      8000
    TTGCCTCCAAGAGAGGGAGACCTCACGTGTAACTCCACAGTGACCAGTCT
    LeuProProArgGluGlyAspLeuThrCysAsnSerThrValThrSerLe 8060      8070      8080      8090      8100
    GCAGAGGTGGCAGAACTGTATCGATTGGAATTGGGAGATTATAAATTA
    AlaGluValAlaGluLeuTyrArgLeuGluLeuGlyAspTyrLysLeu 8160      8170      8180      8190      8200
    ACTGGTGGCACCTCAAGAAATAAAAGAGGGGTCTTTGTGCTAGGGTTCT
    ThrGlyGlyThrSerArgAsnLysArgGlyValPheValLeuGlyPheL
    OMP-><-TMP 8260      8270      8280      8290      8300
    ACCGCTCAGTCCCGAACTTTATTGGCTGGGATAGTGCAGCAACAGCA
    ThrAlaGlnSerArgThrLeuLeuAlaGlyIleValGlnGlnGlnGl 8360      8370      8380      8390      8400
    TGGGGAACAAAGAACCTCCAGACTAGGGTCACTGCCATCGAGAAGTAC
    TrpGlyThrLysAsnLeuGlnThrArgValThrAlaIleGluLysTyr 8460      8470      8480      8490      8500
    TGCCACACTACTGTACCATGGCCAAATGCAAGTCTAACACCAAAGTGGA
    CysHisThrThrValProTrpProAsnAlaSerLeuThrProLysTrpA 8560      8570      8580      8590      8600
    AATATAACAGCCCTCCTAGAGGAGGCACAAATTCAACAAGAGAAGAACAT
    AsnIleThrAlaLeuLeuGluGluAlaGlnIleGlnGlnGluLysAsnMe
```

FIG. 1R

```
         8610      8620      8630      8640      8650
GTATGAATTACAAAAGTTGAATAGCTGGGATGTGTTTGGCAATTGGTTTGAC
tTyrGluLeuGlnLysLeuAsnSerTrpAspValPheGlyAsnTrpPheAsp 8710      8720      8730      8740      8750
GGAGTAATACTGTTAAGAATAGTGATCTATATAGTACAAATGCTAGCTAAG
GlyValIleLeuLeuArgIleValIleTyrIleValGlnMetLeuAlaLys 8810      8820      8830      8840      8850
AGCAGACCCATATCCAACAGGACCCGGCACTGCCAACCAGAGAAGGCAAA
lnGlnThrHisIleGlnGlnAspProAlaLeuProThrArgGluGlyLys
  nArgProIleSerAsnArgThrArgHisCysGlnProGluLysAlaLys
 hrAsnProTyrProThrGlyProGlyThrAlaAsnGlnArgArgGlnAr 8910      8920      8930      8940      8950
AGAATATATTCATTTCCTGATCCGCCAACTGATACGCCTCTTGACTTGGCTA
eGluTyrIleHisPheLeuIleArgGlnLeuIleArgLeuLeuThrTrpLeu
nd
ArgIleTyrSerPheProAspProProThrAspThrProLeuAspLeuAla 9010      9020      9030      9040      9050
CCAATACTCCAGAGGCTCTCTGCGACCCTACAGAGGATTCGAGAAGTCCTC
ProIleLeuGlnArgLeuSerAlaThrLeuGlnArgIleArgGluValLeu
hrAsnThrProGluAlaLeuCysAspProThrGluAspSerArgSerPro 9110      9120      9130      9140      9150
CGGTCCAGGCCGTCTGGAGATCTGCGACAGAGACTCTTGCGGGCGCGTGG
laValGlnAlaValTrpArgSerAlaThrGluThrLeuAlaGlyAlaTrp
ArgSerArgProSerGlyAspLeuArgGlnArgLeuLeuArgAlaArgGly 9210      9220      9230      9240      9250
CCCCAGGAGGATTAGACAAGGGCTTGAGCTCACTCTCTTGTGAGGGACAG
eProArgArgIleArgGlnGlyLeuGluLeuThrLeuLeuEnd
erProGlyGlyLeuAspLysGlyLeuSerSerLeuSerCysGluGlyGln 9310      9320      9330      9340      9350
AGAGAGAGAAAAATTAGCATACAGAAACAAAATATGGATGATATAGATG
uGluArgGluLysLeuAlaTyrArgLysGlnAsnMetAspAspIleAsp
```

FIG. 1S

```
          8660      8670      8680      8690      8700
     CTTGCTTCTTGGATAAAGTATATACAATATGGAGTTTATATAGTTGTA
     LeuAlaSerTrpIleLysTyrIleGlnTyrGlyValTyrIleValVal 8760      8770      8780      8790      8800
     TTAAGGCAGGGGTATAGGCCAGTGTTCTCTTCCCCACCCTCTTATTTCC
     LeuArgGlnGlyTyrArgProValPheSerSerProProSerTyrPheG
                                                 tat->
                                                 rev->
          8860      8870      8880      8890      8900
     GAAAGAGACGGTGGAGAAGGCGGTGGCAACAGCTCCTGGCCTTGGCAGAT
     GluArgAspGlyGlyGluGlyGlyAsnSerSerTrpProTrpGlnIl
     LysGluThrValGluLysAlaValAlaThrAlaProGlyLeuGlyArgE
     GlySerArgTrpArgArgArgTrpGlnGlnLeuLeuAlaLeuAlaAsp 8960      8970      8980      8990      9000
     TTCAGCAACTGCAGAACCTTGCTATCGAGAGTATACCAGATCCTCCAA
     PheSerAsnCysArgThrLeuLeuSerArgValTyrGlnIleLeuGln IleGlnGlnLeuGlnAsnLeuAlaIleGluSerIleProAspProT 9060      9070      9080      9090      9100
     AGGACTGAACTGACCTACCTACAATATGGGTGGAGCTATTTCCATGAGG
     ArgThrGluLeuThrTyrLeuGlnTyrGlyTrpSerTyrPheHisGluA
     GlnAspEnd            nef-> MetGlyGlyAlaIleSerMetArg 9160      9170      9180      9190      9200
     GGAGACTTATGGGAGACTCTTAGGAGAGGTGGAAGATGGATACTCGCAAT
     GlyAspLeuTrpGluThrLeuArgArgGlyGlyArgTrpIleLeuAlaIl
     GluThrTyrGlyArgLeuLeuGlyValGluAspGlyTyrSerGlnS 9260      9270      9280      9290      9300
     AAATACAATCAGGGACAGTATATGAATACCATGGAGAAACCCAGCTGA
     LysTyrAsnGlnGlyGlnTyrMetAsnThrProTrpArgAsnProAlaGl 9360      9370      9380      9390      9400
     AGTAAGATGATGACTTGGTAGGGGTATCAGTGAGGCCAAAAGTTCCCCTA
     GluEndAspAspAspLeuValGlyValSerValArgProLysValProLeu
```

FIG. 1T

```
         9410       9420       9430       9440       9450
AGAACAATGAGTTACAAATTGGCAATAGACATGTCTCATTTTATAAAAGAA
ArgThrMetSerTyrLysLeuAlaIleAspMetSerHisPheIleLysGlu 9510       9520       9530       9540       9550
TAGACATATACTTAGAAAAGGAAGAAGGCATCATACCAGATTGGCAGGAT
euAspIleTyrLeuGluLysGluGluGlyIleIleProAspTrpGlnAsp 9610       9620       9630       9640       9650
GAAATTAGTCCCTGTAAATGTATCAGATGAGGCACAGGAGGATGAGGAGCAT
pLysLeuValProValAsnValSerAspGluAlaGlnGluAspGluGluHis 9710       9720       9730       9740       9750
GAGGTTCTAGCATGGAAGTTTGATCCAACTCTGGCCTACACTTATGAGGCA
GluValLeuAlaTrpLysPheAspProThrLeuAlaTyrThrTyrGluAla 9810       9820       9830       9840       9850
AAGAGGTTAGAAGAAGGCTAACCGCAAGAGGCCTTCTTAACATGGCTGACAAG
luGluValArgArgArgLeuThrAlaArgGlyLeuLeuAsnMetAlaAspLys 9910       9920       9930       9940       9950
GGGGAGGTACTGGGGAGGAGCCGGTCGGGAACGCCCACTTTCTTGATGTATAA 10010      10020      10030      10040      10050
GCAGATTGAGCCCTGGGAGGTTCTCTCCAGCACTAGCAGGTAGAGCCTGGGT 10110      10120      10130      10140      10150
ACTCCACGCTTGCTTGCTTAAAGCCCTCTTCAATAAAGCTGCCATTTTAGAA
                                   polyadenylation site 10210      10220      10230      10240      10250
CGGTACTCAATAATAAGAAGACCCTGGTCTGTTAGGACCCTTTCTGCTTTG
```

FIG. 1U

```
        9460      9470      9580      9590      9500
AAGGGGGGACTGGAAGGGATTTATTACAGTGCAAGAAGACATAGAATCT
LysGlyGlyLeuGluGlyIleTyrTyrSerAlaArgArgHisArgIleL
   3'LTR--->

9560      9570      9580      9590      9600
TACACCTCAGGACCAGGAATTAGATACCCAAAGACATTTGGCTGGCTATG
TyrThrSerGlyProGlyIleArgTyrProLysThrPheGlyTrpLeuTr 9660      9670      9680      9690      9700
TATTTAATGCATCCAGCTCAAACTTCCCAGTGGGATGACCCTTGGGGA
TyrLeuMetHisProAlaGlnThrSerGlnTrpAspAspProTrpGly 9760      9770      9780      9790      9800
TATGTTAGATACCCAGAAGAGTTTGGAAGCAAGTCAGGCCTGTCAGAGG
TyrValArgTyrProGluGluPheGlySerLysSerGlyLeuSerGluG 9860      9870      9880      9890      9900
AAGGAAACTCGCTGAAACAGCAGGGACTTTCCACAAGGGGATGTTAC
LysGluThrArgEnd 9960      9970      9980      9990     10000
ATATCACTGCATTTCGCTCTGTATTCAGTCGCTCTGCGGAGAGGCTG 10060     10070     10080     10090     10100
GTTCCCTGCTAGACTCTCACCAGCACTTGGCCGGTGCTGGGCAGAGTG 10160     10170     10180     10190     10200
GTAAGCTAGTGTGTGTTCCCATCTCTCCTAGCCGCCGCCTGGTCAACT 10260     10270
GGAAACCGAAGCAGGAAAATCCCTAGCA
```

FIG. 1V

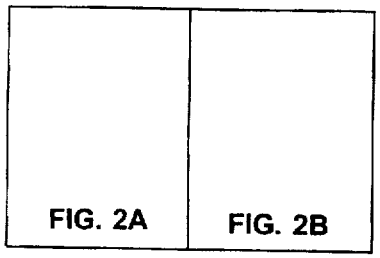
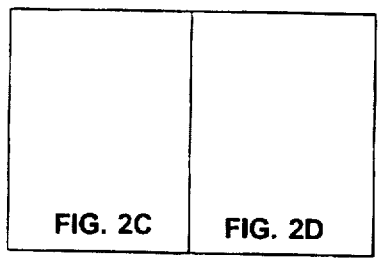
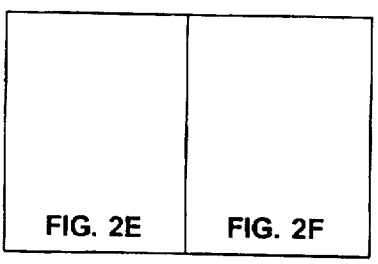
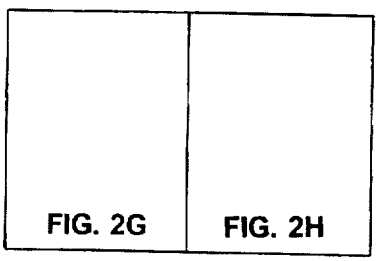
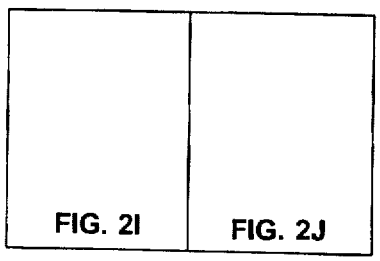
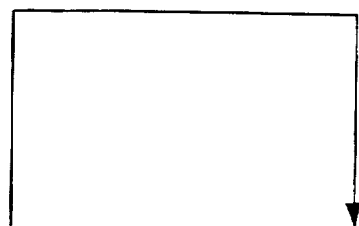
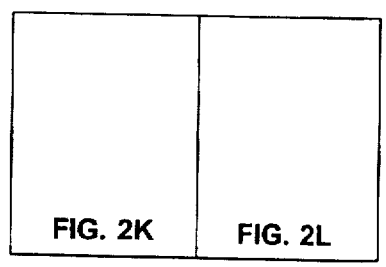
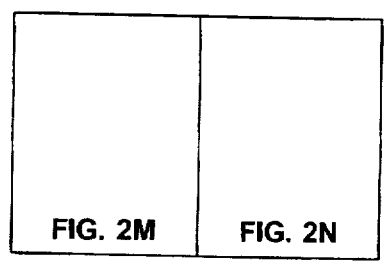
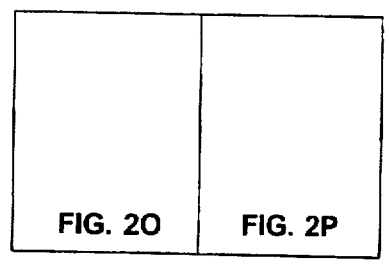
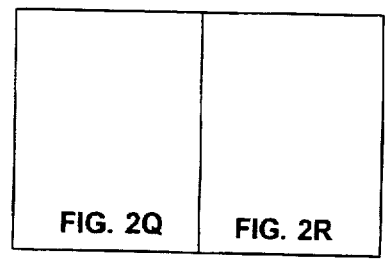
FIG. 2

```
                ┌─R
      1  GGTCTCTCTGGTTAGACCAGATCTGAGCCTGGGAGCTCTCTGGCTAACTAGGG
                                                             G

101  AGTGTGTGCCCGTCTGTTGTGTGACTCTGGTAACTAGAGATCCCTCAGACCC
               A

201  TGAAAGCGAAAGGGAAACCAGAGGAGCTCTCTCGACGCAGGACTCGGCTTGC
         ───
                                                  ┌─gag
                                                  MetGlyAlaArgAlaSer
    301  AAAAATTTTGACTAGCGGAGGCTAGAAGGAGAGAGATGGGTGCGAGAGCGTCA ProGlyGlyLysLysLysTyrLysLeuLysHisIleValTrpAlaSerArg
    401  GCCAGGGGGAAAGAAAAAATATAAATTAAAACATATAGTATGGGCAAGCAGG GlyCysArgGlnIleLeuGlyGlnLeuGlnProSerLeuGlnThrGlySerGlu
    501  GGCTGTAGACAAATACTGGGACAGCTACAACCATCCCTTCAGACAGGATCAG GlnArgIleGluIleLysAspThrLysGluAlaLeuAspLysIleGlu
    601  ATCAAAGGATAGAGATAAAAGACACCAAGGAAGCTTTAGACAAGATAGAG ┌─D24 gag
            GlyHisSerSerGlnValSerGlnAsnTyr ProIleValGlnAsnIleGln
    701  AGGACACAGCAGTCAGGTCAGCCAAAATTACCCTATAGTGCAGAACATCCAG ValLysValValGluGluLysAlaPheSerProGluValIleProMetPhe
    801  GTAAAAGTAGTAGAAGAGAAGGCTTTCAGCCCAGAAGTGATACCCATGTTT ThrValGlyGlyHisGlnAlaAlaMetGlnMetLeuLysGluThrIle
    901  ACACAGTGGGGGGACATCAAGCAGCCATGCAAATGTTAAAAGAGACCATC IleAlaProGlyGlnMetArgGluProArgGlySerAspIleAlaGly
   1001  TATTGCACCAGGCCAGATGAGAGAACCAAGGGGAAGTGACATAGCAGGA IleProValGlyGluIleTyrLysArgTrpIleIleLeuGlyLeuAsn
   1101  ATCCCAGTAGGAGAAATTTATAAAAGATGGATAATCCTGGGATTAAAT
```

FIG. 2A

```
                                                           R ←┬→ US
      AACCCACTGCTTAAGCCTCAATAAAGCTTGCCTTGAGTGCTTCAAGT

US ←┐
      TTTTAGTCAGTGTGGAAAATCTCTAGCAGTGGCGCCCGAACAGGGACT
                                R              PBS
                                        sd
                                        ▼
      TGAAGCGCGCACGGCAAGAGGCGAGGGGCGGCGACTGGTGAGTACGCC
                                              A
```

ValLeuSerGlyGlyGluLeuAspArgTrpGluLysIleArgLeuArg
GTATTAAGCGGGGGAGAATTAGATCGATGGGAAAAAATTCGGTTAAG

GluLeuGluArgPheAlaValAsnProGlyLeuLeuGluThrSerGlu
GAGCTAGAACGATTCGCAGTTAATCCTGGCCTGTTAGAAACATCAGAA

GluLeuArgSerLeuTyrAsnThrValAlaThrLeuTyrCysValHis
AAGAACTTAGATCATTATAATACAGTAGCAACCCTCTATTGTGTGC

GluGluGlnAsnLysSerLysLysLysAlaGlnGlnAlaAlaAlaAspThr
GAAGAGCAAAACAAAAGTAAGAAAAAAGCACAGCAAGCAGCAGCTGACAC

GlyGlnMetValHisGlnAlaIleSerProArgThrLeuAsnAlaTrp
GGGCAAATGGTACATCAGGCCATATCACCTAGAACTTTAAATGCATGG

SerAlaLeuSerGluGlyAlaThrProGlnAspLeuAsnThrMetLeuAsn
TCAGCATTATCAGAAGGAGCCACCCCACAAGATTTAAACACCATGCTAA

AsnGluGluAlaAlaGluTrpAspArgValHisProValHisAlaGlyPro
AATGAGGAAGCTGCAGAATGGGATAGAGTGCATCCAGTGCATGCAGGGCC

ThrThrSerThrLeuGlnGluGlnIleGlyTrpMetThrAsnAsnProPro
ACTACTAGTACCCTTCAGGAACAAATAGGATGGATGACAAATAATCCACCT

LysIleValArgMetTyrSerProThrSerIleLeuAspIleArgGlnGlyPro
AAAATAGTAAGAATGTATAGCCCTACCAGCATTCTGGACATAAGACAAGGAC

FIG. 2B

```
                                                         Arg
            LysGluProPheArgAspTyrValAspArgPheTyrLysThrLeuArg
     1201   CAAAAGAACCCTTTAGAGACTATGTAGACCGGTTCTATAAAACTCTAAGA
                                                            G

ValGlnAsnAlaAsnProAspCysLysThrIleLeuLysAlaLeuGlyProAlaAla
     1301 GGTCCAAAATGCGAACCCAGATTGTAAGACTATTTTAAAAGCATTGGGACC

ProGlyHisLysAlaArgValLeuAlaGluAlaMetSerGlnValThrAsn
     1401  CCCGGCCATAAGGCAAGAGTTTTGGCTGAAGCAATGAGCCAAGTAACAAAT

ValLysCysPheAsnCysGlyLysGluGlyHisThrAlaArgAsnCys
     1501  TGGTTAAGTGTTTCAATTGTGGCAAAGAAGGGCACACAGCCAGAAATTG

┌→pol
                                                     │GlyArgSerAla
           MetLysAspCysThrGluArgGlnAlaAsnPheLeuGlyLysIleCys
     1601  AATGAAAGATTGTACTGAGAGACAGGCTAATTTTTTAGGGAAGATCTGC SerProThrIleSerSerGluGlnThrArgAlaAsnSerProThrArg
           GlnProHisHisPhePheArgAlaAspGlnSerGlnGlnProHisGln
     1701  CAGCCCCACCATTTCTTCAGAGCAGACCAGAGCCAACAGCCCCACCAG AlaAspArgGlnGlyThrValSerPheAsnPheProGlnIleThrLeu
     1801  GCCGATAGACAAGGAACTGTATCCTTTAACTTCCCTCAGATCACTCTT LeuAspThrGlyAlaAspAspThrValLeuGluGluMetSerLeu
     1901  TATTAGATACAGGAGCAGATGATACAGTATTAGAAGAAATGAGTTTG ArgGlnTyrAspGlnIleLeuIleGluIleCysGlyHisLysAlaIle
     2001  AAGACAGTATGATCAAATACTCATAGAAATCTGTGGACATAAAGCTATA
                                                         G LeuThrGlnIleGlyCysThrLeuAsnPheProIleSerProIleGlu
     2101  TTGACTCAGATTGGTTGCACTTTAAATTTTCCCATTAGCCCTATTGAG
```

FIG. 2C

```
AlaGluGlnAlaSerGlnGluValLysAsnTrpMetThrGluThrLeuLeu
GCCGAGCAAGCTTCACAGGAGGTAAAAAATTGGATGACAGAAACCTTGTT

ThrLeuGluGluMetMetThrAlaCysGlnGlyValGlyGly
AGCAGCTACACTAGAAGAAATGATGACAGCATGTCAGGGAGTGGGAGGA

ThrAlaThrIleMetMetGlnArgGlyAsnPheArgAsnGlnArgLysMet
ACAGCTACCATAATGATGCAGAGAGGCAATTTTAGGAACCAAAGAAAGA

ArgAlaProArgLysLysGlyCysTrpLysCysGlyLysGluGlyHisGln
CAGGGCCCCTAGGAAAAAGGGCTGTTGGAAATGTGGAAAGGAAGGACACCA

PheLeuGlnGlyLysAlaArgGluPheSerSerGluGlnThrArgAlaAsn
LeuProThrArgGluGlyGlnGlyIlePhePheArgAlaAspGlnSerGln
CTTCCTACAAGGGAAGGCCAGGGAATTTTCTTCAGAGCAGACCAGAGCCAA
                                                  Leu
ArgGluLeuGlnValTrpGlyArgAspAsnAsnSerProSerGluAlaGly
LysArgAlaSerGlyLeuGlyAm*
AAGAGAGCTTCAGGTCTGGGGTAGAGACAACAACTCCCCCTCAGAAGCAGGA
                                                  T

TrpGlnArgProLeuValThrIleLysIleGlyGlyGlnLeuLysGluAlaLeu
TGGCAACGACCCCTCGTCACAATAAAGATAGGGGGCAACTAAAGGAAGCTC

ProGlyArgTrpLysProLysMetIleGlyGlyIleGlyGlyPheIleLysVal
CCAGGAAGATGGAAACCAAAAATGATAGGGGGAATTGGAGGTTTTATCAAAGT

GlyThrValLeuValGlyProThrProValAsnIleIleGlyArgAsnLeu
GGTACAGTATTAGTAGGACCTACACCTGTCAACATAATTGGAAGAAATCTG

ThrValProValLysLeuLysProGlyMetAspGlyProLysValLysGlnTrp
ACTGTACCAGTAAAATTAAAGCCAGGAATGGATGGCCCAAAAGTTAAACAAT
```

FIG. 2D

```
           ProLeuThrGluGluLysIleLysAlaLeuValGluIleCysThrGlu
2201  GGCCATTGACAGAAGAAAAATAAAAGCATTAGTAGAAATTTGTACAGA

ThrProValPheAlaIleLysLysLysAspSerThrLysTrpArgLys
2301  TACTCCAGTATTTGCCATAAAGAAAAAGACAGTACTAAATGGAGAAAA

GlnLeuGlyIleProHisProAlaGlyLeuLysLysLysLysSerVal
2401  CAATTAGGAATACCACATCCCGCAGGGTTAAAAAAGAAAAAATCAGTA

ArgLysTyrThrAlaPheThrIleProSerIleAsnAsnGluThrPro
2501  TCAGGAAGTATACTGCATTTACCATACCTAGTATAAACAATGAGACACCA

AlaIlePheGlnSerSerMetThrLysIleLeuGluProPheArgLys
2601  AGCAATATTCCAAAGTAGCATGACAAAAATCTTAGAGCCTTTTAGAAAA

SerAspLeuGluIleGlyGlnHisArgThrLysIleGluGluLeuArg
2701  TCTGACTTAGAAATAGGGCAGCATAGAACAAAAATAGAGGAGCTGAGA

ProProPheLeuTrpMetGlyTyrGluLeuHisProAspLysTrpThr
2801  AACCTCCATTCCTTTGGATGGGTTATGAACTCCATCCTGATAAATGGACA

GlnLysLeuValGlyLysLeuAsnTrpAlaSerGlnIleTyrProGly
2901  ACAGAAGTTAGTGGGGAAATTGAATTGGGCAAGTCAAATTTACCCAGGG
                                                         G

GluValIleProLeuThrGluGluAlaGluLeuGluLeuAlaGluAsn
3001  GAAGTAATACCACTAACAGAAGAAGCAGAGCTAGAACTGGCAGAAAAC

LeuIleAlaGluIleGlnLysGlnGlyGlnGlyGlnTrpThrTyr
3101  ACTTAATAGCAGAAATACAGAAGCAGGGGCAAGGCCAATGGACATAT

ArgGlyAlaHisThrAsnAspValLysGlnLeuThrGluAlaValGln
3201  GAGGGGTGCCCACACTAATGATGTAAAACAATTAACAGAGGCAGTGCAA
```

FIG. 2E

```
MetGluLysGluGlyLysIleSerLysIleGlyProGluAsnProTyrAsn
AATGGAAAAGGAAGGGAAAATTTCAAAAATTGGGCCTGAAAATCCATACAA

LeuValAspPheArgGluLeuAsnLysArgThrGlnAspPheTrpGluVal
TTAGTAGATTTCAGAGAACTTAATAAGAGAACTCAAGACTTCTGGGAAGTT

ThrValLeuAspValGlyAspAlaTyrPheSerValProLeuAspGluAspPhe
ACAGTACTGGATGTGGGTGATGCATATTTTCAGTTCCCTTAGATGAAGACT

GlyIleArgTyrGlnTyrAsnValLeuProGlnGlyTrpLysGlySerPro
GGGATTAGATATCAGTACAATGTGCTTCCACAGGGATGGAAAGGATCACC

GlnAsnProAspIleValIleTyrGlnTyrMetAspAspLeuTyrValGly
CAAAATCCAGACATAGTTATCTATCAATACATGGATGATTTGTATGTAGGA

GlnHisLeuLeuArgTrpGlyLeuThrThrProAspLysLysHisGlnLysGlu
CAACATCTGTTGAGGTGGGGACTTACCACACCAGACAAAAAACATCAGAAAG

ValGlnProIleValLeuProGluLysAspSerTrpThrValAsnAspIle
GTACAGCCTATAGTGCTGCCAGAAAAAGACAGCTGGACTGTCAATGACAT

IleLysValArgGlnLeuCysLysLeuLeuArgGlyThrLysAlaLeuThr
ATTAAAGTAAGGCAATTATGTAAACTCCTTAGAGGAACCAAAGCACTAACA

ArgGluIleLeuLysGluProValHisGlyValTyrTyrAspProSerLysAsp
AGAGAGATTCTAAAAGAACCAGTACATGGAGTGTATTATGACCCATCAAAAG

GlnIleTyrGlnGluProPheLysAsnLeuLysThrGlyLysTyrAlaArgMet
CAAATTTATCAAGAGCCATTTAAAAATCTGAAAACAGGAAAATATGCAAGAAT

LysIleThrThrGluSerIleValIleTrpGlyLysThrProLysPheLys
AAAATAACCACAGAAAGCATAGTAATATGGGGAAAGACTCCTAAATTTAAA
```

FIG. 2F

```
              LeuProIleGlnLysGluThrTrpGluThrTrpTrpThrGluTyrTrpGln
        3301  CTGCCCATACAAAGGAAACATGGGAAACATGGTGGACAGAGTATTGGC
                 A              A

LeuTrpTyrGlnLeuGluLysGluProIleValGlyAlaGluThr
        3401  AACTATGGTACCAGTTAGAGAAAGAACCCATAGTAGGAGCAGAAACT
                 T                                           C

ValThrAsnLysGlyArgGlnLysValValProLeuThrAsnThrThr
        3501  TGTTACTAACAAAGGAAGACAAAAGGTTGTCCCCTAACTAACACAACA

LeuGluValAsnIleValThrAspSerGlnTyrAlaLeuGlyIleIleGln
        3601  TTAGAAGTAAACATAGTAACAGACTCACAATATGCATTAGGAATCATTC

LeuIleLysLysGluLysValTyrLeuAlaTrpValProAlaHisLys
        3701  AGTTAATAAAAAAGGAAAAGGTCTATCTGGCATGGGTACCAGCACACAAA

LysIleLeuPheLeuAspGlyIleAspLysAlaGlnAspGluHisGlu
        3801  GAAAATACTATTTTTAGATGGAATAGATAAGGCCCAAGATGAACATGAG

ValValAlaLysGluIleValAlaSerCysAspLysCysGlnLeuLys
        3901  GTAGTAGCAAAAGAAATAGTAGCCAGCTGTGATAAATGTCAGCTAAAA

CysThrHisLeuGluGlyLysValIleLeuValAlaValHisValAla
        4001  ATTGTACACATTTAGAAGGAAAAGTTATCCTGGTAGCAGTTCATGTAGCC

AlaTyrPheLeuLeuLysLeuAlaGlyArgTrpProValLysThrIle
        4101  AGCATATTTTCTTTTAAAATTAGCAGGAAGATGGCCAGTAAAAACAATA

TrpTrpAlaGlyIleLysGlnGluPheGlyIleProTyrAsnProGln
        4201  TGGTGGGCGGGAATCAAGCAGGAATTTGGAATTCCCTACAATCCCCAA

ValArgAspGlnAlaGluHisLeuLysThrAlaValGlnMetAlaVal
        4301  AGGTAAGAGATCAGGCTGAACATCTTAAGACAGCAGTACAAATGGCAGTA
```

FIG. 2G

```
        AlaThrTrpIleProGluTrpGluPheValAsnThrProProLeuValLys
        AAGCCACCTGGATTCCTGAGTGGGAGTTTGTCAATACCCCTCCTTTAGTGA
                                                        T
                                                        Lys
    PheTyrValAspGlyAlaAlaAsnArgGluThrArgLeuGlyLysAlaGlyTyr
    TTCTATGTAGATGGGGCAGCTAACAGGGAGACTAGATTAGGAAAAGCAGGATA
                                                        A

AsnGlnLysThrGluLeuGlnAlaIleTyrLeuAlaLeuGlnAspSerGly
        AATCAGAAGACTGAGTTACAAGCAATTTATCTAGCTTTGCAGGATTCGGGA
               A                                         A

AlaGlnProAspGluSerGluSerGluLeuValAsnGlnIleIleGluGln
        AAGCACAACCAGATCAAAGTGAATCAGAGTTAGTCAATCAAATAATAGAGC
                    A

GlyIleGlyGlyAsnGluGlnValAspLysLeuValSerAlaGlyIleArg
        GGAATTGGAGGAAATGAACAAGTAGATAAATTAGTCAGTGCTGGAATCAG

LysTyrHisSerAsnTrpArgAlaMetAlaSerAspPheAsnLeuProPro
        AAATATCACAGTAATTGGAGAGCAATGGCTAGTGATTTTAACCTGCCACCT

GlyGluAlaMetHisGlyGlnValAspCysSerProGlyIleTrpGlnLeuAsp
        GGAGAAGCCATGCATGGACAAGTAGACTGTAGTCCAGGAATATGGCAACTAG

SerGlyTyrIleGluAlaGluValIleProAlaGluThrGlyGlnGluThr
        AGTGGATATATAGAAGCAGAAGTTATTCCAGCAGAAACAGGGCAGGAAAC

HisThrAspAsnGlySerAsnPheThrSerAlaThrValLysAlaAlaCys
        CATACAGACAATGGCAGCAATTTCACCAGTGCTACGGTTAAGGCCGCCTGT

SerGlnGlyValValGluSerMetAsnLysGluLeuLysLysIleIleGlyGln
        AGTCAAGGAGTAGTAGAATCTATGAATAAAGAATTAAAGAAAATTATAGGAC

PheIleHisAsnPheLysArgLysGlyGlyIleGlyGlyTyrSerAlaGly
        TTCATCCACAATTTTAAAAGAAAAGGGGGGATTGGGGGGTACAGTGCAGG
```

FIG. 2H

```
                GluArgIleValAspIleIleAlaThrAspIleGlnThrLysGluLeu
    4401 GGAAAGAATAGTAGACATAATAGCAACAGACATACAAACTAAAGAATTA

Asp                                           sd
         ArgAsnProLeuTrpLysGlyProAlaLysLeuLeuTrpLysGlyGlu
    4501 AGAAATCCACTTTGGAAAGGACCAGCAAAGCTCCTCTGGAAAGGTGAA
              G
                            ┌→P
                            'MetGluAsnArgTrpGlnValMetIle
            AlaLysIleIleArgAspTyrGlyLysGlnMetAlaGlyAspAspCys
    4601 AAGCAAAGATCATTAGGGATTATGGAAAACAGATGGCAGGTGATGATTGT

HisMetTyrValSerGlyLysAlaArgGlyTrpPheTyrArgHisHis
    4701 ACCATATGTATGTTTCAGGGAAAGCTAGGGGATGGTTTTATAGACATCAC

AspAlaArgLeuValIleThrThrTyrTrpGlyLeuHisThrGlyGlu
    4801 GGATGCTAGATTGGTAATAACAACATATTGGGGTCTGCATACAGGAGAA

TyrSerThrGlnValAspProGluLeuAlaAspGlnLeuIleHisLeu
    4901 TATAGCACACAAGTAGACCCTGAACTAGCAGACCAACTAATTCATCTG sd
              IleValSerProArgCysGluTyrGlnAlaGlyHisAsnLysValGly
    5001 ACATAGTTAGCCCTAGGTGTGAATATCAAGCAGGACATAACAAGGTAGGA

ProProLeuProSerValThrLysLeuThrGluAspArgTrpAsnLys
    5101 GCCACCTTTGCCTAGTGTTACGAAACTGACAGAGGATAGATGGAACAAG
                   A

5201 AGCTTTTAGAGGAGCTTAAGAATGAAGCTGTTAGACATTTTCCTAGGAT

5301 GGCAGGAGTGGAAGCCATAATAAGAATTCTGCAACAACTGCTGTTTATC

5401 GAGAGCAAGAAATGGAGCCAGTAGATCCTAGACTAGAGCCCTGGAAGCA
```

FIG. 21

```
                                                             sa
                                                             ▼
GlnLysGlnIleThrLysIleGlnAsnPheArgValTyrTyrArgAspSer
CAAAAACAAATTACAAAAATTCAAAATTTTCGGGTTTATTACAGGGACAGC

GlyAlaValValIleGlnAspAsnSerAspIleLysValValProArgArgLys
GGGGCAGTAGTAATACAAGATAATAGTGACATAAAAGTAGTGCCAAGAAGAA

ValTrpGlnValAspArgMetArgIleArgThrTrpLysSerLeuValLysHis
   ValAlaSerArgGlnAspGluAspAm*
GTGGCAAGTAGACAGGATGAGGATTAGAACATGGAAAAGTTTAGTAAAAC

TyrGluSerProHisProArgIleSerSerGluValHisIleProLeuGly
   TATGAAAGCCCTCATCCAAGAATAAGTTCAGAAGTACACATCCCACTAGG

Arg
ArgAspTrpHisLeuGlyGlnGlyValSerIleGluTrpArgLysLysArg
AGAGACTGGCATCTGGGTCAGGGAGTCTCCATAGAATGGAGGAAAAGAGA
       T                                                 G

His            sa
               ▼
TyrTyrPheAspCysPheSerAspSerAlaIleArgLysAlaLeuLeuGlyHis
TATTACTTTGACTGTTTTCAGACTCTGCTATAAGAAAGGCCTTATTAGGAC
C           T

Val
SerLeuGlnTyrLeuAlaLeuAlaAlaLeuIleThrProLysLysIleLys
TCTCTACAATACTTGGCACTAGCAGCATTAATAACACCAAAAAGATAAA
                                                 G

ProGlnLysThrLysGlyHisArgGlySerHisThrMetAsnGlyHisAM*
CCCCAGAAGACCAAGGGCCACAGAGGGAGCCACACAATGAATGGACACTAG

TTGGCTCCATGGCTTAGGGCAACATATCTATGAAACTTATGGGGATACTTG
   A
          sa
          ▼
CATTTTCAGAATTGGGTGTCGACATAGCAGAATAGGCGTTACTCGACAGAG

TCCAGGAAGTCAGCCTAAAACTGCTTGTACCAATTGCTATTGTAAAAAGTG
```

FIG. 2J

```
                                                                      G                    T
5501 TTGCTTTCATTGCCAAGTTTGTTTCATAACAAAAGCCTTAGGCATCTCCTAT
                    sd G              T
                       ▼
5601 ACTCATCAAGTTTCTCTATCAAAGCAGTAAGTAGTACATGTAATGCAACCTA
                                                        C

5701 TTGTGTGGTCCATAGTAATCATAGAATATAGGAAAATATTAAGACAAAGAAA

┌ env
         │MetArgValLysGluLysTyrGlnHisLeuTrpArgTrpGlyTrpArgTrp
5801 CAATGAGAGTGAAGGAGAAATATCAGCACTTGTGGAGATGGGGTGGAGATGG LeuTrpValThrValTyrTyrGlyValProValTrpLysGluAlaThrThr
5901 ATTGTGGGTCACAGTCTATTATGGGGTACCTGTGTGGAAGGAAGCAACCACC AsnValTrpAlaThrHisAlaCysValProThrAspProAsnProGlnGlu
6001 AATGTTTGGGCCACACATGCCTGTGTACCCACAGACCCCAACCCACAAGAA ValGluGlnMetHisGluAspIleIleSerLeuTrpAspGlnSerLeuLys
6101 TGGTAGAACAGATGCATGAGGATATAATCAGTTTATGGGATCAAAGCCTAAAG LeuLysAsnAspThrAsnThrAsnSerSerSerGlyArgMetIleMetGlu
6201 TTTGAAGAATGATACTAATACCAATAGTAGTAGCGGGAGAATGATAATGGAG GlyLysValGlnLysGluTyrAlaPhePheTyrLysLeuAspIleIlePro
6301 GGTAAGGTGCAGAAAGAATATGCATTTTTTATAAACTTGATATAATACCA IleThrGlnAlaCysProLysValSerPheGluProIleProIleHis
6401 TCATTACACAGGCCTGTCCAAAGGTATCCTTTGAGCCAATTCCCATACAT.

AsnGlyThrGlyProCysThrAsnValSerThrValGlnCysThrHisGly
6501 CAATGGAACAGGACCATGTACAAATGTCAGCACAGTACAATGTACACATGGA
```

FIG. 2K

```
                    sa
                    ▼
      GGCAGGAAGAAGCGGAGACAGCGACGAAGACCTCCTCAAGGCAGTCAG
                              G    A    GAA

TACAAATAGCAATAGTAGCATTAGTAGTAGCAATAATAATAGCAATAG
           C    (Taa)              C

AATAGACAGGTTAATTGATAGACTAATAGAAAGAGCAGAAGACAGTGG
                       A

------▶gp65^env
                                         Asn
      GlyThrMetLeuLeuGlyMetLeuMetIleCysSerAlaThrGluLys
      GGCACCATGCTCCTTGGGATGTTGATGATCTGTAGTGCTACAGAAAA
                                                    A ThrLeuPheCysAlaSerAspAlaLysAlaTyrAspThrGluValHis
      ACTCTATTTTGTGCATCAGATGCTAAAGCATATGATACAGAGGTACAT ValValLeuValAsnValThrGluAsnPheAsnMetTrpLysAsnAspMet
      GTAGTATTGGTAAATGTGACAGAAAATTTTAACATGTGGAAAAATGACA ProCysValLysLeuThrProLeuCysValSerLeuLysCysThrAsp
      CCATGTGTAAAATTAACCCCACTCTGTGTTAGTTTAAAGTGCACTGA Lys
      LysGlyGluIleLysAsnCysSerPheAsnIleSerThrSerIleArg
      AAAGGAGAGATAAAAAACTGCTCTTTCAATATCAGCACAAGCATAAGA
                                                    A IleAspAsnAspThrThrSerTyrThrLeuThrSerCysAsnThrSerVal
      ATAGATAATGATACTACCAGCTATACGTTGACAAGTTGTAACACCTCAG TyrCysAlaProAlaGlyPheAlaIleLeuLysCysAsnAsnLysThrPhe
      TATTGTGCCCCGGCTGGTTTTGCGATTCTAAAATGTAATAATAAGACGTT IleArgProValValSerThrGlnLeuLeuLeuAsnGlySerLeuAla
      ATTAGGCCAGTAGTATCAACTCAACTGCTGTTAAATGGCAGTCTAGCA
```

FIG. 2L

```
                                    Val
        GluGluGluValValIleArgSerAlaAsnPheThrAspAsnAlaLysThr
   6601 GAAGAAGAGGTAGTAATTAGATCTGCCAATTTCACAGACAATGCTAAAACC
                         T              G
                       Lys
        AsnAsnThrArgLysSerIleArgIleGlnArgGlyProGlyArgAla
   6701 ACAACAATACAAGAAAAGTATCCGTATCCAGAGAGGACCAGGGAGAGCA
                        AA                G
                    Ala                        Ala
        SerArgAlaLysTrpAsnAsnThrLeuLysGlnIleAspSerLysLeu
   6801 TAGTAGAGCAAAATGGAATAACACTTTAAAACAGATAGATAGCAAATTA
                      GC                         C

GlyAspProGluIleValThrHisSerPheAsnCysGlyGlyGluPhe
   6901 GGGGACCCAGAAATTGTAACGCACAGTTTTAATTGTGGAGGGGAATTT

SerThrGluGlySerAsnAsnThrGluGlySerAspThrIleThrLeu
   7001 GGAGTACTGAAGGGTCAAATAACACTGAAGGAAGTGACACAATCACACTC
                                                       C

MetTyrAlaProProIleSerGlyGlnIleArgCysSerSerAsnIle
   7101 AATGTATGCCCCTCCCATCAGCGGACAAATTAGATGTTCATCAAATATT
                                 T

IlePheArgProGlyGlyGlyAspMetArgAspAsnTrpArgSerGlu
   7201 ATCTTCAGACCTGGAGGAGGAGATATGAGGGACAATTGGAGAAGTGAA
                                             ┌─gp41 env
        AlaLysArgArgValValGlnArgGluLysArgAlaValGlyIle
   7301 AGGCAAAGAGAAGAGTGGTGCAGAGAGAAAAAGAGCAGTGGGAATA SerMetThrLeuThrValGlnAlaArgGlnLeuLeuSerGlyIleVal
   7401 GTCAATGACGCTGACGGTACAGGCCAGACAATTATTGTCTGGTATAGTG GlnLeuThrValTrpGlyIleLysGlnLeuGlnAlaArgIleLeuAla
   7501 CAACTCACAGTCTGGGGCATCAAGCAGCTCCAGGCAAGAATCCTGGCT LysLeuIleCysThrThrAlaValProTrpAsnAlaSerTrpSer
   7601 GAAAACTCATTTGCACCACTGCTGTGCCTTGGAATGCTAGTTGGAGT
```

FIG. 2M

```
                              Thr
    IleIleValGlnLeuAsnGlnSerValGluIleAsnCysThrArgProAsn
    ATAATAGTACAGCTGAACCAATCTGTAGAAATTAATTGTACAAGACCCA
                                                    AC

PheValThrIleGlyLysIleGlyAsnMetArgGlnAlaHisCysAsnIle
    TTTGTTACAATAGGAAAAATAGGAAATATGAGACAAGCACATTGTAACAT

ArgGluGlnPheGlyAsnAsnLysThrIleIlePheLysGlnSerSerGly
    AGAGAACAATTTGGAAATAATAAAACAATAATCTTTAAGCAATCCTCAGGA

PheTyrCysAsnSerThrGlnLeuPheAsnSerThrTrpPheAsnSerThrTrp
    TTCTACTGTAATTCAACACAACTGTTTAATAGTACTTGGTTTAATAGTACTT

Ile
    ProCysArgIleLysGlnPheIleAsnMetTrpGlnGluValGlyLysAla
    CCATGCAGAATAAAACAATTTATAAACATGTGGCAGGAAGTAGGAAAAGC
                                                    A
                                        Ser
    ThrGlyLeuLeuLeuThrArgAspGlyGlyAsnAsnAsnAsnGluSerGlu
    ACAGGGCTGCTATTAACAAGAGATGGTGGTAATAACAACAATGAGTCCGAG
                                                      G

LeuTyrLysTyrLysValValLysIleGluProLeuGlyValAlaProThrLys
    TTATATAAATATAAAGTAGTAAAAATTGAACCATTAGGAGTAGCACCCACCA

GlyAlaLeuPheLeuGlyPheLeuGlyAlaAlaGlySerThrMetGlyAlaAla
    GGAGCTTTGTTCCTTGGGTTCTTGGGAGCAGCAGGAAGCACTATGGGCGCAGC

GlnGlnGlnAsnAsnLeuLeuArgAlaIleGluAlaGlnGlnHisLeuLeu
    CAGCAGCAGAACAATTTGCTGAGGGCTATTGAGGCGCAACAGCATCTGTTG

ValGluArgTyrLeuLysAspGlnGlnLeuLeuGlyIleTrpGlyCysSerGly
    GTGGAAAGATACCTAAAGGATCAACAGCTCCTGGGGATTTGGGGTTGCTCTG

HisThr
    AsnLysSerLeuGluGlnIleTrpAsnAsnMetThrTrpMetGluTrpAspArg
    AATAAATCTCTGGAACAGATTTGGAATAACATGACCTGGATGGAGTGGGACAG
                                                C  C
```

FIG. 2N

```
              GluIleAsnAsnTyrThrSerLeuIleHisSerLeuIleGluGluSerGln
7701 AGAAATTAACAATTACACAAGCTTAATACACTCCTTAATTGAAGAATCGCAA

Ser              Phe
     AlaAsnLeuTrpAsnTrpLeuAsnIleThrAsnTrpLeuTrpTyrIleLys
7801 GCAAATTTGTGGAATTGGTTGAACATAACAAATTGGCTGTGGTATATAAAA
          G              T
                  Val
     ValLeuSerIleValAsnArgValArgGlnGlyTyrSerProLeuSerPhe
7901 CTGTACTTTCTATAGTAAATAGAGTTAGGCAGGGATATTCACCATTATCGTTT
            G       G
                Gly
     GluGluGluAspGlyGluArgAspArgAspArgSerIleArgLeuValAsn
8001 AGAAGAAGAAGATGGAGAGAGAGACAGAGACAGATCCATTCGATTAGTGAAC
                          G

SerTyrHisArgLeuArgAspLeuLeuLeuIleValThrArgIleValGlu
8101 AGCTACCACCGCTTGAGAGACTTACTCTTGATTGTAACGAGGATTGTGGAA

GlnTyrTrpSerGlnGluLeuLysAsnSerAlaValSerLeuLeuAsnAla
8201 TACAATATTGGAGTCAGGAGCTAAAGAATAGTGCTGTTAGCTTGCTCAATGCC

GlnGlyAlaTyrArgAlaIleArgHisIleProArgArgIleArgGlnGly
8301 ACAAGGAGCTTATAGAGCTATTCGCCACATACCTAGAAGAATAAGACAGGGC

Val
     ValIleGlyTrpProAlaValArgGluArgMetArgArgAlaGluProAla
8401 TGTGATTGGATGGCCTGCTGTAAGGGAAAGAATGAGACGAGCTGAGCCAGCA
                          G

Thr         Asp
     IleThrSerSerAsnThrAlaAlaAsnAsnAlaAlaCysAlaTrpLeuGlu
8501 ATCACAAGTAGCAACACAGCAGCTAACAATGCTGCTTGTGCCTGGCTAGAA
                T        C        A

ArgProMetThrTyrLysAlaAlaValAspLeuSerHisPheLeuLys
8601 TAAGACCAATGACTTACAAGGCAGCTGTAGATCTTAGCCACTTTTTAAAA

LeuAspLeuTrpIleTyrHisThrGlnGlyTyrPheProAspTrpGlnAsp
8701 CCTTGATCTGTGGATCTACCACACACAAGGCTACTTCCCTGATTGGCAGAAC
```

FIG. 20

```
AsnGlnGlnGluLysAsnGluGlnGluLeuLeuGluLeuAspLysTrp
AACCAGCAAGAAAAGAATGAACAAGAATTATTGGAATTAGATAAATGG
         A

LeuPheIleMetIleValGlyGlyLeuValGlyLeuArgIleValPheAla
TTATTCATAATGATAGTAGGAGGCTTGGTAGGTTTAAGAATAGTTTTTG
              sa
              ▼
   GlnThrHisLeuProThrProArgGlyProAspArgProGluGlyIle
   CAGACCCACCTCCCAACCCCGAGGGGACCCGACAGGCCCGAAGGAAT

GlySerLeuAlaLeuIleTrpAspAspLeuArgSerLeuCysLeuPhe
GGATCCTTAGCACTTATCTGGGACGATCTGCGGAGCCTGTGCCTCTTC

LeuLeuGlyArgArgGlyTrpGluAlaLeuLysTyrTrpTrpAsnLeuLeu
CTTCTGGGACGCAGGGGGTGGGAAGCCCTCAAATATTGGTGGAATCTCC

ThrAlaIleAlaValAlaGluGlyThrAspArgValIleGluValVal
ACAGCTATAGCAGTAGCTGAGGGGACAGATAGGGTTATAGAAGTAGT
                                    ┌▶E
LeuGluArgIleLeuLeuOC*' MetGlyGlyLysTrpSerLysSerSer
TTGGAAAGGATTTTGCTATAAGATGGGTGGCAAGTGGTCAAAAAGTAG

AlaAspGlyValGlyAlaAlaSerArgAspLeuGluLysHisGlyAla
GCAGATGGGGTGGGAGCAGCATCTCGAGACCTAGAAAAACATGGAGCA
                      Glu
AlaGlnGluGluGluLysValGlyPheProValThrProGlnValProLeu
GCACAAGAGGAGGAGAAGGTGGGTTTTCCAGTCACACCTCAGGTACCTT
                                G
                          ┌▶U3
GluLysGlyGlyLeuGluGlyLeuIleHisSerGlnArgArgGlnAspIle
GAAAAGGGGGGACTGGAAGGGCTAATTCACTCCCAACGAAGACAAGATAT
───────────
   (+)       R

TyrThrProGlyProGlyIleArgTyrProLeuThrPheGlyTrpCys
TACACACCAGGACCAGGGATCAGATATCCACTGACCTTTGGATGGTGC
```

FIG. 2P

```
                                    Glu     Leu
        TyrLysLeuValProValGluProAspLysValGluGluAlaAsnLysGly
8801    TACAAGCTAGTACCAGTTGAGCCAGATAAGGTAGAAGAGGCCAACAAAGGA
                                  G     T       A

GluArgGluValLeuGluTrpArgPheAspSerArgLeuAlaPheHis
8901    CGGAGAGAGAAGTGTTAGAGTGGAGGTTTGACAGCCGCCTAGCATTTCAT

9001    AGCTTGCTACAAGGGACTTTCCGCTGGGGACTTTCCAGGGAGGCGTGGC
                            US◄─┬─►R
9101    GCTTTTGCCTGTACTGGGTCTCTCTGGTTAGACCAGATCTGAGCCTGG
               R◄┐
9201    CCTTGAGTGCTTC┘
```

FIG. 2Q

GluAsnThrSerLeuLeuHisProValSerLeuHisGlyMetAspAspPro
GAGAACACCAGCTTGTTACACCCTGTGAGCCTGCATGGAATGGATGACC

HisValAlaArgGluLeuHisProGluTyrPheLysAsnCysOP*
CACGTGGCCCGAGAGCTGCATCCGGAGTACTTCAAGAACTGCTGATATCG

CTGGGCGGGACTGGGGAGTGGCGAGCCCTCAGATGCTGCA TATAAG CAGCT
                                                C

GAGCTCTCTGGCTAACTAGAGAACCCACTGCTTAAGCCTC AATAAA GCTTG

FIG. 2R

SEQ ID NO: 5

```
TGGAAGGGCT AATTTGGTCC CAAAAAAGAC AAGAGATCCT TGATCTGTGG ATCTACCACA    60
CACAAGGCTA CTTCCCTGAT TGGCAGAACT ACACACCAGG GCCAGGGATC AGATATCCAC   120
TGACCTTTGG ATGGTGCTTC AAGTTAGTAC CAGTTGAACC AGAGCAAGTA GAAGAGGCCA   180
AATAAGGAGA GAAGAACAGC TTGTTACACC CTATGAGCCA GCATGGGATG GAGGACCCGG   240
AGGGAGAAGT ATTAGTGTGG AAGTTTGACA GCCTCCTAGC ATTTCGTCAC ATGGCCCGAG   300
AGCTGCATCC GGAGTACTAC AAAGACTGCT GACATCGAGC TTTCTACAAG GGACTTTCCG   360
CTGGGGACTT TCCAGGGAGG TGTGGCCTGG GCGGGACTGG GGAGTGGCGA GCCCTCAGAT   420
GCTACATATA AGCAGCTGCT TTTTGCCTGT ACTGGGTCTC TCTGGTTAGA CCAGATCTGA   480
GCCTGGGAGC TCTCTGGCTA ACTAGGGAAC CCACTGCTTA AGCCTCAATA AAGCTTGCCT   540
TGAGTGCTCA AGTAGTGTG TGCCCGTCTG TTGTGTGACT CTGGTAACTA GAGATCCCTC   600
AGACCCTTTT AGTCAGTGTG GAAAATCTCT AGCAGTGGCG CCCGAACAGG GACTTGAAAG   660
CGAAAGTAAA GCCAGAGGAG ATCTCTCGAC GCAGGACTCG GCTTGCTGAA GCGCGCACGG   720
CAAGAGGCGA GGGGCGGCGA CTGGTGAGTA CGCCAAAAAT TTTGACTAGC GGAGGCTAGA   780
AGGAGAGAGA TGGGTGCGAG AGCGTCGGTA TTAAGCGGGG GAGAATTAGA TAAATGGGAA   840
AAAATTCGGT TAAGGCCAGG GGGAAAGAAA CAATATAAAC TAAAACATAT AGTATGGGCA   900
AGCAGGGAGC TAGAACGATT CGCAGTTAAT CCTGGCCTTT TAGAGACATC AGAAGGCTGT   960
AGACAAATAC TGGGACAGCT ACAACCATCC CTTCAGACAG GATCAGAAGA ACTTAGATCA  1020
TTATATAATA CAATAGCAGT CCTCTATTGT GTGCATCAAA GGATAGATGT AAAAGACACC  1080
AAGGAAGCCT TAGATAAGAT AGAGGAAGAG CAAAACAAAA GTAAGAAAAA GGCACAGCAA  1140
GCAGCAGCTG ACACAGGAAA CAACAGCCAG GTCAGCCAAA ATTACCCTAT AGTGCAGAAC  1200
CTCCAGGGGC AAATGGTACA TCAGGCCATA TCACCTAGAA CTTTAAATGC ATGGGTAAAA  1260
GTAGTAGAAG AGAAGGCTTT CAGCCCAGAA GTAATACCCA TGTTTTCAGC ATTATCAGAA  1320
GGAGCCACCC CACAAGATTT AAATACCATG CTAAACACAG TGGGGGGACA TCAAGCAGCC  1380
ATGCAAATGT TAAAAGAGAC CATCAATGAG GAAGCTGCAG AATGGGATAG ATTGCATCCA  1440
GTGCATGCAG GGCCTATTGC ACCAGGCCAG ATGAGAGAAC CAAGGGGAAG TGACATAGCA  1500
GGAACTACTA GTACCCTTCA GGAACAAATA GGATGGATGA CACATAATCC ACCTATCCCA  1560
GTAGGAGAAA TCTATAAAAG ATGGATAATC CTGGGATTAA ATAAAATAGT AAGAATGTAT  1620
AGCCCTACCA GCATTCTGGA CATAAGACAA GGACCAAAGG AACCCTTTAG AGACTATGTA  1680
GACCGATTCT ATAAAACTCT AAGAGCCGAG CAAGCTTCAC AAGAGGTAAA AAATTGGATG  1740
ACAGAAACCT TGTTGGTCCA AAATGCGAAC CCAGATTGTA AGACTATTTT AAAAGCATTG  1800
```

FIG. 3A

```
GGACCAGGAG CGACACTAGA AGAAATGATG ACAGCATGTC AGGGAGTGGG GGGACCCGGC  1860
CATAAAGCAA GAGTTTTGGC TGAAGCAATG AGCCAAGTAA CAAATCCAGC TACCATAATG  1920
ATACAGAAAG GCAATTTTAG GAACCAAAGA AAGACTGTTA AGTGTTTCAA TTGTGGCAAA  1980
GAAGGGCACA TAGCCAAAAA TTGCAGGGCC CCTAGGAAAA AGGGCTGTTG GAAATGTGGA  2040
AAGGAAGGAC ACCAAATGAA AGATTGTACT GAGAGACAGG CTAATTTTTT AGGGAAGATC  2100
TGGCCTTCCC ACAAGGGAAG GCCAGGGAAT TTTCTTCAGA GCAGACCAGA GCCAACAGCC  2160
CCACCAGAAG AGAGCTTCAG GTTTGGGGAA GAGACAACAA CTCCCTCTCA GAAGCAGGAG  2220
CCGATAGACA AGGAACTGTA TCCTTTAGCT TCCCTCAGAT CACTCTTTGG CAGCGACCCC  2280
TCGTCACAAT AAAGATAGGG GGGCAATTAA AGGAAGCTCT ATTAGATACA GGAGCAGATG  2340
ATACAGTATT AGAAGAAATG AATTTGCCAG GAAGATGGAA ACCAAAAATG ATAGGGGGAA  2400
TTGGAGGTTT TATCAAAGTA GGACAGTATG ATCAGATACT CATAGAAATC TGCGGACATA  2460
AAGCTATAGG TACAGTATTA GTAGGACCTA CACCTGTCAA CATAATTGGA AGAAATCTGT  2520
TGACTCAGAT TGGCTGCACT TTAAATTTTC CCATTAGTCC TATTGAGACT GTACCAGTAA  2580
AATTAAAGCC AGGAATGGAT GGCCCAAAAG TTAAACAATG GCCATTGACA GAAGAAAAAA  2640
TAAAAGCATT AGTAGAAATT TGTACAGAAA TGGAAAAGGA AGGAAAAATT TCAAAAATTG  2700
GGCCTGAAAA TCCATACAAT ACTCCAGTAT TTGCCATAAA GAAAAAGAC AGTACTAAAT  2760
GGAGAAAATT AGTAGATTTC AGAGAACTTA ATAAGAGAAC TCAAGATTTC TGGGAAGTTC  2820
AATTAGGAAT ACCACATCCT GCAGGGTTAA AACAGAAAAA ATCAGTAACA GTACTGGATG  2880
TGGGCGATGC ATATTTTTCA GTTCCCTTAG ATAAAGACTT CAGGAAGTAT ACTGCATTTA  2940
CCATACCTAG TATAAACAAT GAGACACCAG GGATTAGATA TCAGTACAAT GTGCTTCCAC  3000
AGGGATGGAA AGGATCACCA GCAATATTCC AGTGTAGCAT GACAAAAATC TTAGAGCCTT  3060
TTAGAAAACA AAATCCAGAC ATAGTCATCT ATCAATACAT GGATGATTTG TATGTAGGAT  3120
CTGACTTAGA AATAGGGCAG CATAGAACAA AAATAGAGGA ACTGAGACAA CATCTGTTGA  3180
GGTGGGGATT TACCACACCA GACAAAAAAC ATCAGAAAGA ACCTCCATTC CTTTGGATGG  3240
GTTATGAACT CCATCCTGAT AAATGGACAG TACAGCCTAT AGTGCTGCCA GAAAAGGACA  3300
GCTGGACTGT CAATGACATA CAGAAATTAG TGGGAAAATT GAATTGGGCA AGTCAGATTT  3360
ATGCAGGGAT TAAAGTAAGG CAATTATGTA AACTTCTTAG GGGAACCAAA GCACTAACAG  3420
AAGTAGTACC ACTAACAGAA GAAGCAGAGC TAGAACTGGC AGAAAACAGG GAGATTCTAA  3480
AAGAACCGGT ACATGGAGTG TATTATGACC CATCAAAAGA CTTAATAGCA GAAATACAGA  3540
AGCAGGGGCA AGGCCAATGG ACATATCAAA TTTATCAAGA GCCATTTAAA AATCTGAAAA  3600
CAGGAAAATA TGCAAGAATG AAGGGTGCCC ACACTAATGA TGTGAAACAA TTAACAGAGG  3660
CAGTACAAAA AATAGCCACA GAAAGCATAG TAATATGGGG AAAGACTCCT AAATTTAAAT  3720
```

FIG. 3B

```
TACCCATACA AAAGGAAACA TGGGAAGCAT GGTGGACAGA GTATTGGCAA GCCACCTGGA 3780
TTCCTGAGTG GGAGTTTGTC AATACCCCTC CCTTAGTGAA GTTATGGTAC CAGTTAGAGA 3840
AAGAACCCAT AATAGGAGCA GAAACTTTCT ATGTAGATGG GGCAGCCAAT AGGGAAACTA 3900
AATTAGGAAA AGCAGGATAT GTAACTGACA GAGGAAGACA AAAAGTTGTC CCCCTAACGG 3960
ACACAACAAA TCAGAAGACT GAGTTACAAG CAATTCATCT AGCTTTGCAG GATTCGGGAT 4020
TAGAAGTAAA CATAGTGACA GACTCACAAT ATGCATTGGG AATCATTCAA GCACAACCAG 4080
ATAAGAGTGA ATCAGAGTTA GTCAGTCAAA TAATAGAGCA GTTAATAAAA AAGGAAAAAG 4140
TCTACCTGGC ATGGGTACCA GCACACAAAG GAATTGGAGG AAATGAACAA GTAGATGGGT 4200
TGGTCAGTGC TGGAATCAGG AAAGTACTAT TTTTAGATGG AATAGATAAG GCCCAAGAAG 4260
AACATGAGAA ATATCACAGT AATTGGAGAG CAATGGCTAG TGATTTTAAC CTACCACCTG 4320
TAGTAGCAAA AGAAATAGTA GCCAGCTGTG ATAATGTCA GCTAAAAGGG GAAGCCATGC 4380
ATGGACAAGT AGACTGTAGC CCAGGAATAT GGCAGCTAGA TTGTACACAT TTAGAAGGAA 4440
AAGTTATCTT GGTAGCAGTT CATGTAGCCA GTGGATATAT AGAAGCAGAA GTAATTCCAG 4500
CAGAGACAGG GCAAGAAACA GCATACTTCC TCTTAAAATT AGCAGGAAGA TGGCCAGTAA 4560
AAACAGTACA TACAGACAAT GGCAGCAATT TCACCAGTAC TACAGTTAAG GCCGCCTGTT 4620
GGTGGGCGGG GATCAAGCAG GAATTTGGCA TTCCCTACAA TCCCCAAAGT CAAGGAGTAA 4680
TAGAATCTAT GAATAAAGAA TTAAAGAAAA TTATAGGACA GGTAAGAGAT CAGGCTGAAC 4740
ATCTTAAGAC AGCAGTACAA ATGGCAGTAT TCATCCACAA TTTTAAAAGA AAAGGGGGGA 4800
TTGGGGGGTA CAGTGCAGGG GAAAGAATAG TAGACATAAT AGCAACAGAC ATACAAACTA 4860
AAGAATTACA AAAACAAATT ACAAAAATTC AAAATTTTCG GGTTTATTAC AGGGACAGCA 4920
GAGATCCAGT TTGGAAAGGA CCAGCAAAGC TCCTCTGGAA AGGTGAAGGG GCAGTAGTAA 4980
TACAAGATAA TAGTGACATA AAAGTAGTGC CAAGAAGAAA AGCAAAGATC ATCAGGGATT 5040
ATGGAAAACA GATGGCAGGT GATGATTGTG TGGCAAGTAG ACAGGATGAG GATTAACACA 5100
TGGAAAAGAT TAGTAAAACA CCATATGTAT ATTTCAAGGA AAGCTAAGGA CTGGTTTTAT 5160
AGACATCACT ATGAAAGTAC TAATCCAAAA ATAAGTTCAG AAGTACACAT CCCACTAGGG 5220
GATGCTAAAT TAGTAATAAC AACATATTGG GGTCTGCATA CAGGAGAAAG AGACTGGCAT 5280
TTGGGTCAGG GAGTCTCCAT AGAATGGAGG AAAAAGAGAT ATAGCACACA AGTAGACCCT 5340
GACCTAGCAG ACCAACTAAT TCATCTGCAC TATTTTGATT GTTTTTCAGA ATCTGCTATA 5400
AGAAATACCA TATTAGGACG TATAGTTAGT CCTAGGTGTG AATATCAAGC AGGACATAAC 5460
AAGGTAGGAT CTCTACAGTA CTTGGCACTA GCAGCATTAA TAAAACCAAA ACAGATAAAG 5520
CCACCTTTGC CTAGTGTTAG GAAACTGACA GAGGACAGAT GGAACAAGCC CAGAAGACC 5580
AAGGGCCACA GAGGGAGCCA TACAATGAAT GGACACTAGA GCTTTTAGAG GAACTTAAGA 5640
```

FIG. 3C

```
GTGAAGCTGT TAGACATTTT CCTAGGATAT GGCTCCATAA CTTAGGACAA CATATCTATG 5700
AAACTTACGG GGATACTTGG GCAGGAGTGG AAGCCATAAT AAGAATTCTG CAACAACTGC 5760
TGTTTATCCA TTTCAGAATT GGGTGTCGAC ATAGCAGAAT AGGCGTTACT CGACAGAGGA 5820
GAGCAAGAAA TGGAGCCAGT AGATCCTAGA CTAGAGCCCT GGAAGCATCC AGGAAGTCAG 5880
CCTAAAACTG CTTGTACCAA TTGCTATTGT AAAAAGTGTT GCTTTCATTG CCAAGTTTGT 5940
TTCATGACAA AAGCCTTAGG CATCTCCTAT GGCAGGAAGA AGCGGAGACA GCGACGAAGA 6000
GCTCATCAGA ACAGTCAGAC TCATCAAGCT TCTCTATCAA AGCAGTAAGT AGTACATGTA 6060
ATGCAACCTA TAATAGTAGC AATAGTAGCA TTAGTAGTAG CAATAATAAT AGCAATAGTT 6120
GTGTGGTCCA TAGTAATCAT AGAATATAGG AAAATATTAA GACAAAGAAA AATAGACAGG 6180
TTAATTGATA GACTAATAGA AAGAGCAGAA GACAGTGGCA ATGAGAGTGA AGGAGAAGTA 6240
TCAGCACTTG TGGAGATGGG GGTGGAAATG GGGCACCATG CTCCTTGGGA TATTGATGAT 6300
CTGTAGTGCT ACAGAAAAAT TGTGGGTCAC AGTCTATTAT GGGGTACCTG TGTGGAAGGA 6360
AGCAACCACC ACTCTATTTT GTGCATCAGA TGCTAAAGCA TATGATACAG AGGTACATAA 6420
TGTTTGGGCC ACACATGCCT GTGTACCCAC AGACCCCAAC CCACAAGAAG TAGTATTGGT 6480
AAATGTGACA GAAAATTTTA ACATGTGGAA AAATGACATG GTAGAACAGA TGCATGAGGA 6540
TATAATCAGT TTATGGGATC AAAGCCTAAA GCCATGTGTA AAATTAACCC CACTCTGTGT 6600
TAGTTTAAAG TGCACTGATT TGAAGAATGA TACTAATACC AATAGTAGTA GCGGGAGAAT 6660
GATAATGGAG AAAGGAGAGA TAAAAAACTG CTCTTTCAAT ATCAGCACAA GCATAAGAGA 6720
TAAGGTGCAG AAAGAATATG CATTCTTTTA TAAACTTGAT ATAGTACCAA TAGATAATAC 6780
CAGCTATAGG TTGATAAGTT GTAACACCTC AGTCATTACA CAGGCCTGTC CAAAGGTATC 6840
CTTTGAGCCA ATTCCCATAC ATTATTGTGC CCCGGCTGGT TTTGCGATTC TAAAATGTAA 6900
TAATAAGACG TTCAATGGAA CAGGACCATG TACAAATGTC AGCACAGTAC AATGTACACA 6960
TGGAATCAGG CCAGTAGTAT CAACTCAACT GCTGTTAAAT GGCAGTCTAG CAGAAGAAGA 7020
TGTAGTAATT AGATCTGCCA ATTTCACAGA CAATGCTAAA ACCATAATAG TACAGCTGAA 7080
CACATCTGTA GAAATTAATT GTACAAGACC CAACAACAAT ACAAGAAAAA GTATCCGTAT 7140
CCAGAGGGGA CCAGGGAGAG CATTTGTTAC AATAGGAAAA ATAGGAAATA TGAGACAAGC 7200
ACATTGTAAC ATTAGTAGAG CAAAATGGAA TGCCACTTTA AAACAGATAG CTAGCAAATT 7260
AAGAGAACAA TTTGGAAATA ATAAAACAAT AATCTTTAAG CAATCCTCAG GAGGGGACCC 7320
AGAAATTGTA ACGCACAGTT TTAATTGTGG AGGGGAATTT TTCTACTGTA ATTCAACACA 7380
ACTGTTTAAT AGTACTTGGT TTAATAGTAC TTGGAGTACT GAAGGGTCAA ATAACACTGA 7440
AGGAAGTGAC ACAATCACAC TCCCATGCAG AATAAAACAA TTTATAAACA TGTGGCAGGA 7500
AGTAGGAAAA GCAATGTATG CCCCTCCCAT CAGTGGACAA ATTAGATGTT CATCAAATAT 7560
```

FIG. 3D

```
TACTGGGCTG CTATTAACAA GAGATGGTGG TAATAACAAC AATGGGTCCG AGATCTTCAG  7620
ACCTGGAGGA GGCGATATGA GGGACAATTG GAGAAGTGAA TTATATAAAT ATAAGTAGT   7680
AAAAATTGAA CCATTAGGAG TAGCACCCAC CAAGGCAAAG AGAAGAGTGG TGCAGAGAGA  7740
AAAAAGAGCA GTGGGAATAG GAGCTTTGTT CCTTGGGTTC TTGGGAGCAG CAGGAAGCAC  7800
TATGGGCTGC ACGTCAATGA CGCTGACGGT ACAGGCCAGA CAATTATTGT CTGATATAGT  7860
GCAGCAGCAG AACAATTTGC TGAGGGCTAT TGAGGCGCAA CAGCATCTGT TGCAACTCAC  7920
AGTCTGGGGC ATCAAACAGC TCCAGGCAAG AATCCTGGCT GTGGAAAGAT ACCTAAAGGA  7980
TCAACAGCTC CTGGGGATTT GGGGTTGCTC TGGAAAACTC ATTTGCACCA CTGCTGTGCC  8040
TTGGAATGCT AGTTGGAGTA ATAAATCTCT GGAACAGATT TGGAATAACA TGACCTGGAT  8100
GGAGTGGGAC AGAGAAATTA ACAATTACAC AAGCTTAATA CACTCCTTAA TTGAAGAATC  8160
GCAAAACCAG CAAGAAAAGA ATGAACAAGA ATTATTGGAA TTAGATAAAT GGGCAAGTTT  8220
GTGGAATTGG TTTAACATAA CAAATTGGCT GTGGTATATA AAATTATTCA TAATGATAGT  8280
AGGAGGCTTG GTAGGTTTAA GAATAGTTTT TGCTGTACTT TCTATAGTGA ATAGAGTTAG  8340
GCAGGGATAT TCACCATTAT CGTTTCAGAC CCACCTCCCA ATCCCGAGGG GACCCGACAG  8400
GCCCGAAGGA ATAGAAGAAG AAGGTGGAGA GAGAGACAGA GACAGATCCA TTCGATTAGT  8460
GAACGGATCC TTAGCACTTA TCTGGGACGA TCTGCGGAGC CTGTGCCTCT TCAGCTACCA  8520
CCGCTTGAGA GACTTACTCT TGATTGTAAC GAGGATTGTG GAACTTCTGG GACGCAGGGG  8580
GTGGGAAGCC CTCAAATATT GGTGGAATCT CCTACAGTAT TGGAGTCAGG AACTAAAGAA  8640
TAGTGCTGTT AACTTGCTCA ATGCCACAGC CATAGCAGTA GCTGAGGGGA CAGATAGGGT  8700
TATAGAAGTA TTACAAGCAG CTTATAGAGC TATTCGCCAC ATACCTAGAA GAATAAGACA  8760
GGGCTTGGAA AGGATTTTGC TATAAGATGG GTGGCAAGTG GTCAAAAAGT AGTGTGATTG  8820
GATGGCCTGC TGTAAGGGAA AGAATGAGAC GAGCTGAGCC AGCAGCAGAT GGGGTGGGAG  8880
CAGTATCTCG AGACCTAGAA AAACATGGAG CAATCACAAG TAGCAATACA GCAGCTAACA  8940
ATGCTGCTTG TGCCTGGCTA GAAGCACAAG AGGAGGAAGA GGTGGGTTTT CCAGTCACAC  9000
CTCAGGTACC TTTAAGACCA ATGACTTACA AGGCAGCTGT AGATCTTAGC CACTTTTTAA  9060
AAGAAAAGGG GGGACTGGAA GGGCTAATTC ACTCCCAAAG AAGACAAGAT ATCCTTGATC  9120
TGTGGATCTA CCACACACAA GGCTACTTCC CTGATTGGCA GAACTACACA CCAGGGCCAG  9180
GGGTCAGATA TCCACTGACC TTTGGATGGT GCTACAAGCT AGTACCAGTT GAGCCAGATA  9240
AGGTAGAAGA GGCCAATAAA GGAGAGAACA CCAGCTTGTT ACACCCTGTG AGCCTGCATG  9300
GAATGGATGA CCCTGAGAGA GAAGTGTTAG AGTGGAGGTT TGACAGCCGC CTAGCATTTC  9360
ATCACGTGGC CCGAGAGCTG CATCCGGAGT ACTTCAAGAA CTGCTGACAT CGAGCTTGCT  9420
ACAAGGGACT TTCCGCTGGG GACTTTCCAG GGAGGCGTGG CCTGGGCGGG ACTGGGGAGT  9480
GGCGAGCCCT CAGATGCTGC ATATAAGCAG CTGCTTTTTG CCTGTACTGG GTCTCTCTGG  9540
TTAGACCAGA TCTGAGCCTG GGAGCTCTCT GGCTAACTAG GAACCCACT GCTTAAGCCT  9600
CAATAAAGCT TGCCTTGAGT GCTTCAAGTA GTGTGTGCCC GTCTGTTGTG TGACTCTGGT  9660
AACTAGAGAT CCCTCAGACC CTTTTAGTCA GTGTGGAAAA TCTCTAGCA              9709
```

FIG. 3E

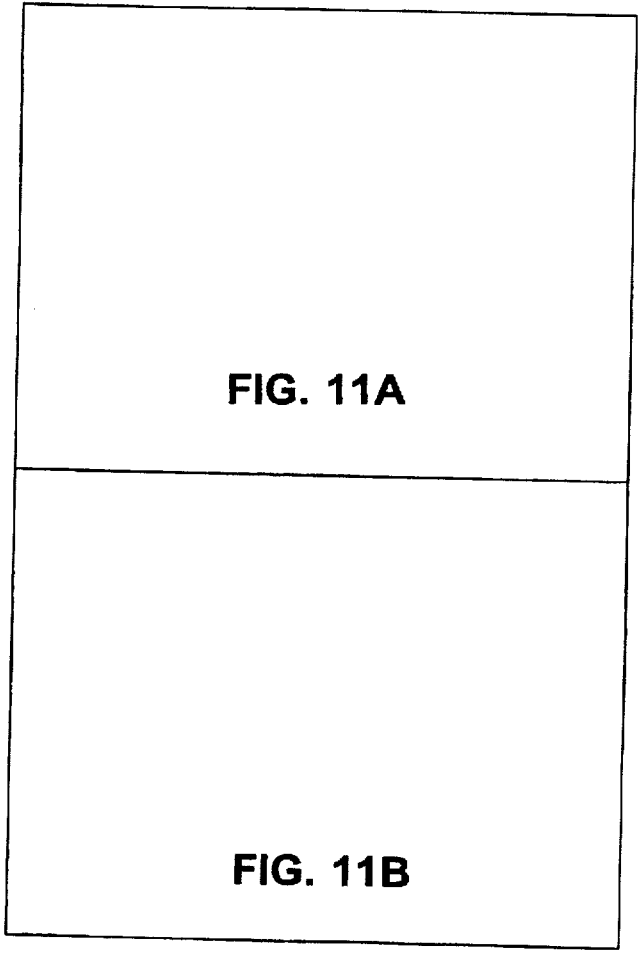
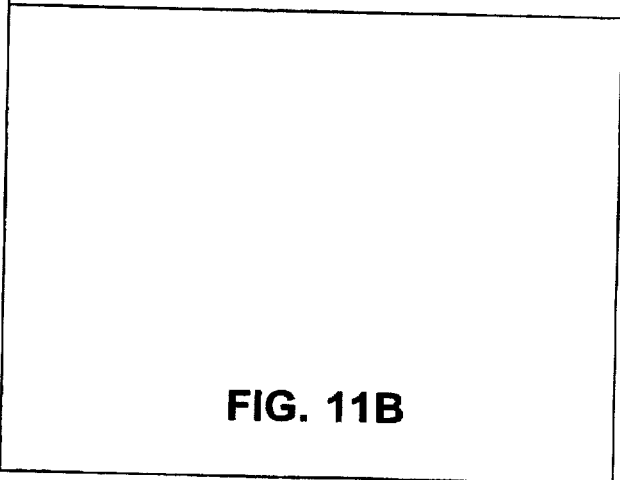
FIG. 11

PRIMATE LENTIVIRUS ANTIGENIC COMPOSITIONS

CROSS REFERENCE TO RELATED APPLICATIONS

This application is a continuation-in-part of U.S. Ser. No. 07/727,494 filed on Jul. 9, 1991 now abandoned, which is in turn, a continuation-in-part of 07/551,945, filed Jul. 12, 1990 now abandoned.

STATEMENT TO FEDERALLY SPONSORED RESEARCH

This invention was supported under NIH Grant Number AI-25328 and RR00168. The U.S. Government has certain rights to the invention.

This invention is in the general field of primate lentiviruses and their utilization as protective vaccines.

Human immunodeficiency virus type 1 (HIV-1), a member of the lentivirus subfamily of retroviruses, is the etiologic agent of the disease, acquired immune deficiency syndrome (AIDS) (F. Barre-Sinoussi et al., *Science* 220:868, 1983, R. C. Gallo et al., *Science* 224:500, 1984). This virus suppresses the immune system rendering the host highly susceptible to a variety of opportunistic infections and neoplasms. The AIDS epidemic is worldwide, with thousands of Europeans and possibly millions of Africans infected with the virus (T. C. Quinn et al., *Science* 234:955, 1986). As of December 1987, there were 47,000 cases of AIDS in the United States, and it was estimated that an additional 1 to 2 million individuals were infected but, at that time, asymptomatic (U.S. Public Health Service, *Public Health Rep.* 101:341, 1986). HIV infection is spread by sexual contact, by infected blood or blood products, and perinatally from mother to infant (A. S. Fauci et al., *Ann. Intern. Med.* 100:92, 1984; J. W. Curran et al., *Science* 229:1352, 1985).

A closely related but distinct virus, human immunodeficiency virus type 2 (HIV-2) has been isolated from patients with a clinical syndrome comparable to HIV-1-induced AIDS. HIV-2 shares a significant degree of sequence homology and serologic reactivity with HIV-1 (F. Clavel, *N. Eng. J. of Med.* 316:1180, 1987).

B. Hahn et al. (*Nature* 312:166, 1984) and G. M. Shaw et al. (*Science* 226:1165, 1984) report the isolation of HIV1 DNA clones capable of transmitting infection to cultured cells. L. Ratner et al. (*Nature* 313:277, 1985,) and S. Wain-Hobson et al. (*Cell* 40:9, 1985) report the complete nucleotide sequence of HIV-1.

The HIV-1 genome contains at least nine open reading frames. As catalogued by Cullen and W. C. Green (*Cell* 58:423, 1989), these encode structural proteins (Gag, Pol, Env), proteins required for virion morphogenesis and maturation (vif, vpu), nonstructural, regulatory proteins (Tat, Rev, Nef), and a protein of unknown function (vpr).

Simian immunodeficiency viruses (SIVs) are nonhuman primate lentiviruses that are the closest known relatives of HIV-1 and HIV-2. They closely parallel their human counterparts in genetic organization and biological properties. Similarities between HIV and SIV include lentiviral morphology; tropism for CD4 lymphocytes and macrophages; extra genes called tat, rev, vif, vpf, and nef generally not present in other retroviruses; interaction with the CD4 receptor on host cells; cytopathicity; and the ability, of at least some, to cause chronic disease and death after long-term persistent infection (R.C. Desrosiers, *Annu. Rev. Microbiol.* 42:607, 1988).

SIV molecular clones have been isolated from macaque monkeys, although other species such as mangabeys may be their natural host, and are generally designated SIVmac (L. Chakrabarti et al., *Nature* 328:543, 1987, V. Hirsch et al., *Cell* 49:307, 1987, G. Franchini et al., *Nature* 328:539, 1987). One clone, chosen for its ability to grow well in macaque peripheral blood lymphocytes, has been designated SIVmac239. (Y. M. Naidu et al., *J. Virol.* 62:4691, 1988). Rhesus monkeys inoculated with stock virus derived from cloned SIVmac239 DNA develop an AIDS-like disease and eventually die from the infection (H. Kestler et al., *Science* 248:1107, 1990).

To date, efforts at provoking a protective immune response against HIV have generally focused on specific antigens, such as HIV-encoded proteins. The sera of patients infected with HIV-1 contain antibodies that recognize the precursor and processed forms of the viral envelope (env) gene product, gp120 (J. S. Allan et al., *Science* 228:1091, 1985, F. Barin et al., *Science* 228:1094, 1985). These antibodies reportedly are not sufficient to impart immunity against AIDS, at least in the vast majority of infected individuals (J. Schupbach et al., *Science* 224:503, 1984, M. Essex et al., *Science* 220:859, 1983, Barre-Sinoussi et al., *Science* 220:868, 1983). However, various Env-based vaccines are currently being studied (see, for example, D. Zagury et al., *Nature* 332:728, 1988, W. C. Koff and A. S. Fauci, *AIDS* 1989 3 (suppl): S125, 1989).

A killed, non-infectious, envelope-depleted whole HIV-1 virus is also being tested in patients already infected with HIV-1 (A. Levine et al., *Fifth International Conference on AIDS. The Scientific and Social Challenge.*, p. 219, 1989)

D. Baltimore (*Nature* 335:395, 1988) reports a proposed procedure for introducing, into a human subject, bone-marrow stem cells that are "infected or transfected with a virus or DNA construct that encodes an RNA or protein able dominantly to interfere with the intracellular growth of HIV, and propose that it be called intracellular immunization".

M. H. Malim et al. (*Cell* 58:205, 1989) report the isolation of a Rev mutant that trans-dominantly inhibits wild-type Rev function and inhibits HIV-1 replication and say that trans-dominant Rev protein may be useful as a means of providing "intracellular immunization against HIV-1".

D. Trono et al. (*Cell* 59:113, 1989) report that replication of wild-type HIV-1 virus is inhibited by co-expression of dominant negative Gag protein and say that these mutant proteins "appear to constitute suitable substrates for developing an antiviral scheme based on intracellular immunization".

M. Green et al. (*Cell* 58:215, 1989) report that defective Tat peptides block trans-activation of the HIV-1 LTR and say that their "results suggest an attractive approach for the development of an AIDS therapy".

SUMMARY OF THE INVENTION

The invention features a vaccine which evokes protection against AIDS and associated diseases including purified primate lentivirus, or a DNA clone thereof, in a pharmaceutically acceptable carrier. Such a DNA clone harbors a non-revertible null mutation of the nef gene and may also include a non-revertible null mutation in one or more non-essential genetic elements such as NRE, vif, vpr, vpx and/or vpu, nuclear factor κB (NFκB)-binding element, or Sp1 binding element. Furthermore, vaccines according to the invention can include deletions of non-essential elements in other HIV genes which attenuate but preserve the replication competency of the primate lentivirus, e.g., deletions in portions of gp41, gag, and pol. Further, the invention features a method for administering an immunizing amount of the vaccine to a patient (i.e., a host for the live pathogenic virus).

The vaccine of the present invention and methods of vaccination provide immunological protection against primate lentiviruses using a live and infectious, but nonpathogenic, derivative of the parent virus. The introduction of non-revertible mutations provides an advantage over methods previously employed to produce attenuated viral vaccines, for example, isolation of viral stocks harboring genomic point mutation(s), capable of reverting to the wild-type sequence. In addition, construction of the engineered viral DNA clone is rapid, and the method of producing the vaccine by propagation of attenuated virus in mammalian cell culture is both rapid and inexpensive.

In one aspect, the invention features a method of producing such a vaccine by transfecting cultured primate cells with a primate lentiviral nucleic acid according to the invention (i.e., one which contains an engineered non-revertible null mutation of the nef gene and which may also contain a non-revertible null mutation in the NRE, vpr, vpx, and/or vpu sequences), isolating lentivirus whose genome contains the mutation of the nef gene, and compounding the virus into a pharmaceutically acceptable vaccine.

In another aspect, the invention features a DNA clone of an infectious nonpathogenic primate lentivirus (PLV) genome harboring a non-revertible null mutation of the nef gene. By "primate lentivirus genome" is meant the genetic material derived from a retrovirus, that, in wild-type form, (a) includes tat, rev, and nef genes, (b) is capable of infecting T4 cells of a primate host, and (c) possesses a viral morphogenesis and morphology characteristic of the lentivirus subfamily. The term includes, without limitation, all variants of HIV and SIV, including HTLV-III, ARV, LAV, HIV-1, HIV-2, SIVmac, SIVagm, SIVmnd, SIVsmm, SIVman, SIVmand, and SIVcpz. By "null mutation" is meant an alteration in the nucleotide sequence that renders the gene incapable of expressing a functional protein product. By "non-revertible" is meant unable to regain the ability to produce a functional protein product in the absence of wild-type virus or intentional genetic manipulation.

Preferred clones according to this invention are derived from isolated primate lentiviruses, for example, they are produced by modifying a naturally occurring isolate to create the required nef mutation or by synthesizing nucleic acid to generally correspond to the sequence of a naturally occurring isolate, but with the required nef mutation. Thus, this invention is not limited to any specific viral clone. Those of ordinary skill in the art can readily isolate or engineer equivalent DNA clones which may differ in nucleic acid sequence by conservative substitutions such that the altered codon encodes a very similar amino acid, for example, a substitution of an alanine codon for a glycine codon. In addition, the nucleic acid sequence may have one or more non-conservative codon substitutions or one or more deletions which do not destroy the ability of the virus to produce progeny virus. Such equivalent DNA clones may be engineered by standard techniques of recombinant DNA technology, e.g., random or site-specific in vitro mutagenesis or deletion of sequences between restriction sites, and isolated by standard techniques of recombinant DNA technology including, but not limited to, the use of PCR and lambda, plasmid, cosmid, and/or other cloning vectors. Further, the invention is not limited to the specific non-revertible null mutation of the nef gene provided in the drawing; those skilled in the art can readily isolate other mutations which interfere with the ability of the nef gene to produce a functional protein product and which are non-revertible, e. g., larger or smaller deletions of the nef gene sequence. Such equivalent mutations may be engineered or isolated by standard techniques of recombinant DNA technology, e.g., by in vitro mutagenesis.

In a related aspect, the invention features a primate lentivirus (i.e., an RNA clone or virally packaged RNA) whose genome contains an engineered (i.e., intentionally created or intentionally selected and isolated) non-revertible, null mutation in the nef gene. Such a virus is infectious but not pathogenic, and it may be readily isolated by transfecting cultured primate cells with one of the DNA clones described above and harvesting progeny virus.

In preferred embodiments of both aspects, the nucleic acid sequence of the DNA clone of the primate lentivirus is derived from a primate lentivirus, specifically HIV or SIV, particularly SIVmac, and the mutation leaves intact the env gene sequence corresponding to the extracellular portion of the gene product.

In other preferred embodiments, the nucleic acid sequence of the DNA clone of the primate lentivirus includes, in addition to a nef mutation (as described above), a non-revertible null mutation in one or more of the following sequences: Negative Regulatory Element (NRE or US), vif, vpr, vpx (in the case of a simian lentivirus) or vpu (in the case of a human lentivirus), NFκB-binding element, or Sp1 binding element. Preferred embodiments include SIVΔ3 and HIV-1Δ3 which also comprise additional mutations in non-essential genetic elements of the primate lentivirus. Particularly preferred DNA clones according to the invention include SIVmac239ΔnefΔNRE, SIVmac239Δ3, SIVmac239Δ4, HIV-1ΔnefΔNRE, HIV-1Δ3, and HIV-1Δ4.

Other features and advantages of the invention will be apparent from the following description of the preferred embodiments and from the claims. For example, vaccines which are not deleted in nef but are mutated in one of the ways described above so as to retain replication competency yet be substantially attenuated may be included in yet other aspects of the invention.

DESCRIPTION OF THE PREFERRED EMBODIMENTS

The drawings will first be described.

BREIF DESCRIPTION OF DRAWINGS

FIGS. 1A–1V depict the complete nucleic acid and amino acid sequence of the SIVmac239 genome, one example of a primate lentivirus useful in this invention. The boundaries of the nef open reading frame and the extent of the nef deletion in the mutant clone, pSIVmac239 nef-deletion, are shown. FIG. 1 is a instructional drawing showing the order of the sequences shown in FIGS. 1A–1V.

FIGS. 2A–2R depict the complete nucleic acid and amino acid sequence of an isolate of HIV-1. The nef open reading frame is denoted E', and its boundaries are shown. FIG. 2 is a instructional drawing showing the order of the sequences shown in FIGS. 2A–2R.

FIGS. 3A–3J (SEQ ID NO:5) represent the complete nucleic acid sequence of HIV NL43.

Figure 5A:
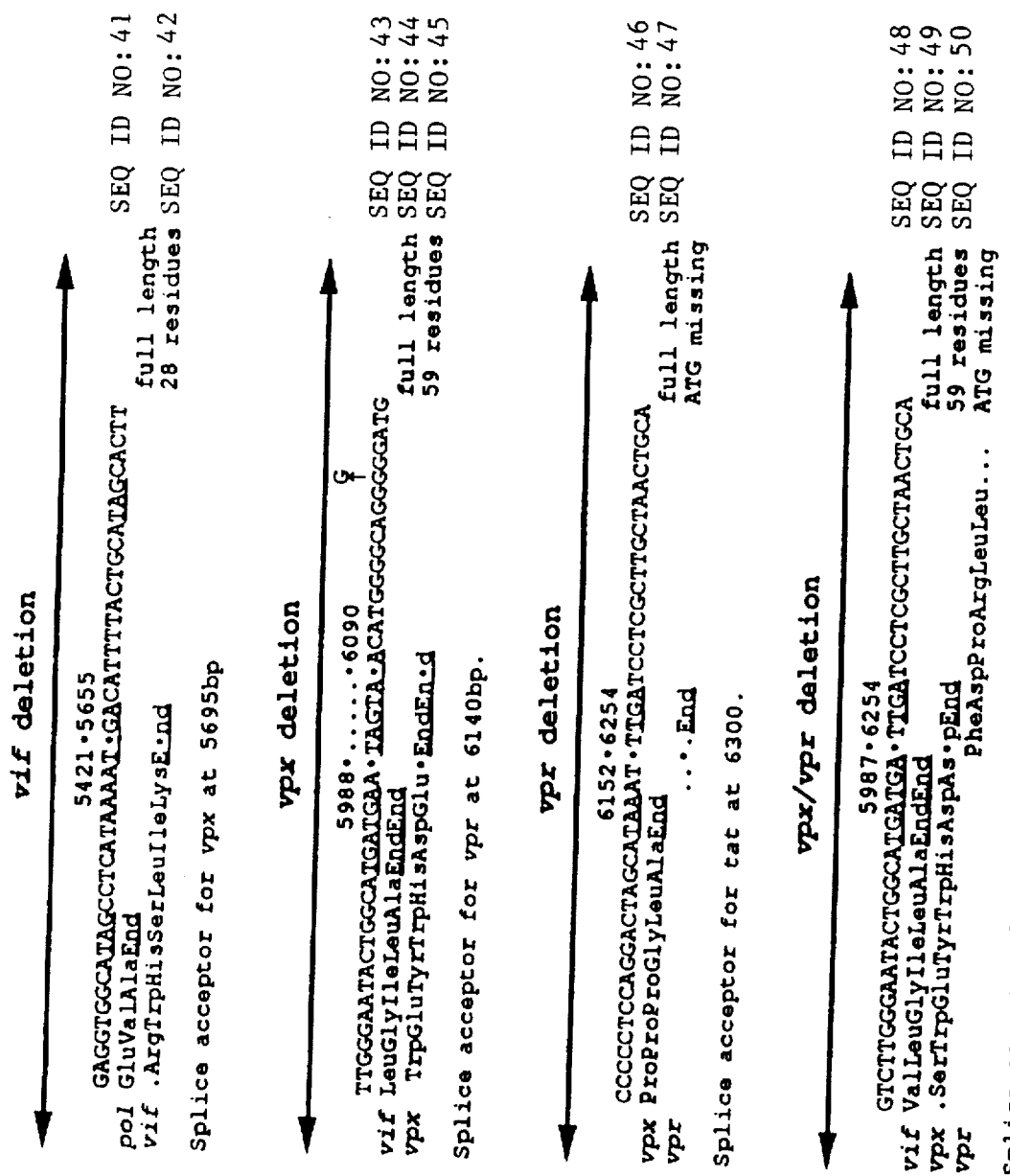
Figure 5B:
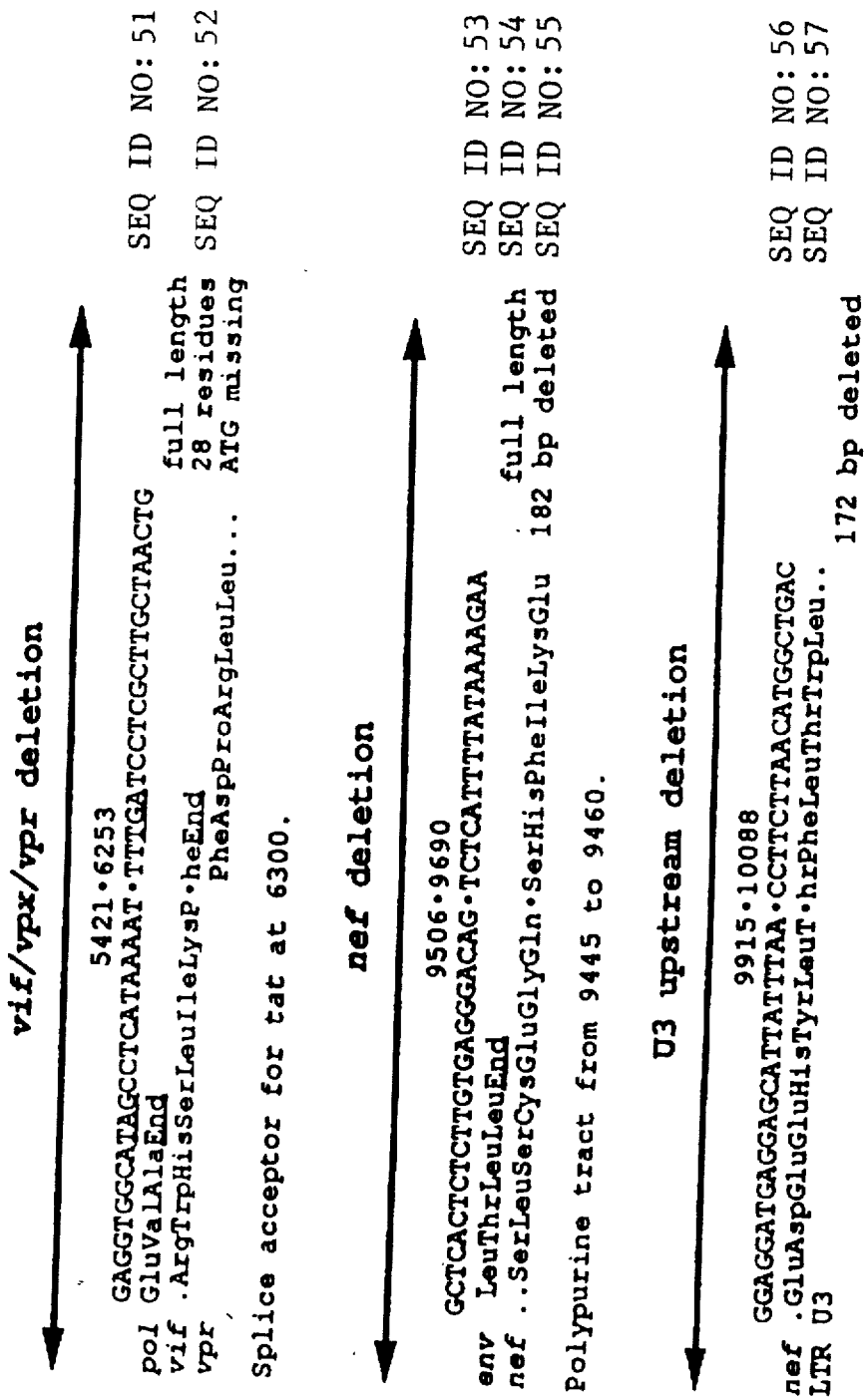

FIGS. 5A and 5B are a diagram showing sequences of deletion mutants. The upper five deletion mutations were constructed in plasmids containing the left half of the SIVmac239 genome. The bottom two deletions were constructed in plasmids containing the right half of SIVmac239. Numbers refer to nucleotides adjacent to deleted sequences and are based on the numbering system of Regier and Desrosiers(*AIDS Res. Hum. Retroviruses*, 6:1221–1231, 1990). Locations of relevant nearby sites are denoted under the predicted translated sequences for each deletion. The predicted sizes of residual polypeptides, sizes of deletions and other appropriate comments are indicated to the right. A sixth left half deletion mutation, ΔvifΔvpr, which contains two separate deletions has deletion limits identical to those of the individual vif and vpr deletions. All mutants containing deletions of the U3 upstream region had the additional nef deletion spanning nucleotides 9251 to 9432.

Figure 6A:
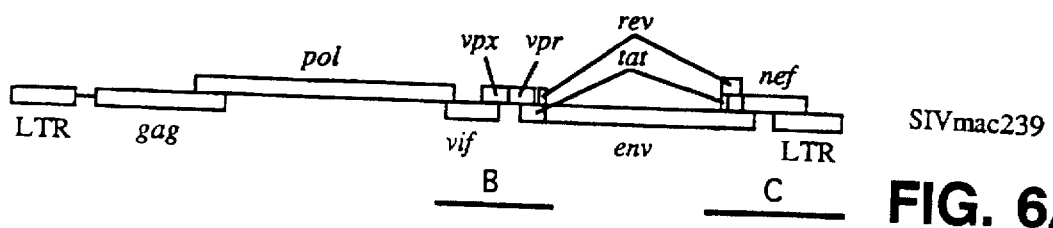
Figure 6B:
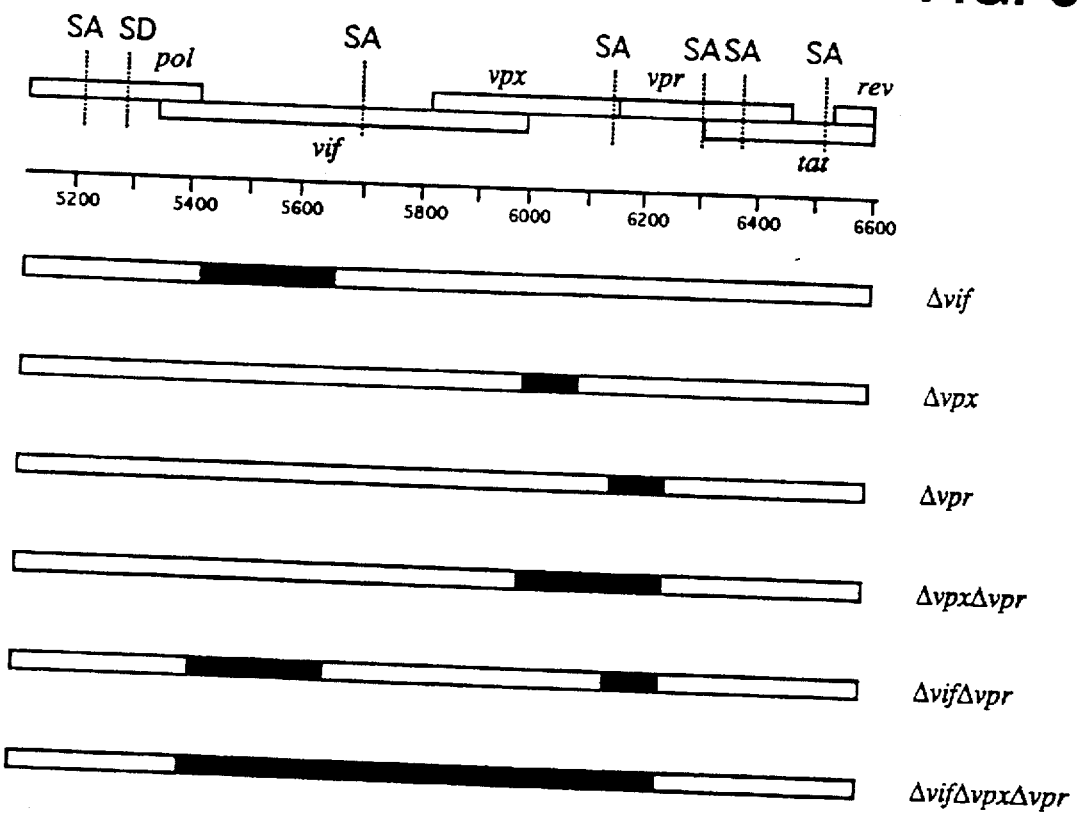
Figure 6C:
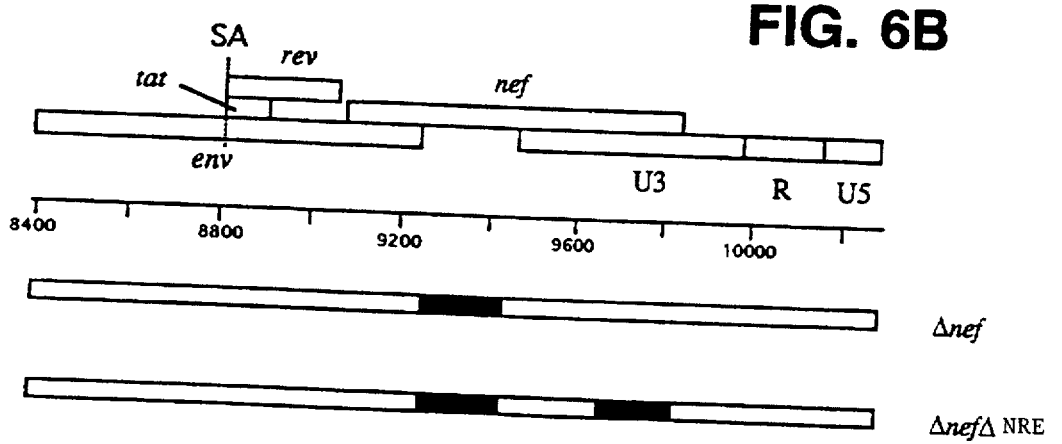

FIGS. 6A–6C are diagrams showing the location of deletions in the SIV genome. FIG. 6A: Genetic organization of wild-type SIVmac239 showing translated sequences in the three forward reading frames as open rectangles. p239SpSp5' contains sequences from the left LTR to almost the end of vpr. p239SpR3' contains sequences from near the end of vpr to the right LTR. The two horizontal bars under the map refer to sequences expanded in panels B and C below. FIG. 6B: Enlargement of the central region "nonessential" genes of SIVmac239 drawn to scale. The pol, vif, vpx, and vpr genes and the first exons of tat and rev are shown. Splice acceptor sites (SA), are at nucleotides 5211, 5694, 6139, 6299, 6371, and 6512. A splice donor site (SD), is located at nucleotide 5284. Shaded boxes represent deleted sequences. FIG. 6C: Enlargement of the genomic organization of the 3'-terminal portion of SIVmac239 drawn to scale. The env and nef genes, the second exons of tat and rev, and the U3, R and U5 regions of the right LTR are shown. Two splice acceptor sites (single line) are located at nucleotides 8802 and 8805. Shaded portions represent deleted sequences.

Figure 7:
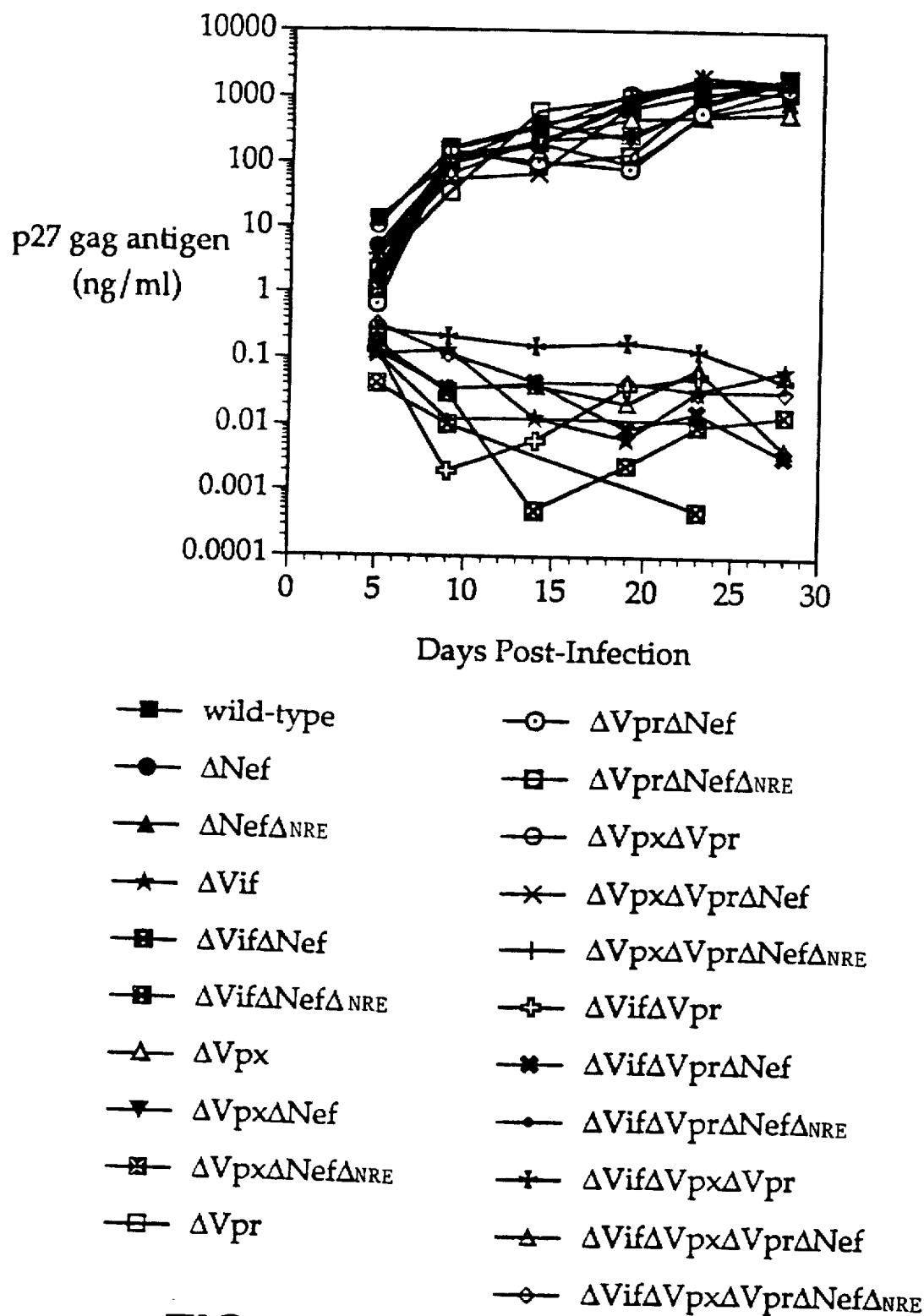

FIG. 7 is a line graph showing replication of deletion mutant and wild-type SIV in CEMx174 cells. Duplicate wells of CEMx174 cells were infected with an amount of virus stock equivalent to 0.2 ng p27 gag antigen. Stocks were derived from transient expression in COS-1 fibroblasts. All infections were done on the same date. Virus production was measured on the days indicated by p27 gag antigen capture analysis. Results are the average of duplicates.

Figure 8:
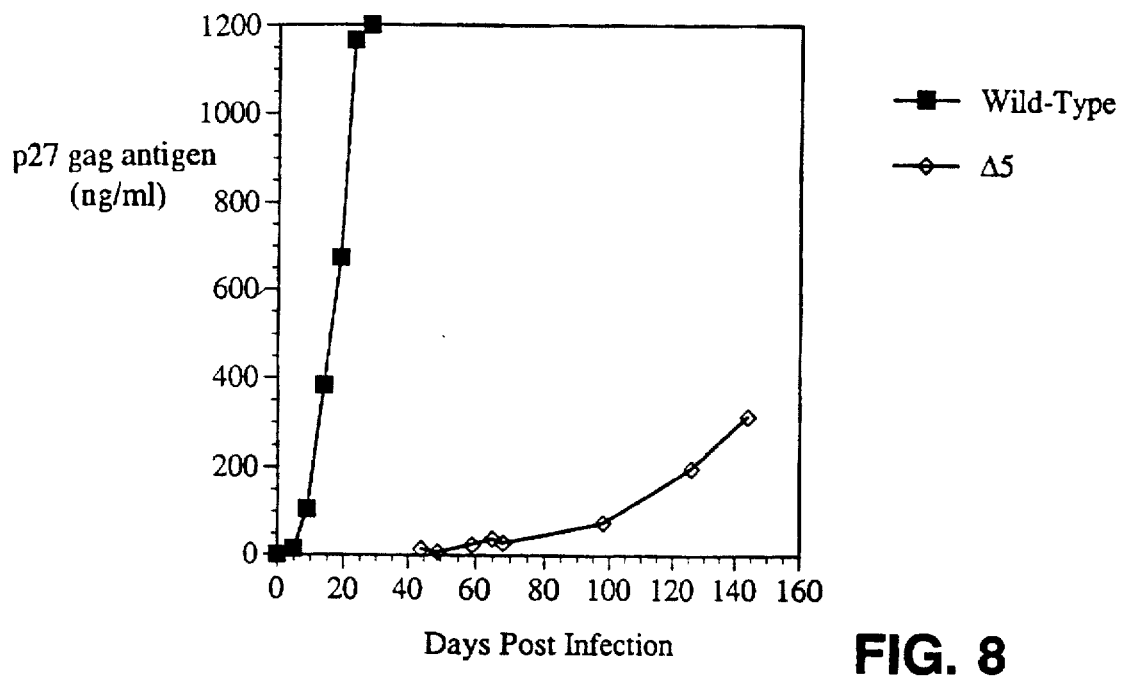

FIG. 8 is a line graph showing replication of Δ5 and wild-type SIV in CEMx174 cells. T-25 canted-neck tissue culture flasks of freshly passaged CEMx174 cells were infected with an amount of virus stock containing 655 ng p27 gag antigen for Δ5 virus or long p27 gag antigen for wild-type virus. The Δ5 virus stock was produced by harvesting supernatant 47 days after infection of CEMx174 cells. The wild-type virus stocks were prepared from the supernatant medium of CEMx174 cells 7–14 days post-transfection. Virus production was measured on the days indicated by p27 gag antigen capture analysis. Replication of wild-type virus was not measured beyond day 28 post-infection.

Figure 9:
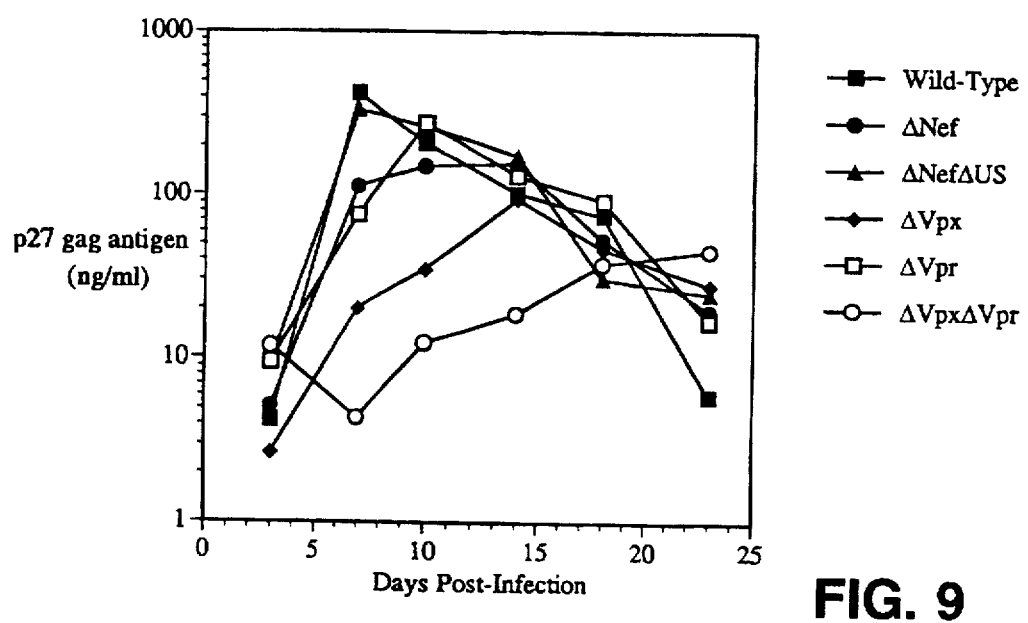

FIG. 9 is a line graph showing replication of deletion mutant and wild-type SIV in rhesus monkey PBMC cultures. Duplicate wells of PBMCs previously activated with phytohemagglutinin (PHA) and growing in interleukin-2 (IL-2) were infected with an amount of virus stock equivalent to 4 ng p27 gag antigen. Stocks were prepared from the supernatant medium of infected CEMx174 cells 7–14 days post-infection. All infections were done on the same date. Virus production was measured on the days indicated by p27 gag antigen capture analysis. Results are the average of duplicates.

Figure 10:
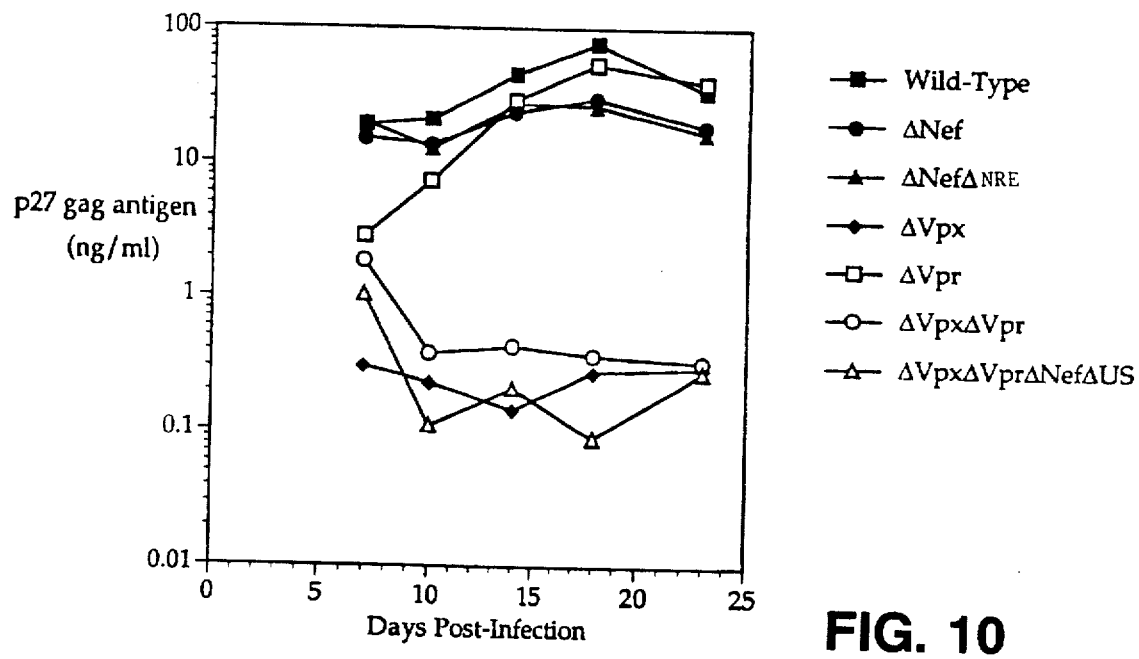

FIG. 10 is a line graph showing replication of deletion mutant and wild-type SIV in rhesus monkey alveolar macrophage cultures. Duplicate wells of macrophages in GM-CSF for 24 hrs were infected with an amount of virus stock equivalent to 4 ng p27 gag antigen. Stocks were prepared from the supernatant medium of infected CEMx174 cells 7–14 days post-infection. All infections were done on the same date. Virus production was measured on the days indicated by p27 antigen capture analysis. Results are the average of duplicates.

Figure 11A:
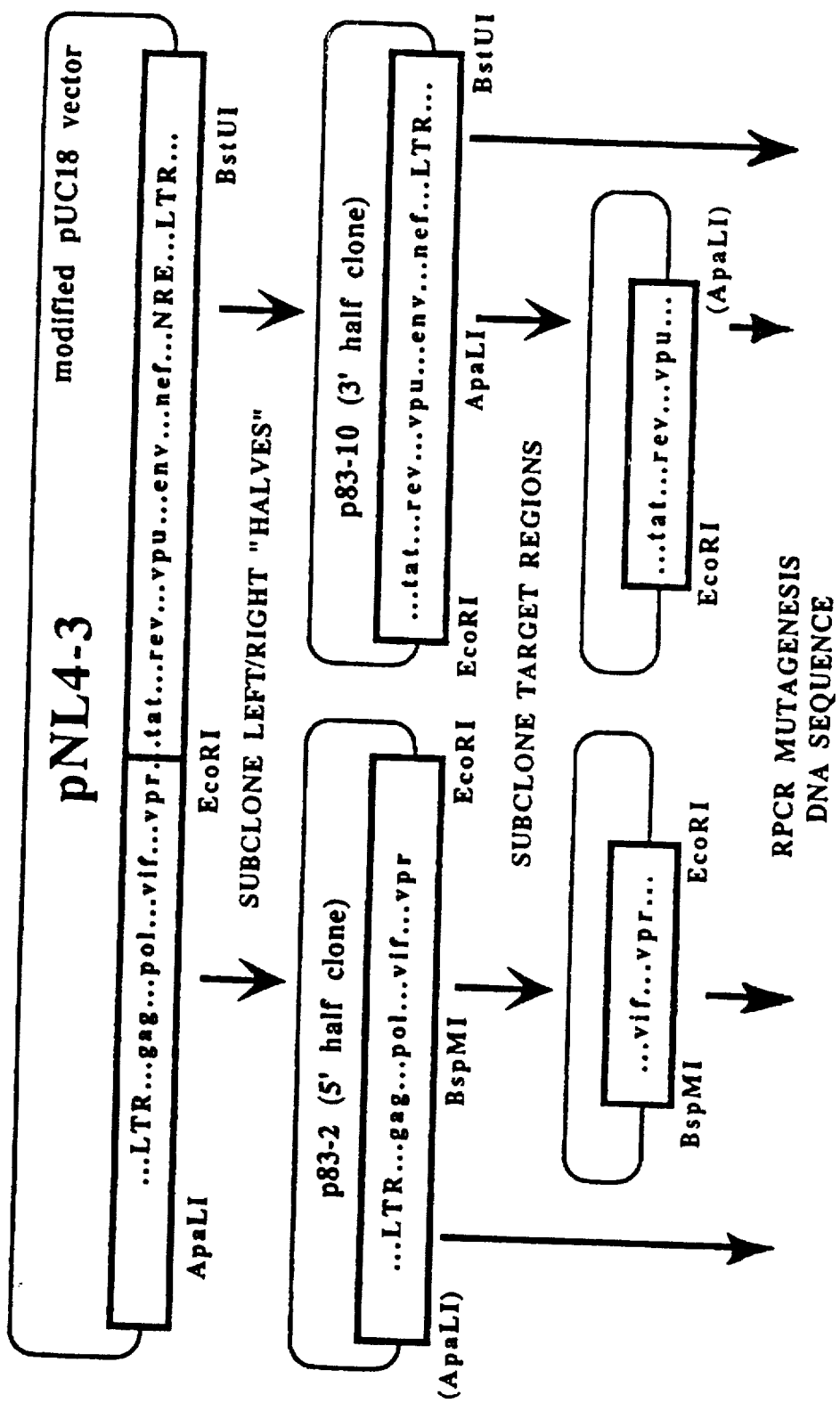
Figure 11B:
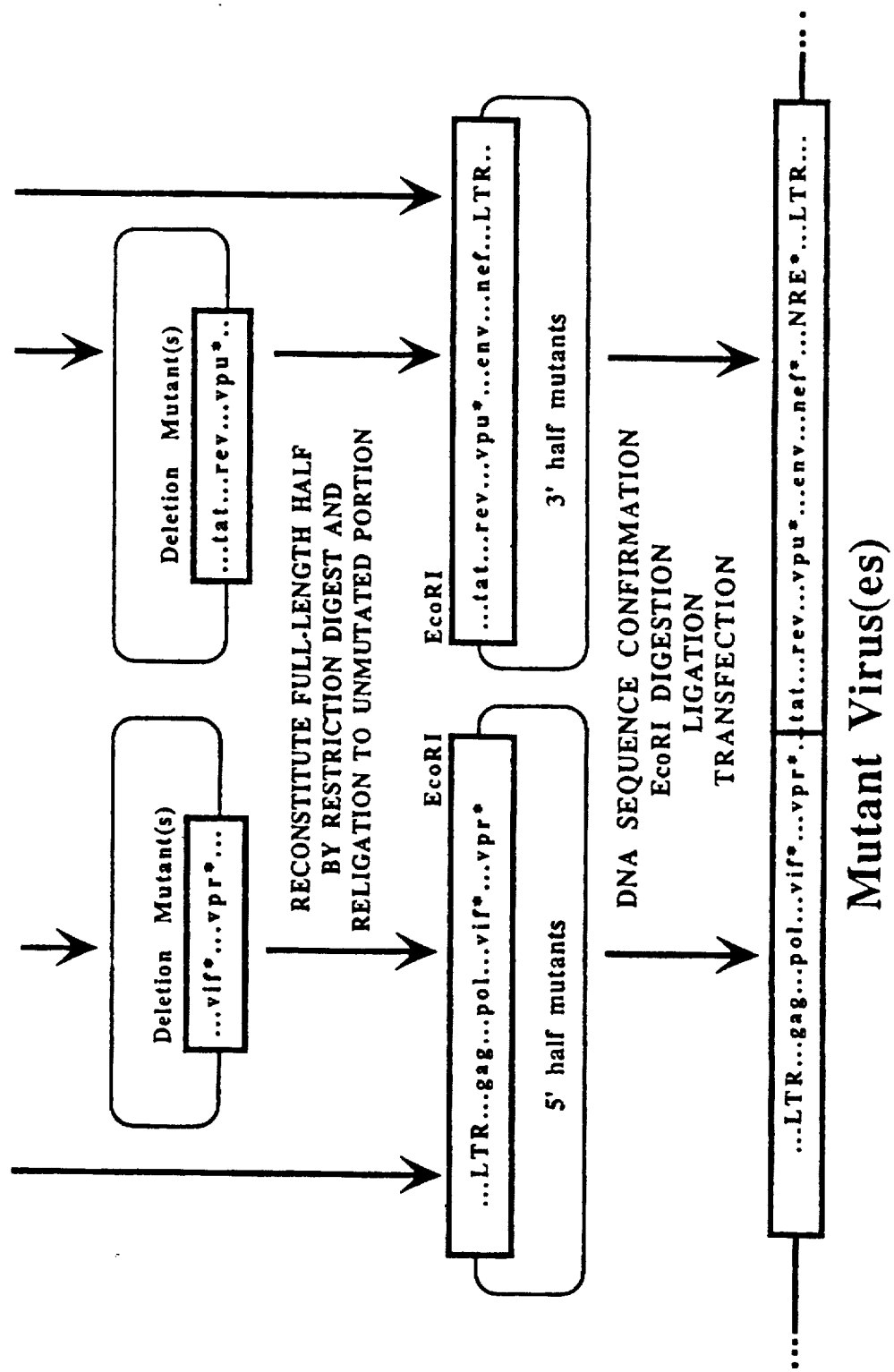

FIG. 11 is an instructional drawing showing the sequence of steps in FIGS. 11A and 11B, which are diagrams of the strategy for construction of plasmids containing HIV deletion mutations. HIV-1 strain NL4-3 was subcloned into two plasmids, containing the 5'- and 3'-halves of the genome. Target areas were further subcloned and mutagenized by recombinant PCR. Mutagenized plasmids were verified by DNA sequence analysis, reconstituted to full-length plasmids and used to generate mutant virus, as described in Materials and Methods.

Figure 12A:
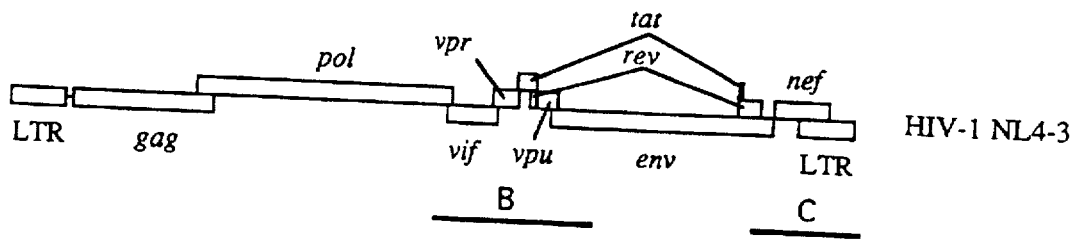
Figure 12B:
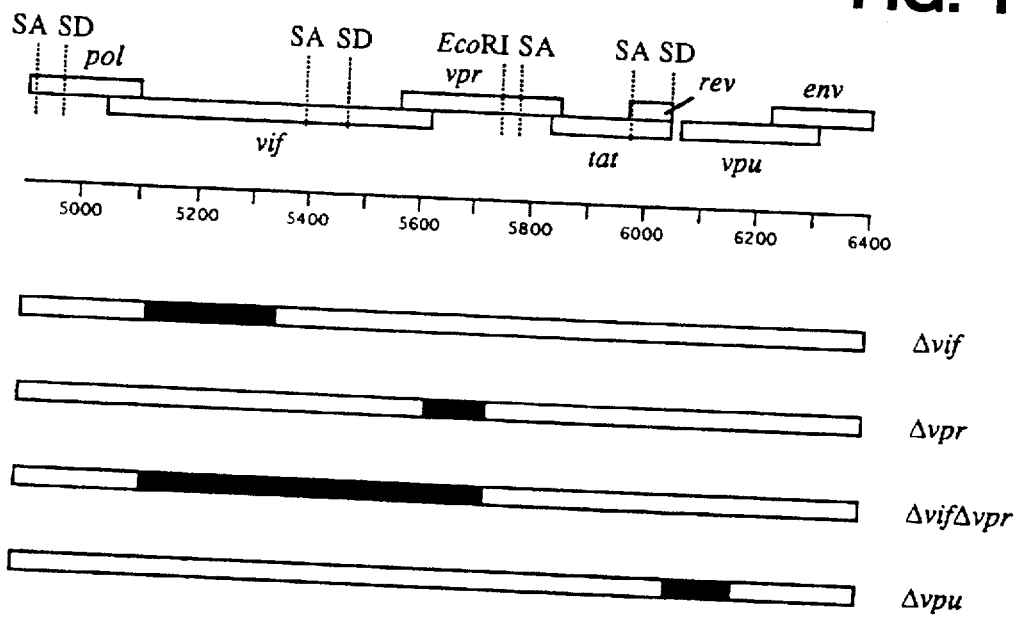
Figure 12C:
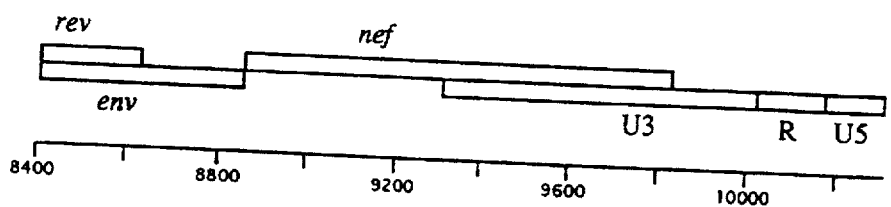

FIGS. 12A–12C are diagrams showing the location of deletions in HIV-1 genome. FIG. 12A: Genetic organization of wild-type HIV-1 strain NL4-3 showing translated sequences in the three forward reading frames (open rectangles). p83-2 contains sequences from the 5'-LTR to the EcoRI site in the middle of vpr. p83-10 contains sequences from the EcoRI site to the 3'-LTR. The two horizontal bars below the map are sequences expanded in FIG. 12B and FIG. 12C below. FIG. 12B: Enlargement of the central region "nonessential" genes of HIV-1 strain NL4-3 (drawn to scale). The pol, vif, vpr, vpu, and env genes and the first expressed exons of tat and rev are shown. Shaded boxes represent deleted sequences. SA and SD denote predicted splice acceptor and donor sites[25-29]. FIG. 12C: Enlargement of the genomic organization of the 3'-terminal portion of HIV-1 strain NL4-3 (drawn to scale). The env and nef genes, the second exon of rev, and the U3, R and U5 regions of the 3'-LTR are shown. Shaded portions represent deleted sequences.

Figure 13:
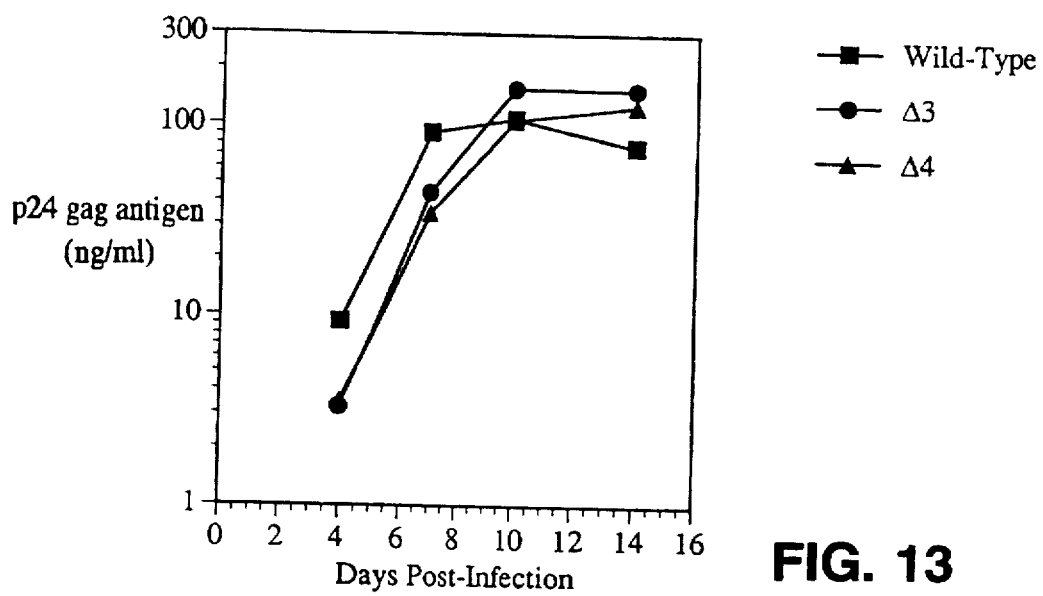

FIG. 13 is a line graph showing the replication of mutant and wild-type HIV in PBMC from a single chimpanzee. PBMC cultures previously activated with phytohemagglutinin (PHA) and growing in interleukin-2 (IL-2) were infected with an amount of virus stock equivalent to 40 ng p24 gag antigen. Virus production was measured on the days indicated by antigen capture analysis. Results are the average of duplicates.

Figure 14:
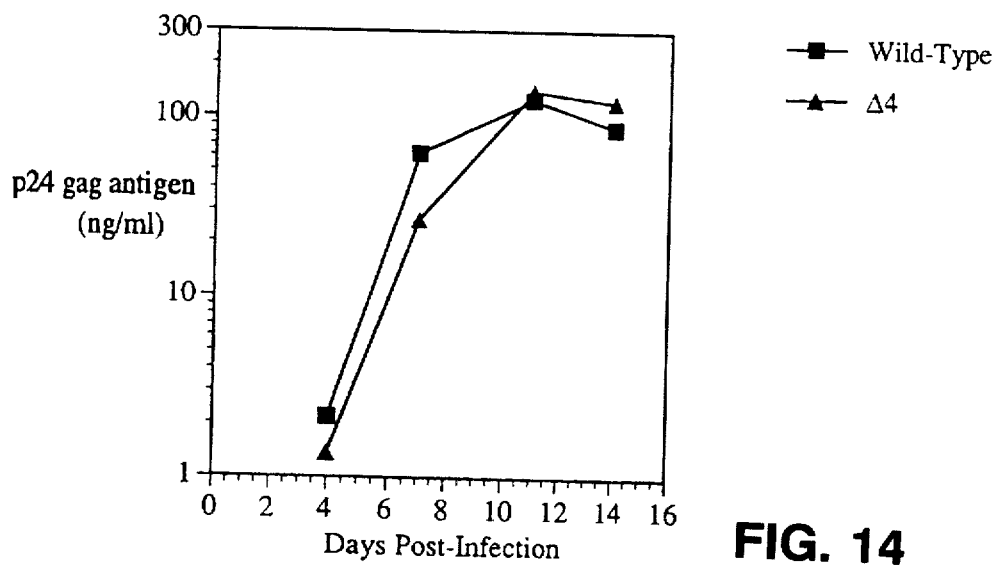

FIG. 14 is a line graph showing the replication of mutant Δ4 and wild-type HIV in chimpanzee PBMC. PBMC cultures from ten chimpanzees were infected in parallel with amounts of HIV-1 virus stock equivalent to 10 ng p24 gag antigen. Supernatant was collected at days 4, 7, 11 and 14 and analyzed for levels of p24 by antigen capture analysis.

Figure 15:
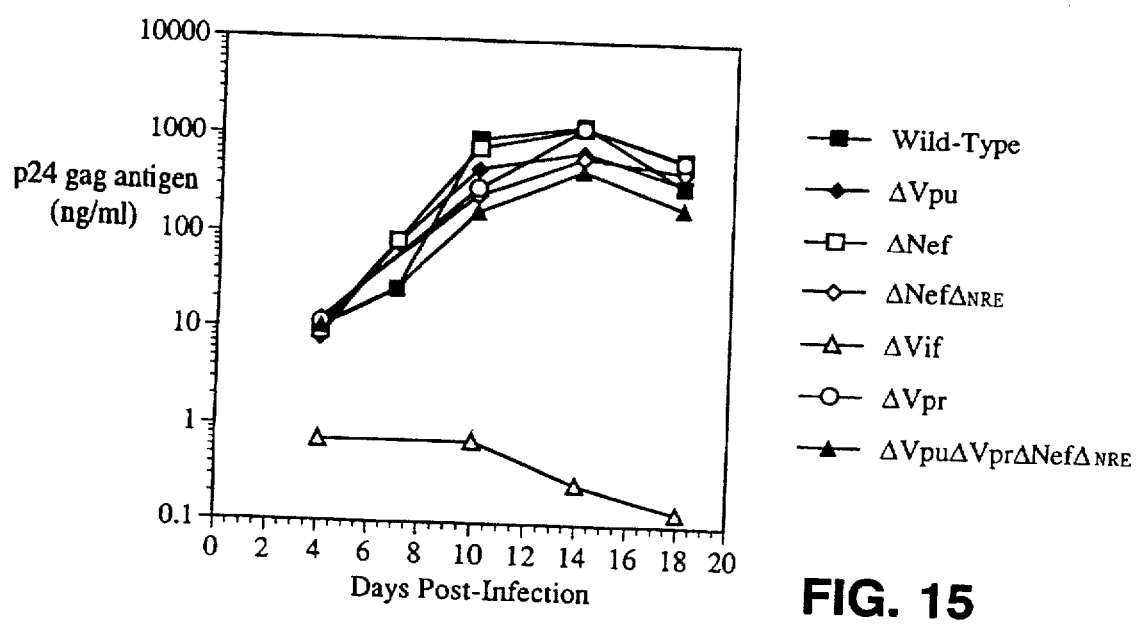

FIG. 15 is a line graph showing the replication of deletion mutant and wild-type HIV in human PBMC. PBMC previously activated with phytohemagglutinin (PHA) and growing in interleukin-2 (IL-2) were infected with an amount of virus stock equivalent to 40 ng p24 gag antigen. Virus production was measured on days 4, 7, 10, 14, and 18 by antigen capture analysis. Results are the average of duplicates.

Figure 16:
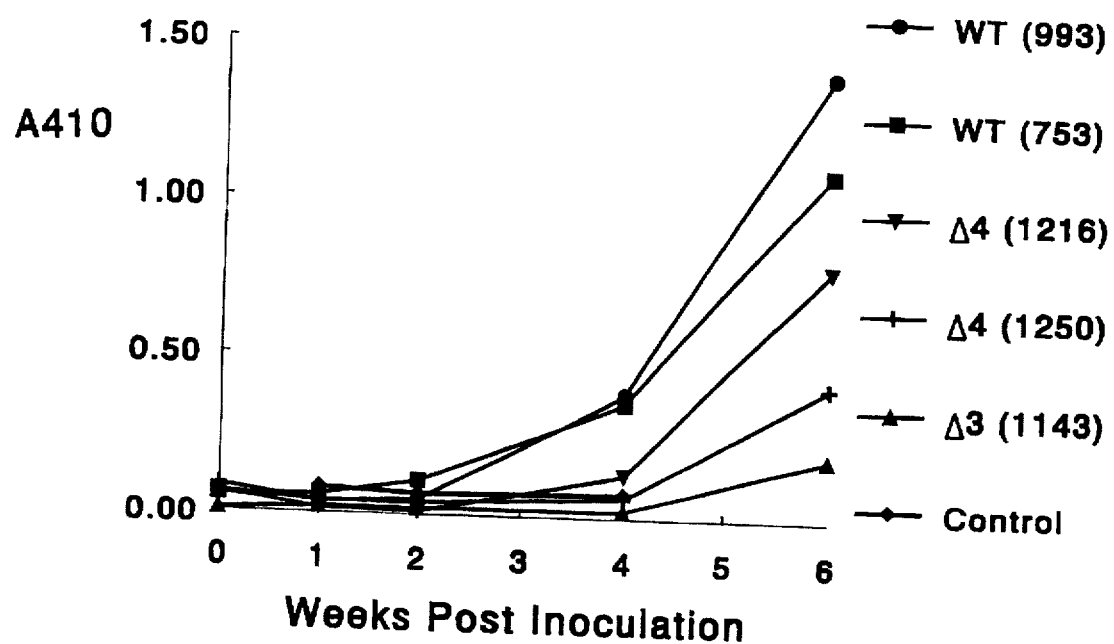

FIG. 16 is a line graph showing the development antibody responses in immunized chimpanzees to wild type and deletion mutant strains of HIV virus.

Primate Lentivirus Clones

There now follow examples of DNA clones according to the invention which include a deletion in the nef gene of SIVmac239 or HIV-1. All nef gene sequences isolated to date exhibit homology at the nucleotide and amino acid levels (*Human Retroviruses and AIDS* 1990. *A Compilation and Analysis of Nucleic Acid and Amino Acid Sequences*, ed. G. Myers et al., Los Alamos National Laboratory, Los Alamos, N.Mex.). In addition, the position of the nef gene in the lentiviral genome (i.e., between the env gene and the 3' LTR) is conserved (*Human Retroviruses and AIDS* 1990. *A Compilation and Analysis of Nucleic Acid and Amino Acid Sequences*, ed. G. Myers et al., Los Alamos National Laboratory, Los Alamos, N.Mex.). It is therefore a matter within the skill in the art to identify the nef gene sequence in any known or newly isolated primate lentivirus. Using standard techniques, such as those described below, said nef gene can be appropriately mutated, tested for pathogenicity, and compounded into a suitable vaccine that evokes protection against the AIDS virus.

The following clones are described to illustrate, not to limit, the invention. As described below, those of ordinary skill in the art can readily produce DNA clones from other SIV or HIV isolates having similar utility in the production of a nonpathogenic viral vaccine against AIDS.

SIVmac239 nef-deletion

Parental virus SIVmac239 was isolated from a macaque monkey (New England Regional Primate Research Center) that exhibited impaired T-cell function, lymphoproliferative disorders, and opportunistic infections, symptoms characteristic of SIV infection. Cell free serum samples from this animal were cocultivated with HuT-78 cells (a human tumor T-cell line available from American Type Culture Collection, 12301 Parklawn Drive, Rockville, Md. 20852 under accession No. TIB 161) and infectious SIVmac239 virus isolated from the HuT-78 cell supernatant as described in M. D. Daniel et al. (*Science* 228:1201, 1985). The cell supernatant was shown to possess detectable reverse transcriptase activity (by the method of M. D. Daniel et al., *Science* 228:1201, 1985) beginning 12 to 18 days after initiation of cocultivation. The presence of viral particles in this cell line was confirmed by electron microscopy; SIVmac239 infected cells displayed budding viral particles with a morphology characteristic of primate lentiviruses.

To facilitate cloning of the full length viral genome, endonuclease EcoRI was identified as a noncutter of SIVmac239 DNA. Total cell DNA was prepared from SIVmac239-infected HuT-78 cells and digested with EcoRI. Sucrose density gradient size-fractionated 10- to 20-kilobase pair EcoRI fragments were inserted into the EcoRI site of lambda cloning vector, EMBL4. This library was screened using pK2 BamA (described in V. Hirsch et al., *Cell* 49:307, 1987) as a probe, and full length molecular clone, SIVmac239, was isolated. The nucleotide sequence of both strands was determined by the primer-directed dideoxy-chain termination method of Sanger et al. (*Proc. Natl. Acad. Sci. USA* 74:5463, 1977) using Sequenase (i.e., T7 DNA polymerase) versions 1.0 or 2.0 (United States Biochemical, Cleveland, Ohio). $^{35}$S-labelled sequencing reactions were electrophoresed on a buffer gradient (0.75 to 2.5% Tris-borate buffer) 6% polyacrylamide/8M urea gel. Sequences were entered into an IBM-PC computer with an IBI gel reader and digitizer and were analyzed with IBI-Pustell DNA analysis software (International Biotechnologies, Inc., New Haven, Conn.).

The SIVmac239 clone in EMBL4 was then used to generate two plasmid subclones as follows. EMBL-SIVmac239 was digested with SphI, and a 6706 base pair fragment, containing the sequence from the SphI site in the left flanking cellular DNA sequence to the SphI site at viral nucleotide number 6451, was inserted into the SphI site of vector pBS(+) (Stratagene, La Jolla, Calif.) to produce subclone, p239SpSp5'. In a separate reaction, EMBL-SIVmac239 was digested with SphI and EcoRI, and a 6361 base pair fragment, containing the sequence from the SphI site at viral nucleotide 6452 to the EcoRI site in the right flanking cellular sequence, was inserted into SphI/EcoRI cleaved vector pBS(−) (Stratagene, La Jolla, Calif.) to produce subclone, p239SpE3'. These subclones were used to generate a full length genomic sequence as follows. Both p239SpSp5' and p239SpE3' were digested with SphI, ligated together, and used to directly transfect cultured cells (e.g., macaque peripheral blood lymphocytes).

A non-revertible null mutation (a deletion) was engineered into the nef gene of the SIVmac239 clone as follows. The C-terminus of the nef gene, contained within an SstI fragment of p239SpE3' and encompassing nucleotides 9230 to 11,436, was cloned into M13 to produce M13-SSTB. This M13 clone was subjected to oligonucleotide site specific deletion mutagenesis using procedures described in M. J. Zoller and M. Smith (*DNA* 3:479, 1984) or M. Strauss et al. (*Gene* 49:331, 1986). A 73 base pair oligonucleotide complementary to bases (9215 through 9250) and (9433 through 9469) was synthesized. The two segments were contiguous, i.e., bases 9251 through 9432 were not present on the 73-mer. This oligonucleotide was annealed to single stranded M13-SSTB in the presence of Klenow polymerase and the four deoxyribonucleotides to promote synthesis of the complementary strand. Since bases 9251 through 9432 were not included in the oligonucleotide primer, their complement was similarly not included in the newly synthesized negative strand. Double stranded replicative form (RF) phage DNA was transformed into *E. coli* host, JM109. DNA from the resulting M13 plaques was immobilized on nitrocellulose filters by standard techniques (W. D. Benton and R. W. Davis, *Science* 196:180, 1977) and screened for the sequence in the deleted region, using an oligonucleotide probe complementary to the deleted sequence. A negative signal was taken as an indication that a clone contained a nef deletion. One M13 clone, confirmed to have the expected deletion by DNA sequencing, was subsequently used for reconstruction of the full length viral sequence as follows. The fragment, containing the deletion, was liberated by digestion of deleted M13-SSTB, with SstI. Said fragment was then cloned into p239SpE3' to yield p239SpE3' (nef-deletion). Plasmid subclones, p239SpSp5' and p239SpE3' (nef-deletion), were digested with SphI, ligated together, and used to directly transfect cultured cells (e.g., macaque peripheral blood lymphocytes).

As shown in FIG. 1, the SIVmac239 nef gene overlaps the env gene sequence. Disruption of the env gene sequence of the SIVmac239 genome, or, generally, any PLV genome, can render the lentivirus non-infectious and, hence, not useful for the production of an effective live vaccine. For this reason, the nef deletion, contained in p239SpE3' (nef-deletion), leaves the env gene intact.

Plasmid clones p239SpSp5' and p239SpE3' (nef-deletion) have been deposited with the American Type Culture Collection and they, respectively, bear the accession numbers: ATCC No. 68365 and No. 68364. Applicant's assignee, the President and Fellows of Harvard University, acknowledge their responsibility to replace these cultures should they die before the end of the term of a patent issued hereon, and their responsibility to notify the ATCC of the issuance of such a patent, at which time the deposits will be made available to the public. Until that time the deposits will be made available to the Commissioner of Patents under the terms of 37 CFR §1.14 and 35 USC §112.

Using the SIVmac239 sequence provided in FIG. 1, one skilled in the art can engineer other non-revertible null mutations in the nef gene sequence. Deletions that remove a portion (≧10%) of the SIV nef open reading frame can be easily verified by restriction mapping. Such deletions of the Nef encoding nucleic acid, or deletions that disrupt Nef control or response sequences, in most cases, render the gene incapable of producing a Nef gene product. The absence of Nef gene product can be verified by immunoassay (e.g., Western blot analysis), using purified antibodies directed to the Nef protein or serum from primates infected with a primate lentivirus. When other types of null mutations are accomplished (e.g., smaller deletions), their efficacy can be tested using an in vivo assay. Briefly, for a simian immunodeficiency virus, an aliquot of purified virus derived from a mutant nef clone can be injected intravenously into a live, permissive host, preferably a rhesus monkey, and tested for pathogenicity (i.e., ability to induce AIDS-like disease symptoms). Virus harboring a genome with a null mutation in the nef gene (e.g., SIVmac239 nef-deletion) are nonpathogenic.

SIVmac239ΔnefΔNRE

Another example of an SIV DNA clone according to the invention, i.e., one which includes a deletion in the nef gene and a deletion in the NRE sequence of the long terminal repeat (LTR), was constructed as follows.

Plasmid p239SpE3' (nef-deletion) was digested with NsiI and StuI, enzymes which cut at unique sites within the NRE region of the SIVmac LTR. The DNA fragment comprising most of the plasmid sequence (but lacking the internal NRE fragment) was isolated, the protruding ends blunt-ended using T4 DNA polymerase, and the blunt ends ligated together to recreate a circular plasmid. The plasmid was reisolated, and was confirmed, by nucleotide sequence analysis, to be lacking nucleotides 9660 to 9831 (in the NRE region); this plasmid was termed p239SpE3'ΔnefΔNRE.

Plasmids p239SpSp5' and p239SpE3'ΔnefΔNRE were each digested with SphI, ligated together, and used to directly transfect permissive cultured cells (e.g., macaque peripheral blood lymphocytes) as described above. Such cells produced an SIVmac239 virus whose genome included a deletion in the nef gene and a deletion in the NRE sequence (i.e., SIV mac239ΔnefΔNRE).

SIVmac239Δ3

Another example of an SIV DNA clone according to the invention, i.e., one which includes deletions in the nef and vpr genes and in the NRE sequence was constructed as follows.

Plasmid p239SpSp5' was subjected to polymerase chain reaction (PCR) site specific mutagenesis by the method of Ho et al. (Gene 77:51, 1989). 35 bp oligonucleotides, complementary to bases (6135 through 6152) and (6254 through 6270) of SIVmac239, respectively, were synthesized and used as the PCR primers. Specifically such oligonucleotides were of sequence:

5' TCCAGGACTAGCATAAATTTGATC-CTCGCTTGCTA 3' (SEQ ID NO:1) and

5' TAGCAAGCGAGGATCAAATTTAT-GCTAGTCCTGGA 3' (SEQ ID NO:2).

The resultant plasmid, termed p239SpSp5'Δvpr, included a deletion of nucleotides 6153 through 6253 of the vpr gene.

Plasmids p239SpSp5'Δvpr and p239SpE3'ΔnefΔNRE were each digested with SphI, ligated together, and used to directly transfect permissive cultured cells (e.g., macaque peripheral blood lymphocytes) as described above. Such cells produced an SIVmac239 virus whose genome included deletions in the nef and vpr genes and in the NRE sequence (i.e., SIVmac239Δ3).

SIVmac239Δ4

Another example of an SIV DNA clone according to the invention, i.e., one which includes a deletion in the nef, vpr, and vpx genes and in the NRE sequence was constructed as follows.

Plasmid p239SpSp5' was subjected to PCR-site specific mutagenesis as described above. 30 bp oligonucleotides, complementary to bases (5973 through 5987) and (6254 through 6268) of SIVmac239, respectively, were synthesized and used as PCR primers. Specifically, such oligonucleotides were of sequence:

5' ATACTGGCATGATGATTGATCCTCGCTTGC 3'(SEQ ID NO:3) and

5' GCAAGCGAGGATCAATCATCATGCCAGTAT 3' (SEQ ID NO: 4).

The resultant plasmid, termed p239SpSp5'ΔvpxΔvpr, included a deletion of nucleotides 5988 through 6253 of the vpx and vpr genes.

Plasmids p239SpSp5'ΔvpxΔvpr and p239SpE3'ΔnefΔNRE were each digested with SphI, ligated together, and used to directly transfect permissive cultured cells (e.g., macaque peripheral blood lymphocytes) as described above. Such cells produced an SIVmac239 virus whose genome included deletions in the nef, vpr, and vpx genes and in the NRE sequence (i.e., SIVmac239Δ4).

Non-revertible null mutations can also be engineered into the genomic nef sequence of other primate lentivirus genomes, for example, HIV-1. FIG. 2 shows the complete nucleotide and amino acid sequence of an isolate of HIV-1; as indicated in this figure, the nef gene (referred to as E') includes the sequence between nucleotides 8,347 and 8,992. Said sequence is located between the env gene and the 3' LTR and exhibits nucleotide and amino acid sequence homology to the nef gene of the simian lentivirus isolate, SIVmac239. Non-revertible null mutations can be introduced into the HIV-1 nef sequence by standard recombinant DNA techniques, for example, site directed in vitro mutagenesis or deletion of sequence between restriction sites. Again, deletions that remove all or most of the HIV-1 nef open reading frame can be verified by restriction mapping or by immunoassay. Deletions which disrupt Nef control or response elements, in most cases, also render the gene incapable of producing a Nef gene product, and this event also could be tested by immunoassay as described above for SIV Nef. When other types of null mutations (e.g., smaller deletions) are accomplished, their efficacy should be tested using an in vivo assay. No permissive host (except humans) exists for directly testing the pathogenicity of a mutant HIV clone in vivo. However, as described below, due to the similarity in the human and simian nef sequences, an equivalent SIV nef-mutant clone (i.e., with a deletion in the corresponding SIV Nef domain) can be engineered and can be tested for pathogenicity in rhesus monkeys as described above.

There now follow specific examples of HIV-1 clones according to the invention. These examples are for the purpose of illustrating, not limiting, the invention.

HIV-1ΔnefΔNRE

An example of an HIV DNA clone according to the invention, i.e., one which includes a deletion in the nef gene and in the NRE sequence is constructed as follows.

Beginning with the proviral clone, termed pNL4-3 (Adachi et al., J. Virol. 59:284, 1986; available from the AIDS Research and Reference Reagent Program, NIAID, National Institute of Health, Bethesda, Md.), the HIV-1 sequence is sub-cloned into two separate vectors. Specifically, pNL4-3 is digested with ApaLI and EcoRI and a 5897 bp fragment including bp-154 (within the flanking cellular sequence) to bp 5743 (within the flanking cellular sequence) (i.e., the viral genes, gag, pol, vif, and vpr) is inserted into a plasmid vector, termed pDR8, to produce pLEFT.

Plasmid pDR8 was constructed by digesting pUC19 with NdeI and EarI (i.e., deleting the lacZ and lacI genes and the polylinker) and rendering the protruding ends blunt with T4 DNA polymerase. Into this backbone was inserted, by blunt-end ligation, an oligonucleotide of sequence:

5' TGGTGACCTTCGAAGGATCCCATAT-GTCTAGAGAATTCGGTCACCA 3'

3' ACCACTGGAAGCTTCCTAGGGTATACA-GATCTCTTAAGCCAGTGGT 5' (SEQ ID NO:14), to produce pDR8.

In a separate reaction pNL4-3 is digested with EcoRI and ThaI and a 4002 bp fragment including bp 5743 of FIG. 3 (SEQ ID NO:5) to bp 9745 (in the flanking cellular sequence) (i.e., the viral genes, tat, rev, vpu, env, nef, and LTR) is inserted into plasmid vector, pDR8, to produce pRIGHT.

To mutate the nef and NRE genes, pRIGHT is digested with NdeI or ApaLI and ThaI and at 3247 bp or 3136 bp viral fragment, respectively, is isolated and inserted into plasmid vector pDR8, to create pRIGHT-SUB1. The nef gene and NRE sequence are mutated by PCR-site specific mutagenesis by the method of Ho et al. (supra). PCR primers are chosen such that most or all of the nef and NRE sequences are deleted. For example, deletion of the nef gene may be accomplished using PCR primers of sequence:

5' AAGGATTTTGCTATAATAGCCACTTTTTTAAAA 3' (SEQ ID NO:6) and

5' TTTTAAAAAAGTGGCTTATTATAG-CAAAATCCTT 3' (SEQ ID NO: 7), complementary to bases (8770 through 8785) and (9047 through 9062) of the HIV-1 sequence of FIG. 3 (SEQ ID NO:5).

Deletion of the NRE sequence may be accomplished using PCR primers of sequence:

5' ACTGACCTTTGGATGGCATCCGGAGTACTTCA (SEQ ID NO:8) and

5' TGAAGTACTCCGGATGCCATCCAAAGGTCAGT 3' (SEQ ID NO:9), complementary to bases (9194 through 9209) and (9381 through 9396) of the HIV-1 sequence of FIG. 3 (SEQ ID NO:5). The mutated version of pRIGHT-SUB1 is digested with NdeI or ApaLI (corresponding to the enzyme chosen above) and ThaI and the 3075 bp or 2964 bp fragment, respectively isolated and re-inserted into NdeI- or ApaLI- and ThaI-digested pRIGHT to create pRIGHT-MUT1. pRIGHT-MUT1 and pLEFT are digested with EcoRI, ligated together, and used to directly transfect permissive cultured cells (e.g., human peripheral blood lymphocytes) as described in Sompayrac and Danna (*Proc. Natl. Acad. Sci. USA* 78:7575, 1981) or Milman and Herzberg (*Somat. Cell Genet.* 7:161, 1981) or Naidu et al. (*J. Virol.* 62:4691, 1988). Such cells produce an HIV-1 virus whose genome includes a deletion in the nef gene and in the NRE sequence (i.e., HIV-1ΔnefΔNRE).

HIV-1Δ3

Another example of an HIV DNA clone according to the invention, i.e., one which includes deletions in the nef and vpr genes and in the NRE sequence is constructed as follows.

Plasmids pRIGHT-MUT1 and pLEFT are constructed as described above. A fragment containing the vpr gene is further subcloned. Specifically, PLEFT is digested with BspMI or NdeI and EcoRI and a 697 bp or 621 bp viral fragment, respectively, is isolated and inserted into plasmid vector, pDR8, to create pLEFT-SUB1. The vpr gene is mutated by PCR-site specific mutagenesis (by the method of Ho et al., supra). PCR primers are designed such that most or all of the vpr gene is deleted. For example, primers may be of sequence:

5' AATGAATGGACACTAGTAATAAGAATTC 3' (SEQ ID NO:10) and

5' GAATTCTTATTACTAGTGTCCATTCATT 3' (SEQ ID NO:11), complementary to bases (5604 through 5619) and (5737 through 5748) of the HIV-1 sequence of FIG. 3 (SEQ ID NO:5). The mutated version of pLEFT-SUB1 is digested with BspMI or NdeI (corresponding to the enzyme chosen above) and EcoRI, and the 579 bp or 503 bp viral fragment, respectively, isolated and re-inserted into BspMI- or NdeI- and EcoRI-digested pLEFT to create PLEFT-MUT. pLEFT-MUT and pRIGHT-MUT1 are digested with EcoRI, ligated together, and used to directly transfect permissive cultured cells (e.g., human peripheral blood lymphocytes) as described in Sompayrac and Danna (*Proc. Natl. Acad. Sci. USA* 78:7575, 1981) or Milman and Herzberg (*Somat. Cell Genet.* 7:161, 1981) or Naidu et al. (*J. Virol.* 62:4691, 1988). Such cells produce an HIV-1 virus whose genome includes deletions in the nef and vpr genes and in the NRE sequence (i.e., HIV-1Δ3).

HIV-1Δ4

Another example of an HIV DNA clone according to the invention, i.e., one which includes deletions in the nef, vpr, and vpu genes and in the NRE sequence is constructed as follows.

Plasmids pLEFT-MUT, pRIGHT, and pRIGHT-MUT1 are constructed as described above.

A fragment containing the vpu gene is subcloned. Specifically, pRIGHT is digested with EcoRI and NdeI or ApaLI and a 864 bp or 656 bp fragment, respectively, is isolated and inserted into plasmid vector, pDR8, to create pRIGHT-SUB2. The vpu gene is mutated by PCR-site specific mutagenesis by the method of Ho et al. (supra). PCR primers are chosen such that most or all of the vpu gene is deleted. For example, primers may be of sequence:

5' GTAAGTAGTACATGTAATGAGAGTGAAGGAGA 3' (SEQ ID NO:12) and

5' TCTCCTTCACTCTCATTACATGTACTACTTAC 3' (SEQ ID NO:13), complementary to bases (6045 through 6060) and (6221 through 6236) of the HIV-1 sequence of FIG. 3 (SEQ ID NO:5). The mutated version of pRIGHT-SUB2 is digested with EcoRI and NdeI or ApaLI (corresponding to the enzyme chosen above) and the 475 bp or 686 bp (respectively) viral fragment isolated and inserted into an EcoRI- and NdeI- or ApaLI-digested pRIGHT-MUT1 backbone, to create pRIGHT-MUT2. pRIGHT-MUT2 and pLEFT-MUT are digested with EcoRI, ligated together, and used to directly transfect permissive cultured cells (e.g., human peripheral blood lymphocytes) as described in Sompayrac and Danna (*Proc. Natl. Acad. Sci. USA* 78:7575, 1981) or Milman and Herzberg (*Somat. Cell Genet.* 7:161, 1981) or Naidu et al. (*J. Virol.* 62:4691, 1988). Such cells produce an HIV-1 virus whose genome includes deletions in the nef, vpr, and vpu genes and in the NRE sequence (i.e., HIV1Δ4).

Additional Deletions in Non-Essential Genetic Elements

Safety is an important consideration in the development of mutant virus strains for vaccine purposes. In addition to Δnef, Δvif, Δvpr, Δvpx or Δvpu and ΔNRE, additional deletions in non-essential genetic elements of SIV or HIV can be made, thus yielding a more attenuated (and therefore, safer) virus that is still capable of generating a protective immune response. Such deletions can be made using routine methodology and recombinant virus can be screened for replication competency as described below.

For example, the NFKB binding element in the HIV-1 LTR dramatically influences the level of HIV-1 expression but is not absolutely required for virus replication (Leonard et al., J. Virol. 63:4919, 1989). HIV-1 contains two NFκB binding sequences in each LTR and SIVmac, SIVsm and HIV-2 contain only a single such element. Mutations in the SIVmac239 NFκB binding elements were constructed and engineered into both LTRs of SIVmac239 and into both LTRs of SIVmac239/316. Deletions in the NFKB binding sites, preferably in combination with Δnef, Δ3, Δ4 and other combinations of mutants described herein may further attenuate these deletion mutants, thus contributing to the safety of a mutant vaccine strain.

The cellular factor, Sp1, is constitutively expressed in most eucaryotic cells. Binding sites for Sp1 are present in the LTRs of HIV and SIV and these influence basal levels of HIV expression. Deletion of Sp1 binding elements from the HIV-1 LTR can reduce the level of HIV expression but is also not essential for replication (Ross et al., J. Virol. 65:4350, 1991). In accordance with the invention, deletions of the Sp1 binding sites can be combined with Δnef deletions.

Similarly, short deletions in non-essential essential genes such as gp41, gag and pol, may also be useful to further attenuate the virus. Such mutations can be generated using, e.g., oligonucleotide-directed site specific mutagenesis procedures, and screened for the ability to preserve replication competency using methods known in the art. For example, recent results indicate that sequences at the carboxy terminus of the transmembrane protein (TMP) of HIV-1 may also be dispensable for replication (Gabuzda et al., J. Virol. 66:3306, 1992; Dubay et al., J. Virol. 66:6616, 1992; Wilk et al. Virol. 189:167, 1992)

Isolation of Primate Lentivirus

Having produced an infectious DNA clone containing a nef mutation according to the invention, that clone is used to transfect appropriate cells, for example, immortalized lymphocytes, such as H9 cells or HuT-78 cells, or peripheral blood lymphocytes from donor mammals. After culturing the infected cells, primate lentiviruses, suitable for making a vaccine, can be isolated from the cell supernatant following centrifugation and filtration, using procedures identical to those utilized to isolate wild-type virus.

In order to more fully illustrate the manner of isolating primate lentivirus, the following example is presented.

Isolation of SIVmac239 nef-deletion Virus

SIVmac239 nef-deletion virus can be isolated by digesting p239SpSp5' and p239SpE3' (nef-deletion) DNA with SphI, ligating together, and transfecting into HuT-78 cells by the DEAE-dextran technique of Sompayrac and Danna (*Proc. Natl. Acad. Sci. USA* 78:7575, 1981) and Milman and Herzberg (*Somatic Cell Genet.* 7:161, 1981) followed by isolation of progeny virus as follows.

Five aliquots of viral DNA (3 μg of ligated DNA/aliquot) are sequentially added, with intermittent mixing, to 1.4 ml of serum-free Dulbecco's modified Eagle medium (GIBCO, Grand Island, N.Y.) containing 125 μg/ml DEAE-dextran and 50 mM Tris (pH 7.3). HuT-78 cells are split 1:2 or 1:3, grown to $3\times10^6$ cells/plate (i.e., 24 hours or less), washed twice with Dulbecco's modified Eagle medium, mixed with the 1.4 ml DNA solution, and incubated at 37° C. for 1 hr. The cells are then washed with serum-free Dulbecco modified Eagle medium, washed with serum-free RPMI 1640 medium (GIBCO, Grand Island, N.Y.), and incubated at 37° C. in RPMI 1640 medium containing 10% fetal calf serum. Transfected cells are split 1:2 or 1:3, twice per week.

Alternatively, SIVmac239 nef-deletion may be propagated by transfecting H9 cells by the above procedure or by transfecting macaque peripheral blood lymphocytes essentially by the above procedure, except that the cells are stimulated with 1 μg/ml phytohemagglutinin (GIBCO, Grand Island, N.Y.) for 48 hrs prior to transfection and grown in RPMI 1640 medium containing 10% interleukin-2 (lectin-free, T-cell growth factor; Electro-Nucleonics, Inc., Fairfield, N.J.) following transfection.

Generally, seven to fourteen days after transfection, cells are removed by centrifugation (1500 g, 10 minutes, 4° C.), and the supernatant is filtered through a disposable 0.45 micron filter (Corning, Corning, N.Y.). Cell-free supernatant is monitored for reverse transcriptase activity, using the methods of M. D. Daniel et al. (*Science* 228:1201, 1985), or for the amount of Gag antigen, by antigen capture (Coulter Immunology, Hialeah, Fla.). Cell free supernatant, possessing detectable reverse transcriptase activity and viral antigen, is saved as virus stock. Stocks may be stored in liquid nitrogen for long periods of time, e.g., one to two years, without significant loss of virus viability. A cycle of freezing and thawing, however, may reduce viral infectivity approximately tenfold.

Vaccine Production

A PLV molecular clone containing a non-revertible null mutation in the nef gene or a virus which harbors such a mutant genome is used to transfect or infect appropriate primate cells, e.g., immortalized HuT-78 or H9 cells, or peripheral blood lymphocytes, using procedures described above. After a standard incubation time, for example, seven to fourteen days, the culture medium is removed by aspiration, the cells are washed twice with phosphate-buffered saline (137 mM NaCl, 2.7 mM KCl, 4.3 mM $Na_2HPO_4.7H_2O$, 1.4 mM $KH_2PO_4$, pH 7.3) and the medium is replaced with serumfree RPMI 1640. Following an appropriate incubation time in serum-free medium (approximately 12 to 24 hours), virus is harvested by centrifugation and further purified by passage of the cell free supernatant through a 0.45 micron filter as described above. Viral stock is titered by standard techniques (*Techniques in HIV Research*, ed. A. Aldovini and B. D. Walker, Stockton Press, New York, N.Y.), diluted, if necessary, in a pharmaceutically acceptable carrier, such as physiological saline, and stored frozen in aliquots appropriate for a single immunizing dose. Stabilizers (e.g., $MgCl_2$, hydrolyzed gelatin, or sorbitol), antibiotics (e.g., streptomycin or neomycin), and pH indicators (e.g., phenol red), may also be added to the vaccine just prior to storage.

Method of Vaccination

An immunizing amount (i.e., an infecting dose) of this vaccine is administered by any standard procedure, for example, by intramuscular injection. This dose is effective over the course of at least twelve months.

Other embodiments are within the following claims. For example, the genome may be substantially identical to a PLV genome, but for the nef mutation discussed above and a non-revertible null mutation in one or more of the other PLV genes that are not essential to infectivity, for example, v, vpu, or vif (e.g., as described above), or the deletion of LTR sequences that are not essential for virus replication.

EXAMPLE 1

Construction and in vitro Properties of SIVmac Mutants With Deletions In The "Nonessential" Genes A panel of forty single and combination deletion mutants derived from SIVmac239 have been constructed. Characterization of these mutants and their in vitro growth properties will now be described.

Plasmids p239SpSp5' and p239SpR3' encode the left and right halves of the SIVmac239 genome. p239SpR3'/nef-open is a derivative of p239SpR3', where the TAA stop signal at codon 93 of nef has been mutated to GAA (Glu). This codon has been shown to result in a functional nef gene product in vivo. p239SpR3'/Δnef lacks nucleotides 9251 to 9432, resulting in a deletion within the nef gene without compromising any other open reading frame. p239SpR3'BstE2BI, p239SpR3'BstE2BIΔnef and p239SpR3'BstE2BIΔnefΔNRE are subclones of p239SpR3', p239SpR3'/Δnef and p239SpR3'/ΔnefΔNRE lack a BstE2-BstBI fragment within The first round amplification products overlap at the mutation site and extend leftward or rightward to a convenient restriction enzyme site. A second round of amplification was performed using the outer primer pair and a mixture of the first two reaction products as template, generating a product containing the desired deletion and flanked by SalI and SphI containing the SalI site into the restriction sites. The incorporation of the SalI site into the leftward outer primers #75 and #89 (Table 1) facilitated cloning into pUC19. The PCR products were digested with SalI and SphI and cloned into similarly-cut pUC19. These intermediate plasmids obtained from PCR amplification were characterized by DNA sequence analysis across the entire segment from the BclI site to the SphI site.

TABLE 1

Mutagenesis Primers[a]

| Designation | Orientation[b] | 5' position | 3' position | Sequence[c] | SEQ ID NO: |
|---|---|---|---|---|---|
| 075 | + | poly-G | 5153 | GGGGGTCGACTGATCACTACAGAACAAG | SEQ ID NO: 15 |
| 076 | − | poly-G | 6435 | GGGGGGGCATGCTTCTAGAGGGC | SEQ ID NO: 16 |
| 077 | − | 6268 | 5404 | GCAAGCGAGGATCAAAATTTTATGAGGCTATGCC | SEQ ID NO: 17 |
| 078 | + | 5404 | 6268 | GGCATAGCCTCATAAAATTTTGATCCTCGCTTGC | SEQ ID NO: 18 |
| 079 | − | 6270 | 6135 | TAGCAAGCGAGGATCAAATTTATGCTAGTCCTGGA | SEQ ID NO: 19 |
| 080 | + | 6135 | 6270 | TCCAGGACTAGCATAAATTTGATCCTCGCTTGCTA | SEQ ID NO: 20 |
| 089 | + | poly-G | 5895 | GGGGGTCGACTTCGAATGGCTAAACAGAACA | SEQ ID NO: 21 |
| 094 | + | 5406 | 5671 | CATAGCCTCATAAAATGACATTTTACTGCATAG | SEQ ID NO: 22 |
| 095 | − | 5671 | 5406 | CTATGCAGTAAAATGTCATTTTATGAGGCTATG | SEQ ID NO: 23 |
| 097 | + | 5973 | 6101 | ATACTGGCATGATGAATAGTAACATGGGCAGG | SEQ ID NO: 24 |
| 098 | − | 6101 | 5973 | CCTGCCCCATGTTACTATTCATCATGCCAGTAT | SEQ ID NO: 25 |
| 101 | + | 5973 | 6268 | ATACTGGCATGATGATTGATCCTCGCTTGC | SEQ ID NO: 26 |
| 102 | − | 6268 | 5973 | GCAAGCGAGGATCAATCATCATGCCAGTAT | SEQ ID NO: 27 |

[a]primers shown here were used in splice overlap extension (SOE) PCR to create the amplified fragments containing the deletions and cloned intermediates shown in FIG. 1. All oligonucleotide primers were synthesized on a Model 8400 DNA Synthesizer (Milligen/Biosearch Inc., Burlington, MA) and purified on oligonucleotide purification cartridges (OPC) (Applied Biosystems Inc., Foster City, CA).
[b]Orientation and numbering system is that of Regier and Desrosiers[9].
[c]All sequences are written in the 5'→3' orientation. Underlined restriction enzyme recognition sites used in cloning are as follows: GTCGAC SalI, TGATCA BclI, GCATGC SphI, TTCGAA BstBI. Primers tailed with non-hybridizing poly-G at the 5'-end are external. All others are internal mutagenic primers containing deletions.

the 3' flanking cellular DNA. p3'239/316Em*/nef-open and p3'239/316Em*/Δnef were created by substitution of the SphI to SstI fragment of SIVmac316 into the p239SpR3'/nef-open or p239SpR3'/Δnef plasmid respectively. The Em* plasmids contain eight point mutations encoding amino acid changes in the env gene relative to the SIVmac239 parent plasmid which result in a virus capable of replicating to much higher levels in rhesus alveolar macrophages than SIVmac239. These mutations are 67V→M, 165M→I, 176K→E, 199N→D, 382G→R, 442H→Y, 573K→T, 751R→G. Three additional changes, at 7890, 8268, and 8547, are silent and one at 9210 changes a Gly codon in the overlapping nef reading frame to Glu. The gp41 open reading frame is intact in the Em* constructs. p3'239/316Em*ΔnefΔNRE was constructed by substituting the SstI to EcoRI fragment of p239SpR3'BstE2BIΔnefΔNRE containing the nef and U3 deletions into p3'239/316Em*/nef-open.

Mutagenesis and Construction of Left Half Deletion Mutants

Figure 4:
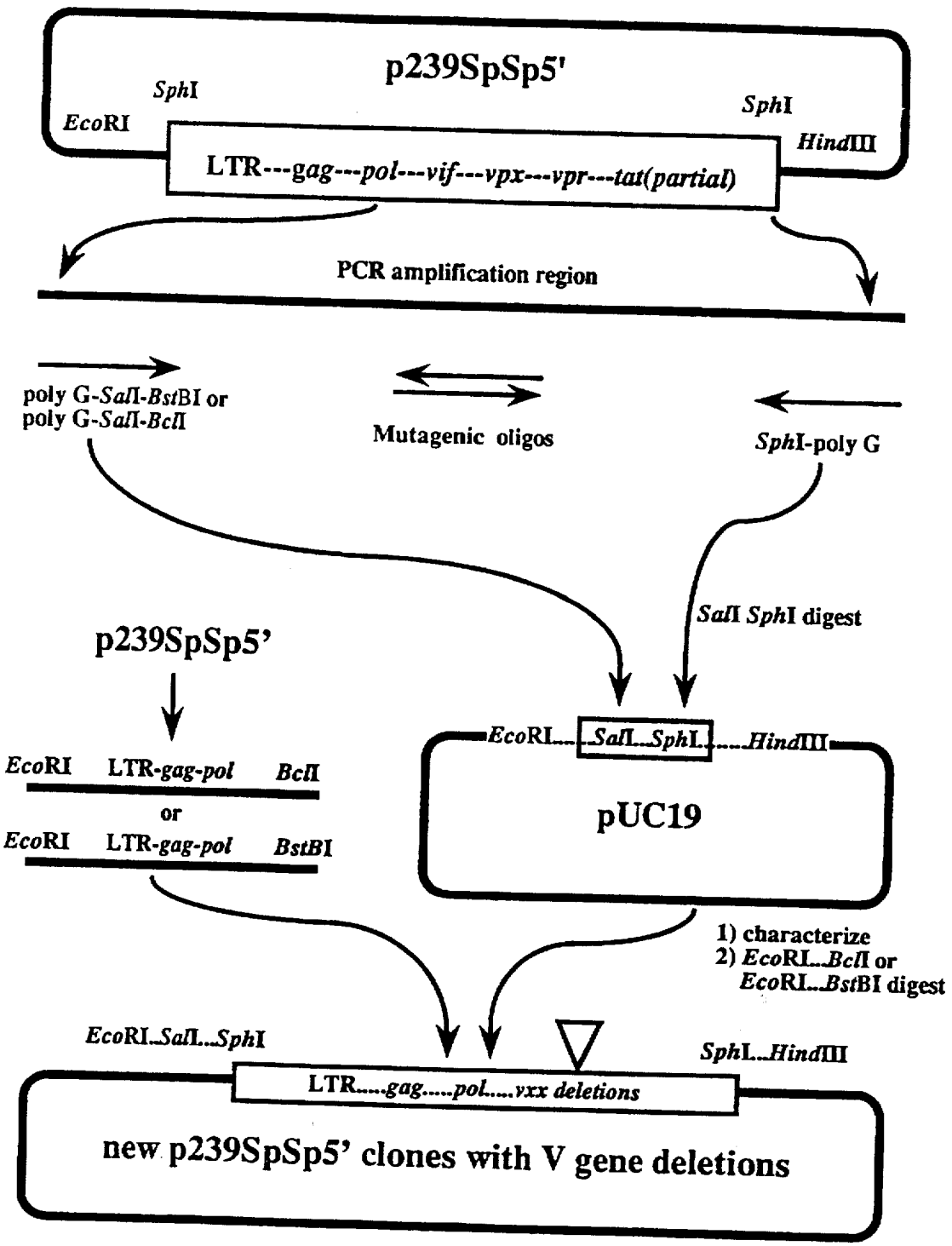
FIG. 4 is a diagram showing the strategy for construction of plasmids containing deletion mutations in the left half of SIVmac239.

SOE PCR was used to create deletions in the vif, vpx and vpr genes of SIVmac239 (see FIG. 4). Briefly, two PCR reactions were performed using p239SpSp5' as template.

To reconstitute a full-length left-half clone, a restriction fragment from p239SpSp5' containing the viral LTR-gag-pol sequence was inserted into the PCR-derived intermediate plasmids. Δvpx, Δvpr and ΔvpxΔvpr mutants were grown in the damstrain of E. coli, GM2163 (New England Biolabs, Beverly, Mass.), digested with EcoRI and BclI and ligated to the EcoRI to BclI fragment of p239SpSp5'.

Δvif and ΔvifΔvpxΔvpr mutants were digested with EcoRI and BstBI and ligated to the EcoRI to BstBI fragment of p239SpSp5'.

The ΔvifΔvpr mutant was obtained by digestion of the Δvpr intermediate plasmid with EcoRI and BstBI, followed by ligation to the EcoRI and BstBI fragment of the reconstructed Δvif clone. The integrity of the cloning junction was confirmed by DNA sequence analysis. Diagrams of these deletions are shown in FIGS. 5 and 6A–6C.

All final constructs were found to be free from additional mutations other than the deletions engineered into them with the exception of the single deletion mutant Δvpx which had a G→A point mutation at nucleotide 6102. This point mutation is twelve base pairs downstream of the deletion in vpx and is located in the unique vpx region that was the target of mutagenesis. The Δvpx construct used for replication analysis in CEMx174 cells had an additional point mutation at nucleotide 5892, which changed $Asn_{185}$ to Asp in the vif open reading frame. No phenotypic differences from wild-type were observed with this mutant in these cells, nor were there differences observed with any of the three multiply-deleted mutants with deletions in the vpx and vpr genes, which did have a fully wild-type vif reading frame (FIG. 7). An additional Δvpx construct that was completely wild-type for vif was selected from the same SOE PCR reactions and used for further analyses in primary cells (FIGS. 9 and 10).

Construction of Plasmids Containing Deletions in the "Nonessential" Genes

The general scheme for deletion mutant plasmid construction is shown in FIG. 4. Creation of deletions in left and right half plasmids facilitated the analysis of combinations of deletions since left and right half plasmids could be mixed and matched as desired. All deletion mutations were created being careful to avoid known splice acceptor and donor sites (FIGS. 5, 6A–6C). In all cases except the vif/vpx/vpr triple mutant, deletions were designed so that downstream sequences, when present, were out of frame for that gene. The following six mutant plasmids derived from the left half plasmid were created by splice overlap extension: p2395'Δvif, p2395'Δvpx, p2395'Δvpr, p2395'ΔvpxΔvpr, p2395'ΔvifΔvpr, and p2395'ΔvifΔvpxΔvpr. The mutant plasmids derived from p239SpR3' and p3'239/316Em* are: p3'239Δnef, p3'239ΔnefΔNRE, p3'239/316Em*Δnef and p3'239/316Em*ΔnefΔNRE. The plasmids encoding the right half of the SIV genome contain either the wild-type SIVmac239 env gene or the env gene from the macrophage-competent virus SIVmac316Em*. Nine point mutations exist in gp120 and gp41 of SIVmac316Em* which confer high replicative capacity for primary macrophages. The deletion mutants based on SIVmac316Em* were constructed so that the effects of the nonessential gene deletions on replication in macrophages could be determined.

Wild-type and mutant left and right half clones were combined in all forty-two permutations of left-right plasmid pairs, so that six mutant and one wild-type left half plasmids were combined with four mutant and two wild-type right half plasmids. Virus was reconstructed by digesting left and right plasmids with SphI and generating virus stocks via transfection and replication in CEMx174 cells or by transient expression in COS-1 fibroblasts.

Cells

The B/T hybrid cell line, CEMx174, was maintained in RPMI 1640 medium (Gibco Laboratories, Grand Island, N.Y.) supplemented with 10% heat-inactivated fetal bovine serum (Gibco). Rhesus monkey peripheral blood mononuclear cells (PBMC) were prepared by banding whole heparinized macaque blood on Lymphocyte Separation Media (Organon Teknika, Durham, N.C.) according to the manufacturer's recommendations. Rhesus monkey alveolar macrophages were obtained by pulmonary lavage from healthy animals shown to be seronegative for SIV, type D retroviruses and simian foamy virus and grown in Iscove's modified Dulbecco's medium supplemented with 20% heat-inactivated human type AB serum (Gibco), 20 units/ml GM-CSF (Genetics Institute, Cambridge, Mass.), 100 U penicillin per ml, 100 mg streptomycin per ml, 0.25 mg per ml amphotericin B and 10 mg/ml gentamicin (Gibco) before infection.

Preparation of Virus Stocks

Pelleted CEMx174 cells were transfected with three mg each of SphI-digested plasmids p239SpSp5' and p239SpR3' or mutant plasmids derived from them using DEAE dextran, a procedure well known in the art. COS-1 fibroblast cells were transfected with a slightly different DEAE dextran procedure, which included incubation for 2.5 hrs in 80 mM chloroquine (Sigma Chemical, St. Louis, Mo.) and shocking for 2.5 min with 10% dimethylsulfoxide (Fisher Scientific Co., Fair Lawn, N.J.). Virus supernatant was harvested at seven to nine days (CEMx174) or three to five days (COS-1) post-transfection and stored in 0.5 or 1 ml aliquots at −70° C. Virus was quantitated by determining the concentration of p27 gag antigen using a commercially available antigen capture kit, as recommended by the manufacturer (Coulter Corp., Hialeah, Fla.).

Replication of Deletion Mutants in CEMx174

CEMx174 cells split 1:3 the previous day were plated out at a concentration of $5 \times 10^5$ cells per ml in 48-well flat bottomed plates in a volume of one ml. Cells were infected with an amount of COS-1-derived virus equivalent to 0.2 ng p27 gag antigen. All infections were performed in duplicate. Supernatant was sampled and assayed for SIV p27 by antigen capture beginning on day five and thereafter at approximately four to five day intervals. Approximately twice weekly, the cells were split 1:3 if they had grown to a sufficient level, otherwise the supernatant was replaced with fresh medium.

In CEMx174 cells, all viruses except those deleted in vif replicated with kinetics similar or identical to that of the wild-type SIVmac239 parent virus (FIG. 7 and Table 2). In addition to those mutants shown in the figure, all other combination deletion mutants with the SIVmac239 env background were assayed and found to fit this pattern. Similarly, no differences from wild-type were observed in the rate of appearance or degree of syncytium formation with any of the replicating mutants in these cells. Although slight differences can be discerned with some of the mutants that retain vif in the data shown in FIG. 7, consistent differences were not observed in repeated experiments. Thus, vpr, vpx, nef and upstream U3 sequences are not rate-limiting for SIVmac239 replication in CEMx174 cells. Even a mutant virus missing all four of these genetic elements replicates indistinguishably from wild-type in these cells.

The deletion mutant Δ5, which lacks the vif, vpx, vpr and nef genes and the upstream region of U3, does replicate, but exceedingly slowly, in CEMx174 cells. The kinetics of viral replication in one transfection of SIV Δ5 DNA and in two sequential passes of viral stocks have been measured. Although the exact kinetics varied somewhat in the three experiments, virus replication was very slow on all three occasions. In the second serial passage, virus detected by antigen capture only began to appear at about day 50 and eventually rose to moderately high levels after more than 100 days (FIG. 8). Syncytia began to appear at the same time as supernatant antigen and persisted to a moderate degree throughout the infection. The slow but definite replication of SIVmac239 Δ5 upon serial passage suggests a consistent phenotype and the absence of contaminating wild-type virus. The presence of the original deletions in long-term Δ5-infected CEMx174 cells was confirmed by PCR analysis. The presence of non-deleted DNA forms was not observed. Similar replication for the single mutant Δvif have not been demonstrated.

TABLE 2

Summary of replication of SIVmac deletion mutants in three cell types[a]

| Virus | CEMx174 | PBMCs | Macrophages |
|---|---|---|---|
| Wild-Type | + | + | + |
| Δnef | + | + | + |

TABLE 2-continued

Summary of replication of SIVmac deletion mutants in three cell types[a]

| Virus | CEMx174 | PBMCs | Macrophages |
|---|---|---|---|
| ΔnefΔNRE | + | + | + |
| Δvpx | + | ↓ | ↓↓↓ |
| ΔvpxΔnef | + | ↓ | ↓↓↓ |
| ΔvpxΔnefΔNRE | + | ↓ | ↓↓↓ |
| Δvpr | + | + | + |
| ΔvprΔnef | + | + | + |
| ΔvprΔnefΔNRE | + | + | + |
| ΔvpxΔvpr | + | ↓↓ | ↓↓↓ |
| ΔvpxΔvprΔnef | + | ↓↓ | ↓↓↓ |
| ΔvpxΔvprΔnefNRE | + | ↓↓ | ↓↓↓ |
| Δvif | ↓↓↓ | ↓↓↓ | NT |
| ΔvifΔnef | ↓↓↓ | ↓↓↓ | NT |
| ΔvifΔnefΔNRE | ↓↓↓ | ↓↓↓ | NT |
| ΔvifΔvpr | ↓↓↓ | ↓↓↓ | NT |
| ΔvifΔvprΔnef | ↓↓↓ | ↓↓↓ | NT |
| ΔvifΔvprΔnefΔNRE | ↓↓↓ | ↓↓↓ | NT |
| ΔvifΔvpxΔvpr | ↓↓↓ | ↓↓↓ | NT |
| ΔvifΔvpxΔvprΔnef | ↓↓↓ | ↓↓↓ | NT |
| ΔvifΔvpxΔvprΔnefNRE | ↓↓↓ | ↓↓↓ | NT |

[a]All twenty one wild-type and mutant viruses constructed for this study are listed. Viruses tested in CEMx174 and PBMC cells contain the wild-type SIVmac239 envelope gene. Viruses tested in macrophages contain the SIVmac316 envelope gene.
+ — Replication indistinguishable from wild-type (see text).
↓ — Virus replication is diminished approximately one log from peak wild-type levels.
↓↓ — Virus replication is diminished approximately two logs from peak wild-type levels.
↓↓↓ — Virus replication is diminished three or more logs from peak wild-type levels and/or significant replication is not detected within thirty days of infection.
NT — not tested.

Virus Replication in Primary Rhesus Monkey PBMC

Lymphocytes in PBMC samples were activated for 72 hrs with 1 mg/ml phytohemagglutinin (Sigma), washed twice in serum-free RPMI 1640, and incubated with 10% interleukin-2 (Schiapparelli, Columbia, Md.), 20% fetal bovine serum, and 3.8 mg/ml β-mercaptoethanol (Sigma) overnight before infection. Rhesus PBMC were seeded at a concentration of $1 \times 10^6$ cells per ml in 48-well flat bottomed plates. Activated PBMC were infected with COS-1-derived SIV stocks containing 0.2 ng p27 on one occasion, or CEMx174-derived SIV stocks containing 4 ng p27 on another. On each occasion, the PBMC cultures were derived from a different animal. All infections were performed in duplicate. Supernatant was sampled and assayed for SIV p27 by antigen capture using the Coulter kit at approximately three to four day intervals. At the time of sampling, the cell supernatant was replaced with fresh medium.

Significant differences were observed in the replication of some of the SIV deletion mutants in rhesus monkey PBMC activated with PHA and grown in the presence of interleukin-2 (FIG. 9 and Table 2). The single deletion mutant Δvpr grew with kinetics similar or identical to that of the wild-type SIVmac239 parent virus, as did the Δnef and ΔnefΔNRE deletion mutants. Virus strains with combinations of deletions in these three genetic elements also replicated like wild-type in rhesus monkey PBMC cultures (Table 2). Very small differences, such as those evident with Δvpr and Δnef in FIG. 9, were not reproducibly observed and were not large enough to be judged as significantly different. Previous repeated testing also failed to reveal a significant effect of nef deletion on replication in PBMC. However, the vpx deletion mutants were reproducibly delayed in their replication properties and grew to only five or ten percent of the peak wild-type level. The double mutant deleted in both vpx and vpr was similarly diminished in its replication properties, growing less well than even the Δvpx single deletion mutant. Δ4 virus, missing nef, vpx, vpr and NRE, was similarly retarded in its replication potential in PBMC. Deletion of vif, alone or in combination with other genes, produced virus whose level of replication in PBMC was below the limits of detection (approximately 0.05 ng/ml p27).

Virus Replication in Rhesus Monkey Alveolar Macrophages

Alveolar macrophages were seeded at a concentration of $3 \times 10^5$ cells per ml in 48-well flat-bottom plates in a total volume of one ml per well. Twenty-four hours later, macrophages were infected with an amount of wild-type or mutant SIV equivalent to 4–15 ng p27 gag antigen prepared in CEMx174. On each of four occasions, macrophage cultures were prepared from a single animal, for a total of four animals being used in the different experiments. Infections for any given experiment were done in duplicate. All wild-type and mutant viruses analyzed for growth on macrophages had the env gene derived from SIVmac316. Supernatant was sampled and assayed for SIV p27 by antigen capture at approximately four to five day intervals using the Coulter kit. Approximately twice weekly, the cell supernatant was replaced with fresh medium.

The results of virus replication analysis in rhesus alveolar macrophages were found to be similar to the results observed in rhesus PBMC, but with somewhat larger differences observed in some cases (FIG. 10 and Table 2). Based on four different experiments with each infection done in duplicate, the Δnef and ΔnefΔNRE deletion mutations did not appreciably or consistently alter the replication ability of the virus in macrophages. Although a small delay or a slightly diminished peak replication rate was observed with the Δvpr virus and ΔvprΔnef virus in all four of the experiments, it was not a large effect and its significance cannot be stated with confidence. However, Δvpx and combinations that included Δvpx replicated very poorly if at all in these primary macrophage cultures. When these cultures were positive for vpx-deleted virus, particularly at early time points, it is possible that some or all of the detected antigen represented residual input virus. Replication of viruses with a deletion in the vif gene was below detectable levels.

Viral Replication of Deletion Mutants

In summary, results of the experiments described above show little or no contribution of the vpr gene to virus replication in cell culture, either in CEMx174 cells, rhesus monkey PBMC, or in rhesus alveolar macrophages. Deletion of the vpr gene caused little or no change in the growth properties of SIVmac239 in CEMx174 cells, in rhesus monkey, or in rhesus monkey alveolar macrophages. Deletion of the vpx gene resulted in a greatly reduced rate of replication of the virus in the primary PBMC and macrophage cultures, but no significant reduction in replication of the virus in CEMx174 cells. Deletion of the vpx gene appeared to have a greater effect on virus replication in macrophages than in PBMC. Deletion of the vif gene caused a dramatic reduction in replication in all cell types tested. However, even Δ5, which contains deletions in all five targeted regions (vif, vpx, vpr, nef and U3), can still replicate in CEMx174 cells albeit with greatly delayed kinetics. Deletion of nef, alone or in combination with deletions in U3 and vpr, had no observable effect on replication of the virus in any of the cells tested.

The disease induced by cloned SIVmac239 in rhesus monkeys has been well characterized and is very similar to HIV-1-induced disease in humans. As such, it is an important model for the study of AIDS pathogenesis. The collection of mutants described herein provides vital tools for analyzing gene function at a molecular level and for investigating the relative importance of these genetic elements for viral replication, persistence and disease progression in the animal model.

EXAMPLE 2

Protective Effects of a Live Attenuated SIV Vaccine With a Deletion in the nef Gene Live attenuated SIVΔnef was tested in monkeys as a vaccine. Six rhesus monkeys that were infected with cloned SIV mac239 that contained a constructed deletion in the auxiliary gene nef have maintained extremely low virus burdens and normal CD4+ lymphocyte concentrations and have remained healthy for more than 3 years after experimental inoculation with the mutated virus. Eleven of twelve rhesus monkeys infected with wild-type SIV in parallel have died over this same period. The rhesus monkeys infected with SIVmac239/nef-deletion have shown no clinical signs whatsoever over the entire period of observation.

Four of the rhesus monkeys infected with nef-deleted SIV were challenged with wild-type, pathogenic SIVmac 2.25 years after the initial inoculation with the mutated virus (Table 3). No booster immunizations of any type were used. Two of the vaccinated rhesus monkeys were challenged with cloned pathogenic SIVmac239/nef-open (intact nef), and two were challenged with uncloned pathogenic SIVmac251, a strain distinct from but closely related to SIVmac239. SIVmac239 shares approximately 93% amino acid identity in the gp120 Env protein with clones derived from SIVmac251-infected cells. In both cases, virus stocks were prepared in primary rhesus monkey peripheral blood mononuclear cell (PBMC) cultures, and aliquots of the frozen virus stocks were carefully titered in rhesus monkeys before the challenge experiment. In both cases, ten rhesus monkey infectious doses were used for the challenge. Neutralizing antibody titers on the day of challenge ranged from 1:320 to 1:2560 in the four rhesus monkeys previously vaccinated with live nef-deletion virus (Table 3). Virus loads, measured by limiting dilution co-culture and semiquantitative PCR, were extremely low before challenge. SIV was not recovered from $10^6$ PBMCs of the four rhesus monkeys on the day of challenge (Table 3). Two naive rhesus monkeys served as controls for each of the challenge viruses.

TABLE 3

| Rhesus monkey | SIV | Antibody | Challenge |
|---|---|---|---|
| 353-88 | — | 1:1280 | SIVmac230/nef-open |
| 397-88 | — | 1:1280 | SIVmac239/nef-open |
| 71-88 | — | 1:320 | SIVmac251 |
| 255-88 | — | 1:2560 | SIVmac251 |

Several parameters were monitored for evidence of protection against the challenge viruses. All four control monkeys showed a spike of plasma antigenemia 2 weeks after challenge (Table 4). In some cases, the plasma antigenemia persisted, and in others, it dipped below detectable levels only to reappear at a later time. No plasma antigenemia was detected at any time in any of the four previously vaccinated monkeys (Table 4).

Virus loads were also evaluated by measuring the numbers of PBMCs required to recover SIV by limiting dilution co-culture. All four unvaccinated control monkeys exhibited high virus burdens (Table 5). Generally, 1,000 to 20,000 PBMCs were needed for SIV recovery from the control animals. One test monkey, 397-88, showed a spike in virus recovery at 4 weeks after the challenge in that SIV was recovered with 74,000 or more PBMCs. SIV recovery in subsequent weeks from monkey 397-88, howver, was negative even with $10^6$ cells. Virus loads with this measurement were also stably low in the other three previously vaccinated animals because virus recovery required $\geq 10^6$ PBMCs (Table 5).

Rhesus monkeys vaccinated with SIV-mac239/nef-deletion appear by all criteria used to have resisted challenge by wild-type pathogenic SIV. Previously vaccinated animals showed no evidence of plasma antigenemia at any time after challenge and maintained extremely low virus burdens as was observed before the challenge. Furthermore, genetic analysis of recovered virus and viral DNA present in their PBMCs revealed no evidence of wild-type, nef-open challenge virus. All four unvaccinated controls died, whereas all four previously vaccinated animals are alive and healthy and show no signs of the presence of wild-type virus. These data indicate that the live attenuated SIVΔnef strain of the invention is safe and efficacious in an animal model and suggest that similarly deleted lentivirus strains hold promise as vaccine candidates.

TABLE 4

Protective effects of live attenuated nef-deletion vaccine on plasma antigenemia. The limit of detection of the assay used was approximately 0.05 ng/ml. W, weeks after challenge; D, dead.

| Rhesus monkey | Vaccine virus/challenge virus | Plasma antigenemia (nanograms of p27 per milliliter of plasma) | | | | | | | | | |
|---|---|---|---|---|---|---|---|---|---|---|---|
| | | W0 | W2 | W4 | W6 | W8 | W12 | W16 | W24 | W31 | W36 |
| 148-88 | None/251 | 0.0 | 8.8 | 0.0 | 0.0 | 0.0 | 0.0 | 0.0 | 0.2 | D | |
| 388-90 | None/251 | 0.0 | 2.7 | 0.2 | 0.1 | 0.2 | 2.0 | 2.3 | 3.5 | 1.8 | D |
| 71-88 | ΔNEF/251 | 0.0 | 0.0 | 0.0 | 0.0 | 0.0 | 0.0 | 0.0 | 0.0 | 0.0 | 0.0 |
| 255-88 | ΔNEF/251 | 0.0 | 0.0 | 0.0 | 0.0 | 0.0 | 0.0 | 0.0 | 0.0 | 0.0 | 0.0 |
| 246-90 | None/239 | 0.0 | 1.3 | 0.1 | 0.0 | 0.0 | 0.7 | 1.6 | 2.6 | 3.0 | D |
| 208-89 | None/239 | 0.0 | 0.1 | 0.0 | 0.0 | D | | | | | |
| 353-88 | ΔNEF/239 | 0.0 | 0.0 | 0.0 | 0.0 | 0.0 | 0.0 | 0.0 | 0.0 | 0.0 | 0.0 |
| 397-88 | ΔNEF/239 | 0.0 | 0.0 | 0.0 | 0.0 | 0.0 | 0.0 | 0.0 | 0.0 | 0.0 | 0.0 |

TABLE 5

Protective effects of live attenuated nef-deletion vaccine on virus load, which was measured by serial three-fold dilutions starting with $10^6$ PBMCs in duplicate by co-cultivation with CEM × 174. Virus load is expressed in terms of the number of PBMCs necessary to recover SIV. W, weeks after challenge. NS, no sample.

| Rhesus monkey | Vaccine virus/ challenge virus | Virus load (PBMCs) | | | | | |
|---|---|---|---|---|---|---|---|
| | | W4 | W8 | W12 | W24 | W31 | W36 |
| 148-88 | None/251 | 2,743 | 12,345 | 2,743 | 111,111 | Dead | |
| 388-90 | None/251 | 2,743 | 4,115 | 8,230 | 37,037 | 12,345 | Dead |
| 71-88 | ΔNEF/251 | >$10^6$ | >$10^6$ | >$10^6$ | >$10^6$ | >$10^6$ | >$10^6$ |
| 255-88 | ΔNEF/251 | >$10^6$ | >$10^6$ | $10^6$ | $10^6$ | $10^6$ | >$10^6$ |
| 246-90 | None/239 | 914 | 4,115 | 2,743 | 4,115 | 2,743 | Dead |
| 208-89 | None/239 | 1,371 | NS | Dead | | | |
| 353-88 | ΔNEF/239 | >$10^6$ | >$10^6$ | >$10^6$ | >$10^6$ | >$10^6$ | >$10^6$ |
| 397-88 | ΔNEF/239 | 74,074 | >$10^6$ | >$10^6$ | >$10^6$ | >$10^6$ | >$10^6$ |

EXAMPLE 3

Construction and in vitro Properties of HIV-1 Mutants With Deletions in the "Non-essential" Genes A panel of 23 mutants with single and combination deletions in non-essential genes of the wild-type HIV-1 infectious molecular clone, NL4-3, were constructed. These mutants are described below.

Plasmids

Plasmid pNL4-3 contains a chimeric HIV-1 provirus. The 14,877 bp plasmid contains the 5' half of proviral NY5 and the 3' half of proviral LAV sequences joined at a shared EcoRI site in the vpr gene. The proviral halves and flanking cellular DNA are carried in a derivative of pUC18. The numbering system used throughout this paper is that of Buckler, et al. (Buckler, C E, Buckler-White, A J, Willey, R, and McCoy, J: Genbank Accession Number: M19921, 1988). To facilitate mutagenesis, handling, and biosafety, fragments of pNL4-3 were subcloned into a pUC19 derivative, pDR8, in which the sequences between NdeI (bp 183) and EarI (bp 684) were replaced by a synthetic oligonucleotide, 5'-TGGTGACCTTCGAAGGATCCCATATGTCTAGAG-AATTCGGTCACCA-3'(SEQ ID NO: 14). This custom polylinker contains restriction enzyme recognition sites for BstEII, BstBI, BamHI, NdeI, XbaI, EcoRI and BstEII. A plasmid containing the 5' half of the NL4-3 genome was constructed by treatment of pNL4-3 with ApaLI, blunt end repair with E. coli DNA polymerase I Klenow fragment and subsequent treatment with EcoRI. The 5,747 bp fragment containing 155 bp of cellular DNA and 559 2 bp of NY5 LTR, gag, pol, vif and part of vpr was cloned into pDR8 between the BstBI site, blunt end repaired with E. coli DNA polymerase I Klenow fragment, and the EcoRI site. Similarly, a plasmid containing the 3' half of the NL4-3 genome was made by treatment with EcoRI and BstUI. The 4,002 bp fragment containing 3968 bp of LAV vpr, tat, rev, env and LTR and 34 bp of cellular DNA was cloned between the BstBI, blunt end repaired, and EcoRI sites of pDR8. Two subclones of each genomic half were tested for infectivity by treatment with EcoRI, mixing equimolar amounts of 5' and 3' halves, ligation and transfection into CEMx174 cells. All 4 combinations of subclones were infectious and produced CPE and p24 antigen with kinetics and yields similar to cells transfected with the full-length parent plasmid, pNL4-3. The 5' half subclone, p83-2, and 3' half subclone, p83-10, were used for the work below.

Subcloning Regions for Mutagenesis

The overall scheme of deletion mutant construction is shown in FIG. 11. The vif/vpr region was subcloned by treatment of p83-2 with BspMI which removed 5148 bp of cellular DNA, LTR, gag and most pol sequences. These sequences were replaced with an oligonucleotide linker, 5'-CAGAGTCCTTGGATCCTTATGGAAAACA-3' (SEQ ID NO:28), synthesized as two complementary oligonucleotides which annealed to produce sticky ends matching the two different BspMI sticky ends in the plasmid. The linker contained an additional unique BamHI site to aid in screening. The resulting plasmid, p102-7, was used for mutagenesis of vif and vpr.

The vpu region was subcloned by digestion of pNL4-3 with ApaLI, blunt end repair and digestion with EcoRI. The 767 bp fragment containing vpu was ligated to pDR8 prepared by digestion with BstBI (blunt end repaired) and EcoRI. The resulting plasmid, p83-16, was used for mutagenesis of vpu.

The nef/3'-LTR region was subcloned by digestion of pNL4-3 with BstUI and BamHI. The 1,293 bp fragment containing nef was ligated to pDR8 prepared by digestion with BstBI (blunt end repaired) and BamHI. The resulting plasmid, p83-11 was used for mutagenesis of nef and the upstream sequences in U3 of the 3'-LTR.

Oligonucleotides

All oligonucleotides used as sequencing or mutagenic PCR primers were synthesized on a Cyclone Model 8400 (Milligen, Burlington, Mass.) using cyanoethyl phosporamidite chemistry. Oligonucleotides were purified using Oligonucleotide Purification Cartridges (Applied Biosystems, Foster City, Calif.). DNA sequence analysis was performed on double stranded plasmid using Sequenase v2 (US Biochemical, Cleveland, Ohio) following the manufacturer's protocol.

Mutagenesis

Mutagenesis was performed by recombinant PCR (RPCR). Briefly, plasmid subclones containing the target region were linearized by digestion with a restriction enzyme cutting only within the sequence to be deleted. The vif/vpr subclone, p102-7, was linearized with PflMI for vif deletion and with AflII for vpr deletion. The nef/LTR subclone, p83-11 was linearized with XhoI for nef deletion and PmlI for NRE deletion. The absence of unique sites in the vpu deletion region, necessitated the use of partial digestion of p83-16 with SspI. Mutagenic primers are shown in Table 6 as underlined sequences. The vif and nef primers were designed with an additional nucleotide inserted at the site of deletion to create an in-frame stop codon. PCR reactions were made up to 100 μl with 200 ng of each primer, 200 μM dNTPs, 2.5 U AmpliTaq polymerase (Perkin-Elmer/Cetus, Norwalk, Conn.), buffer, template DNA, MgCl$_2$, and water and thermocycled 25 times (94° C./1 min, 50° C./1 min, 72° C./4 min+5 sec autoextension/cycle). A 15 μl aliquot was analyzed by agarose gel electrophoresis. Several concentrations of template (0.1–10 ng) and Mg$^{++}$ ion (1.5–3.5 mM) were tested for each template/primer set and the reaction with the lowest template concentration which still produced a visible amount of product was used for transformation. The remaining 85 μl of PCR amplified product was concentrated by precipitation with ethanol, redissolved in 10 μl water and used to transform 100 μl of library efficiency competent E. coli DH5α (BRL, Gaithersburg, Md.). Transformants were screened by plasmid size, restriction enzyme digestion and DNA sequence analysis. Clones containing no off-site mutations were selected and used to reconstruct proviral half-genome plasmids.

Reconstruction of mutant proviral genomes

The two subclones containing single deletions in vif and vpr and the subclone containing deletions in both vif and vpr were reconstituted to full length 5' half plasmids by replacement of the BspMI linker with the 5148 bp BspMI fragment from NL4-3 which contains 5'-LTR, gag and pol sequences. The Δvpu subclone was treated with NdeI and NcoI and ligated to the NdeI-NcoI fragment of p83-10 which contains env, nef and 3' LTR. The Δnef subclone was treated with BamHI and PmlI and ligated to the BamHI-PmlI fragment of p83-10 which contains vpu, env and vector sequences. The ΔnefΔNRE subclone was digested with BamHI and NruI and ligated to the BamHI-NruI fragment of p83-10 containing vpu, env and vector sequences. To reconstruct the ΔvpuΔnef and ΔvpuΔnefΔNRE mutants, Δvpu, Δnef and ΔnefΔNRE full-length clones were digested with EcoRI and BamHI. The Δvpu fragment was ligated to the Δnef or ΔnefΔNRE plasmid fragments to create the double and triple mutants.

Deletion Mutations in HIV Nonessential Genes

Deletion mutations were created in five regions of the HIV-1 NL4-3 proviral genome which are dispensable for viral replication in vitro. The use of 5'- and 3'-half genomic clones as intermediates simplified the mutagenesis, reduced the total number of clones to be constructed and sequenced, and alleviated biosafety concerns over the use of full-length, infectious cloned DNA. This half-genome approach has been of similar benefit in the maintenance and mutagenesis of SIVmac239. As designed, the deletions of NL4-3 shown in Table 6 and FIGS. 12A–12C were intended to parallel the deletions previously constructed in SIVmac239 as much as possible. However, the complex arrangement of the retrovirus genomes, overlapping reading frames, multiple splice acceptor and donor sites, RNA structural features, and regulatory sequences, made it difficult to achieve exact analogues in the two strains of virus.

Table 6 shows the sequences of deletion mutants. The upper three deletion mutations were constructed in plasmids containing the 5'-half of the HIV-1 NL4-3 genome. The lower three mutations were constructed in plasmids containing the 5'-half of the HIV-1 NL4-3 genome. The lower three mutations were constructed in plasmids containing the 3'-half of HIV-1 NL4-3. The numbering system is that of (Buckler, et al. *Genbank Accession No. M19921*, 1988). Underlined sequences correspond to the mutagenic oligonucleotides used in recombinant PCR. The predicted sizes of residual polypeptides are indicated to the right. Bold lettering refers to EcoRI sites at the junction of HIV-1 and vector sequences. Other 5'- or 3'-half derivative combination deletions constructed include ΔnefΔNRE, ΔvpuΔnef, and ΔvpuΔnefΔNRE (not shown). All mutants containing deletions of NRE had the additional nef deletion.

TABLE 6 vif deletion

| | 5090 5100 5110 5350 5360 5370 5380 | |
|---|---|---|
| pol | GATGAGGATTAACACATGGAAAAGATTAGTAAAA T GACCAACTAATTCATCTGCACTATTTTGATTG<br>CTACTCCTAATTGTGTACCTTTTCTAATCATTTT A CTGGTTGATTAAGTAGACGTGATAAAACTAAC<br>AspGluAspEnd | SEQ ID NO: 29 |
| | | full length |
| vif | .MetArgIle AsnThrTrpLysArgLeuValLys E nd | |
| | | 26 residues SEQ ID NO: 30 | vpr deletion

| | 5590 5600 5610 5620 5740 | |
|---|---|---|
| | AAGGGCCACAGAGGGAGCCATACAATGAATGGACACTAGAG TAATAAGAATTCGGTCACCATCCTCGC<br>TTCCCGGTGTCTCCCTCGGTATGTTACTTACCTGTGATCTC ATTATTCTTAAGCCAGTGGTAGGAGCG | SEQ ID NO: 31 |
| vif | LysGlyHisArgGlySerHisThrMetAsnGlyHisEnd | |
| | | full length SEQ ID NO: 32 |
| vpr | . . GlyProGlnArgGluProTyrAsnGluTrpThrLeuGlu End | |
| | | 21 residues SEQ ID NO: 33 | vif/vpr deletion

| | 5090 5100 5110 5740 | |
|---|---|---|
| pol | GATGAGGATTAACACATGGAAAAGATTAGTAAAA TAATAAGAATTCGGTCACCATCCTCGCTCACT<br>CTACTCCTAATTGTGTACCTTTTCTAATCATTTT ATTATTCTTAAGCCAGTGGTAGGAGCGAGTGA<br>AspGluAspEnd | SEQ ID NO: 34 |
| | | full length |
| vif | .MetArgIleAsnThrTrpLysArgLeuValLysEnd | |
| | | 26 residues SEQ ID NO: 30 | vpu deletion

| | 6040 6050 6060 6190 6200 6210 | |
|---|---|---|
| | TCTCTATCAAAGCAGTAAGTAGTACATGTAAT TTAATTGATAGACTAATAGAAAGAGCAGAAGAC<br>AGAGATAGTTTCGTCATTCATCATGTACATTA AATTAACTATCTGATTATCTTTCTCGTCTTCTG | SEQ ID NO: 35 |
| tat(exon1) | SerLeuSerLysXx | |
| | | full length SEQ ID NO: 36 |
| rev(exon1) | .LeuTyrGlnSerS | |
| | | full length SEQ ID NO: 37 |
| vpu | Il eEnd | |
| | | 0 residues | nef deletion

| | 8800 8810 8820 9050 9060 9070 | |
|---|---|---|
| | GGCAAGTGGTCAAAAAGTAGTGTGATTGGATG A TAGCCACTTTTTAAAAGAAAAGGGGGGACTGGA<br>CCGTTCACCAGTTTTTCATCACACTAACCTAC T ATCGGTGAAAAATTTTCTTTTCCCCCCTGACCT | SEQ ID NO: 38 |
| nef | GlyLysTrpSerLysSerSerValIleGlyEnd | |
| | | 12 residues SEQ ID NO: 39 |

NRE deletion

| | 9090 9100 9110 9390 9400 9410 | |
|---|---|---|
| | GCTAATTCACTCCCAAAGAAGACAAGATATCC CATCCGGAGTACTTCAAGAACTGCTGACATCGA<br>CGATTAAGTGAGGGTTTCTTCTGTTCTATAGG GTAGGCCTCATGAAGTTCTTGACGACTGTAGCT | SEQ ID NO: 40 |

All five HIV-1 genetic elements were mutated by substantial deletion and consequently have little possibility for reversion in vivo. In all cases, mutations were designed to terminate translation immediately after the deletion. Only in the case of vpu was it possible to cleanly mutate the initiating methionine codon. Therefore the 3 other reading frames can yield truncated N-terminal translation products whose length is indicated in Table 6. Mutations containing the NRE deletion were constructed only in the 3'-half plasmids. Due to the mechanism of retroviral replication, any alteration in the U3 region of the 3'-LTR is copied into the 5'-LTR after the first round of replication.

Mutagenesis was used for the construction of all mutants, as described above. While the use of Taq polymerase yielded the desired deletion mutations, it also produced a number of off-site mutations which significantly complicated the identification of correctly mutated subclones. Other thermostable polymerases with higher fidelity are now commercially available and these are probably more suitable for the construction of large, defined deletions. Nevertheless, all of the HIV-1 mutants used for the studies presented here contained only the indicated deletions and were shown to be free of any off-site, undesired mutations.

The four 5'-half and six 3'-half plasmids were combined in all permutations, resulting in a panel of 1 wild-type and 23 mutant viruses (Table 7). Virus stocks were prepared from plasmids by digestion of plasmid DNA halves with EcoRI restriction endonuclease, mixing the halves to produce mutant combinations, ligation of the mixed half genomes and finally, transfection into CEMx174 cells.

TABLE 7

REPLICATION OF WILD-TYPE AND DELETION MUTANT HIV-1 IN CEMx174 CELLS[a]

| | Days Post-Infection | Wild-Type 5'-half | Δvif | Δvpr | Δvif/Δvpr |
|---|---|---|---|---|---|
| Wild-Type 3'half | 8 | 1444 | 0.07 | 1217 | 0.11 |
| | 11 | 742 | 0.57 | 719 | 0.64 |
| | 28 | NT | 336 | NT | 492 |
| Δvpu | 8 | 911 | 0.94 | 583 | 0.08 |
| | 11 | 844 | 1.31 | 575 | 0.60 |
| | 28 | NT | 1.70 | NT | 1.24 |
| Δnef | 8 | 1192 | 0.43 | 714 | 0.09 |
| | 11 | 575 | 0.51 | 539 | 0.26 |
| | 28 | NT | 220 | NT | 10 |
| ΔnefΔNRE | 8 | 933 | 1.66 | 578 | 0.39 |
| | 11 | 456 | 2.92 | 275Δ3 | 0.41 |
| | 28 | NT | 23 | NT | 6.92 |
| ΔvpuΔnef | 8 | 472 | 0.01 | 195 | 0.01 |
| | 11 | 569 | 0.00 | 792 | 0.01 |
| | 28 | NT | 0.01 | NT | 0.01 |
| ΔvpuΔnefΔNRE | 8 | 411 | 0.04 | 24 | 0.05 |
| | 11 | 519 | 0.04 | 1194Δ4 | 0.00 |
| | 28 | NT | 0.05 | NT | 0.00 |

[a]Viruses constructed from 5'- and 3'- genomic halves were used to infect CEMx174 cells on day zero. Aliquots were taken at the time point listed and the amount of p24 gag antigen in the supernatant medium was measured. Values are expressed as ng/ml of p24 antigen.
NT — not tested.
Boxed regions indicate the Δ3 and Δ4 mutant viruses referred to in the test and in FIGS. 4, 5.

Cells

As described above, CEMx174 cells were maintained in RPMI 1640 medium (Gibco Laboratories, Grand Island, N.Y.) supplemented with 10% heat-inactivated fetal bovine serum (Gibco). Chimpanzee and human PBMC were prepared by banding whole heparinized blood on Lymphocyte Separation Media (Organon Teknika, Durham, N.C.) according to the manufacturer's recommendations.

Preparation of Virus Stocks

Wild-type and mutant 5' and 3'-half plasmids were linearized by EcoRI digestion. As described above, three μg of each were mixed, ligated and used to transfect CEMx174 using DEAE dextran. Supernatants from transfected cells were harvested at 18 days post-transfection (30 days for viruses with vif mutations) and stored in 0.5 ml aliquots at −70° C. The concentration of p24 gag antigen in these stocks was quantitated using a commercially available SIV antigen capture kit (Coulter Corp., Hialeah, Fla.) using known HIV-1 controls (Coulter) for the standard curve. The sensitivity of the SIV antigen capture kit was found to be approximately 3.6-fold greater for HIV-1 than for SIVmac.

Virus Replication in CEMx174 Cells

CEMx174 cells freshly split 1:3 the previous day were plated out in 48-well flat bottomed plates at $5 \times 10^5$ cells per well in one ml of medium. Cells were infected with an amount virus equivalent to 2.8 ng p24 gag antigen. The cells were split 1:3 approximately twice weekly if they had grown to a sufficient level; otherwise, the supernatant was replaced with an equal volume of fresh medium. Supernatant was sampled and assayed for HIV-1 p24 by antigen capture at the indicated intervals.

All mutant viruses with the exception of those containing deletions in the vif gene replicated with kinetics similar or identical to those of the wild-type parent virus, HIV-1 strain NL4-3 (Table 7). Even Δ4, with deletions in vpr, vpu, nef and upstream sequences of U3, replicated similar to the wild-type virus in these cells. Thus, the four regions deleted in Δ4 contribute little if anything to the ability of virus to replicate in CEMx174 cells in culture. Very small differences in replication rate may not have been detected with these assays.

Virus Replication in PBMC

Human and chimpanzee PBMC were activated for 72 hrs with 1 mg/ml phytohemagglutinin (sigma Chemical, St. Louis, Mo.), washed twice in serum-free medium and incubated with medium containing 10% interleukin-2 (Schiapparelli, Columbia, Md.), 20% fetal bovine serum, and 3.8 mg/ml β-mercaptoethanol (Sigma) overnight before plating at a concentration of $1 \times 10^6$ cells per ml in 48-well flat bottom plates. Activated PBMC were infected with virus stocks containing 40 ng (human PBMC) or 10 ng p24 (chimpanzee PBMC). All human PBMC infections were performed in duplicate. Supernatant was sampled and assayed for p24 gag by antigen capture at the indicated intervals. At the time of sampling, infected-cell supernatant was replaced with fresh medium.

Replication in Chimpanzee PBMC

Initial studies indicated that Δ3, containing deletions in vpr, nef and the NRE, and Δ4, containing deletions in vpr, vpu, nef and the NRE, replicated with kinetics similar to the wild-type parent virus HIV-1 strain NL4-3 (FIG. 13). These experiments were performed in duplicate using PBMC from two chimpanzees.

A more extensive investigation into the replication of mutant virus in chimpanzee PBMC utilized PBMC from ten chimpanzees that were infected in vitro with wild-type HIV-1 strain NL4-3 or Δ4 virus in parallel (FIG. 14). Additionally, PBMC from five of these chimpanzees were infected in parallel with Δ3. Production of Δ4 was lower by an average of 57% (61.9→25.6 ng/ml of p24 antigen) at day 7 in the ten parallel cultures but was not lower at the subsequent sampling times, day 11 and day 14. Eight of the ten parallel sets of cultures showed lower production of Δ4 at day 7, with a range of inhibition of 10–75%. Production of Δ3 was lower by an average of 90% at day 7 (20.4–2.0 ng/ml of p24 antigen) and 75% at day 11 (54.4→13.4 ng/ml of p24 antigen) in the five parallel cultures used for analysis of the replication of Δ3. Five of the five parallel sets of cultures showed lower production of Δ3 at days 7 and 11, with ranges of inhibition of 18–95% at day 7 and 5–90% at day 11. Within this subset of five chimpanzee PBMC samples, production of Δ4 was lower by an average of 63% (20.4→7.6 ng/ml of p24 antigen) at day 7 but was not lower at the subsequent sampling times; four of this subset of five cultures showed lower production of Δ4 at day 7. It is difficult to evaluate whether these small differences in replication rate may be significant. For example, it is not known whether different results may have been obtained with different stocks of virus prepared at different times or whether some individual chimpanzees may consistently show an effect of the deletions.

In any event, these results indicate that the deletions present in the combination mutants Δ3 and Δ4 do not have an appreciable effect on the ability of the virus to replicate in chimpanzee PBMC, a primary target of virus replication in vivo. While not directly addressed, it is likely from these studies that the individual deletions contained within these viruses also do not have a large effect on the ability of the virus to replicate in chimpanzee PBMC.

Replication in Human PBMC

Results of replication assays in human PBMC were found to be very similar to those in chimpanzee PBMC (FIG. 15). PBMC from two healthy volunteers were activated with PHA and IL-2 and infected with wild-type or mutant viruses in duplicate as described above. PBMC from one of the individuals was tested on two separate occasions. At appropriate intervals, virus supernatant was removed and assayed for p24 gag antigen using the Coulter antigen capture kit.

Of the viruses assayed, all except Δvif replicated with kinetics similar to the wild-type parent virus, NL4-3. Replication of Δvif in human PBMC was consistently and reproducibly below the limit of detection. Viruses tested for replication in human PBMC include the single deletion mutants Δvif, Δvpr, Δvpu and Δnef, as well as the combination deletion mutants ΔnefΔNRE and Δ4 (ΔvprΔvpuΔnefΔNRE). Thus, the genes vpr, vpu and nef and the upstream sequence of U3 in the LTR are not required for efficient replication of HIV-1 NL4-3 in primary human PBMC.

In summary, deletion of the vpu, vpr, and nef genes and the U3 upstream sequence (NRE), individually or in combinations, did not appreciably alter virus replication in either chimpanzee PBMC, human PBMC or in the B/T cell hybrid line, CEMx174. In contrast, deletion of the vif gene dramatically delayed virus replication in all three cell types.

This collection of HIV-1 deletion mutants will be useful for elucidating the functions of these genes for investigating antiviral immunity in animal models, and ultimately for production of vaccines against AIDS.

EXAMPLE 4

Properties of HIV Deletions Mutants in Chimpanzees

Wild type and two HIV deletion mutants, Δ3 and Δ4, were administered to chimpanzees. Viral replication as well as antibody production were evaluated in these chimpanzees.

Virus stock for inoculation was produced in CEMx174 cells as described above. Virus stocks were normalized based on concentration of p24 antigen (measured using the Coulter antigen capture kit).

Prior to administration of mutant virus to chimpanzees, a prescreening assay was carried out to test the ability of PBL from each candidate chimpanzee to support HIV-1 replication in vitro. Five chimpanzees matched for the ability to support HIV replication in PBL were chosen for further study.

Each chimpanzee was inoculated with virus intravenously. Each chimpanzee received a virus load corresponding to 500 ng of p24. Two chimpanzees were inoculated with wild type virus; one chimpanzee was inoculated with the Δ3 mutant; and two chimpanzees were inoculated with the Δ4 mutant.

Following inoculation, blood was drawn from each chimpanzee at 1, 2, 4, 6, 8, and 12 weeks. To characterize the response of each chimpanzee to the vaccine strain used as an inoculant, levels of p24 antigen in blood plasm were measured as described above. Plasma antigenemia is shown in Table 8. Chimpanzee #753 developed plasma antigenemia by week 2, whereas no plasma antigenemia was observed in chimpanzees inoculated with either the Δ3 or the Δ4 mutant.

TABLE 8

PLASMA ANTIGENEMIA IN CHIMPANZEES

| | | pg/ml p24 antigen | | | |
|---|---|---|---|---|---|
| CHIMP | VIRUS | WEEK 1 | WEEK 2 | WEEK 4 | WEEK 6 |
| 753 | WT | 0 | 10 | 31 | 0 |
| 993 | WT | 0 | 0 | 0 | 0 |
| 1143 | Δ3 | 0 | 0 | 0 | 0 |
| 1216 | Δ4 | 0 | 0 | 0 | 0 |
| 1250 | Δ4 | 0 | 0 | 0 | 0 |

TABLE 9

HIV RECOVERY FROM CHIMPANZEES #'s OF PBMC NEEDED TO RECOVER HIV

| CHIMP | INFECTION | WEEK 1 | WEEK 2 | WEEK 4 | WEEK 6 | WEEK 8 | WEEK 12 |
|---|---|---|---|---|---|---|---|
| 753 | WT | $10^6$ | 222,222 | 24,691 | 4,115 | 74,074 | 222,222 |
| 993 | WT | $>10^7$ | $10^7$ | 333,333 | 111,111 | $10^6$ | 222,222 |
| 1143 | Δ3 | $>10^7$ | $>10^7$ | $>10^7$ | $>10^7$ | $>10^7$ | $>10^7$ |
| 1216 | Δ4 | $>10^7$ | $10^6$ | $10^6$ | 333,333 | $10^7$ | $>10^7$ |
| 1250 | Δ4 | $>10^7$ | $>10^7$ | $10^7$ | $10^7$ | $>10^7$ | $>10^7$ |

Viral replication in each chimpanzee was tested by removing PBMC and co-culturing these cells with CEMx174 cells in vitro to evaluate virus production. The numbers of PBMC needed to recover virus is shown in Table 9. Virus could be recovered from each experimental chimpanzee, indicating that each virus tested was infective. Approximately 10–100 fold more PBMC were needed to recover virus from chimpanzees inoculated with Δ3 or Δ4 compared to the amount required to recover virus from chimpanzees inoculated with the wild type virus. Quantitative competitive PCR was used to show that chimpanzees that were inoculated with wild type HIV-1 consistently had much higher levels of viral RNA, usually greater than 100 times more viral RNA, in their plasma than chimpanzees that received Δ3 or Δ4 (see Table 10). These data indicate that the Δ3 and Δ4 deletion mutant viruses demonstrate decreased replication in chimpanzees.

TABLE 10

| Chimpanzee | Virus | Week 1 | Week 2 | Week 4 | Week 8 | Week 12 | Week 17 |
|---|---|---|---|---|---|---|---|
| 753 | WT | ~100 | 127,000 | 88,200 | 27,800 | 5,000 | 1,700 |
| 993 | WT | <300 | 7,400 | 49,200 | 24,400 | 6,000 | 3,600 |
| 1143 | Δ3 | <300 | <300 | <200 | <400 | <200 | <200 |
| 1216 | Δ4 | <400 | <600 | <300 | <200 | <300 | <300 |
| 1250 | Δ4 | <200 | <200 | <300 | <100 | <400 | <400 |

Antibody response to vaccine strains was also measured, as shown in FIG. 16. The presence of HIV-1-specific antibodies in the plasma of each chimpanzee was evaluated using ELISA. Each chimpanzee produced virus-specific antibodies. Compared to chimpanzees inoculated with the wild type virus, the kinetics of antibody production was slightly delayed in chimpanzees inoculated with each of the deletion mutants. The level of antibody production in chimpazees inoculated with Δ3 or Δ4 was also lower than that in chimpanzees inoculated with the wild type virus. These data are consistent with the observation that the deletion mutants are attenuated and demonstrate a lower rate of in vivo replication compared to the wild type virus.

What is claimed is:

1. An antigenic composition comprising isolated primate lentivirus whose genome contains an engineered non-revertible null mutation in the nef gene, or an infectious DNA clone thereof, in a pharmaceutically acceptable carrier.

2. The antigenic composition of claim 1, wherein said primate lentivirus further comprises engineered non-revertible null mutations in one or more nonessential genetic elements selected from the group consisting of vif, vpr, vpx, vpu, Negative Regulatory Element, nuclear factor κB-binding element, or Sp1 binding element.

3. The antigenic composition of claim 1, wherein said primate lentivirus is infectious, replication-competent, and non-pathogenic.

4. The antigenic composition of claim 1, wherein said primate lentivirus is derived from human immunodeficiency virus.

5. The antigenic composition of claim 4, wherein said primate lentivirus is derived from HIV-1.

6. The antigenic composition of claim 1, wherein said primate lentivirus is derived from simian immunodeficiency virus.

7. The antigenic composition of claim 6, wherein said primate lentivirus is derived from SIVmac.

8. The antigenic composition of claim 7, wherein said primate lentivirus is derived from the DNA clones deposited with the ATCC and designated No. 68364 and No. 68365.

9. The antigenic composition of claim 1, wherein said primate lentivirus genome further comprises an engineered non-revertible null mutation in the Negative Regulatory Element sequence.

10. The antigenic composition of claim 9, wherein said primate lentivirus genome further comprises an engineered non-revertible null mutation in the vpu or vpx gene sequence.

11. The antigenic composition of claim 1, wherein said primate lentivirus genome further comprises an engineered non-revertible null mutation in the vpr gene sequence.

12. The antigenic composition of claim 11, wherein said primate lentivirus genome further comprises an engineered non-revertible null mutation in the vpu or vpx gene sequence.

13. The antigenic composition of claim 1, wherein said primate lentivirus genome further comprises an engineered non-revertible null mutation in the vpx gene sequence.

14. The antigenic composition of claim 1, wherein said primate lentivirus genome further comprises an engineered non-revertible null mutation in the vpu gene sequence.

15. The antigenic composition of claim 7, wherein said primate lentivirus is derived from SIVmac239ΔnefΔNegative Regulatory Element.

16. The antigenic composition of claim 15, wherein said primate lentivirus further comprises an engineered non-revertible null mutation in the vpx gene sequence.

17. The antigenic composition of claim 7, wherein said primate lentivirus is derived from SIVmac239ΔvprΔnef.

18. The antigenic composition of claim 17, wherein said primate lentivirus further comprises an engineered non-revertible null mutation in the vpx gene sequence.

19. The antigenic composition of claim 7, wherein said primate lentivirus is derived from SIVmac239Δ3.

20. The antigenic composition of claim 7, wherein said primate lentivirus is derived from SIVmac239Δ4.

21. The antigenic composition of claim 20, wherein said primate lentivirus further comprises engineered non-revertible null mutations in one or more non-essential genetic elements selected from the group consisting of vif, vpr, vpx, vpu, Negative Regulatory Element, nuclear factor κB-binding element, or Sp1 binding element.

22. The antigenic composition of claim 5, wherein said primate lentivirus is derived from HIV-1ΔnefΔNegative Regulatory Element.

23. The antigenic composition of claim 22, wherein said primate lentivirus further comprises an engineered non-revertible null mutation in the vpu gene sequence.

24. The antigenic composition of claim 5, wherein said primate lentivirus is derived from HIV-1 ΔvprΔnef.

25. The antigenic composition of claim 24, wherein said primate lentivirus further comprises an engineered non-revertible null mutation in the vpu gene sequence.

26. The antigenic composition of claim 5, wherein said primate lentivirus is derived from HIV-1Δ3.

27. The antigenic composition of claim 5, wherein said primate lentivirus is derived from HIV-1Δ4.

28. The antigenic composition of claim 5, wherein said primate lentivirus further comprises engineered non-revertible null mutations in one or more non-essential genetic elements selected from the group consisting of vif, vpr, vpx, vpu, Negative Regulatory Element, nuclear factor κB-binding element, or Sp1 binding element.

29. A method of producing an antigenic composition comprising:

transfecting cultured primate cells with primate lentiviral nucleic acid containing an engineered non-revertible null mutation of the nef gene, isolating lentivirus whose genome contains said mutation of the nef gene, and compounding said virus into a pharmaceutically acceptable antigenic compositions.

30. The method of claim 29, wherein said lentiviral nucleic acid further comprises an engineered non-revertible null mutation in the Negative Regulatory Element sequence.

31. The method of claim 29, wherein said lentiviral nucleic acid further comprises an engineered non-revertible null mutation in the vpr gene sequence.

32. The method of claim 29, wherein said lentiviral nucleic acid further comprises an engineered non-revertible null mutation in the vpx gene sequence.

33. The method of claim 29, wherein said primate lentiviral nucleic acid further comprises an engineered non-revertible null mutation in the vpu gene sequence.

* * * * *

SEQUENCE LISTING ( 1 ) GENERAL INFORMATION:

( i i i ) NUMBER OF SEQUENCES: 57

( 2 ) INFORMATION FOR SEQ ID NO: 1:

( i ) SEQUENCE CHARACTERISTICS:
        ( A ) LENGTH: 35
        ( B ) TYPE: nucleic acid
        ( C ) STRANDEDNESS: single
        ( D ) TOPOLOGY: linear ( x i ) SEQUENCE DESCRIPTION: SEQ ID NO: 1:

TCCAGGACTA GCATAAATTT GATCCTCGCT TGCTA 35

( 2 ) INFORMATION FOR SEQ ID NO: 2:

( i ) SEQUENCE CHARACTERISTICS:
        ( A ) LENGTH: 35
        ( B ) TYPE: nucleic acid
        ( C ) STRANDEDNESS: single
        ( D ) TOPOLOGY: linear ( x i ) SEQUENCE DESCRIPTION: SEQ ID NO: 2:

TAGCAAGCGA GGATCAAATT TATGCTAGTC CTGGA 35

( 2 ) INFORMATION FOR SEQ ID NO: 3:

( i ) SEQUENCE CHARACTERISTICS:
        ( A ) LENGTH: 30
        ( B ) TYPE: nucleic acid
        ( C ) STRANDEDNESS: single
        ( D ) TOPOLOGY: linear ( x i ) SEQUENCE DESCRIPTION: SEQ ID NO: 3:

ATACTGGCAT GATGATTGAT CCTCGCTTGC  30

( 2 ) INFORMATION FOR SEQ ID NO: 4:

( i ) SEQUENCE CHARACTERISTICS:
( A ) LENGTH: 30
( B ) TYPE: nucleic acid
( C ) STRANDEDNESS: single
( D ) TOPOLOGY: linear ( x i ) SEQUENCE DESCRIPTION: SEQ ID NO: 4:

GCAAGCGAGG ATCAATCATC ATGCCAGTAT  30

( 2 ) INFORMATION FOR SEQ ID NO: 5:

( i ) SEQUENCE CHARACTERISTICS:
( A ) LENGTH: 9709
( B ) TYPE: nucleic acid
( C ) STRANDEDNESS: single
( D ) TOPOLOGY: linear ( x i ) SEQUENCE DESCRIPTION: SEQ ID NO: 5:

```
TGGAAGGGCT AATTTGGTCC CAAAAAAGAC AAGAGATCCT TGATCTGTGG ATCTACCACA   60
CACAAGGCTA CTTCCCTGAT TGGCAGAACT ACACACCAGG GCCAGGGATC AGATATCCAC  120
TGACCTTTGG ATGGTGCTTC AAGTTAGTAC CAGTTGAACC AGAGCAAGTA GAAGAGGCCA  180
AATAAGGAGA GAAGAACAGC TTGTTACACC CTATGAGCCA GCATGGGATG GAGGACCCGG  240
AGGGAGAAGT ATTAGTGTGG AAGTTTGACA GCCTCCTAGC ATTTCGTCAC ATGGCCCGAG  300
AGCTGCATCC GGAGTACTAC AAAGACTGCT GACATCGAGC TTTCTACAAG GGACTTTCCG  360
CTGGGGACTT TCCAGGGAGG TGTGGCCTGG GCGGGACTGG GGAGTGGCGA GCCCTCAGAT  420
GCTACATATA AGCAGCTGCT TTTTGCCTGT ACTGGGTCTC TCTGGTTAGA CCAGATCTGA  480
GCCTGGGAGC TCTCTGGCTA ACTAGGGAAC CCACTGCTTA AGCCTCAATA AAGCTTGCCT  540
TGAGTGCTCA AAGTAGTGTG TGCCCGTCTG TTGTGTGACT CTGGTAACTA GAGATCCCTC  600
AGACCCTTTT AGTCAGTGTG GAAAATCTCT AGCAGTGGCG CCCGAACAGG GACTTGAAAG  660
CGAAAGTAAA GCCAGAGGAG ATCTCTCGAC GCAGGACTCG GCTTGCTGAA GCGCGCACGG  720
CAAGAGGCGA GGGGCGGCGA CTGGTGAGTA CGCCAAAAAT TTTGACTAGC GGAGGCTAGA  780
AGGAGAGAGA TGGGTGCGAG AGCGTCGGTA TTAAGCGGGG GAGAATTAGA TAAATGGGAA  840
AAAATTCGGT TAAGGCCAGG GGGAAAGAAA CAATATAAAC TAAAACATAT AGTATGGGCA  900
AGCAGGGAGC TAGAACGATT CGCAGTTAAT CCTGGCCTTT TAGAGACATC AGAAGGCTGT  960
AGACAAATAC TGGGACAGCT ACAACCATCC CTTCAGACAG GATCAGAAGA ACTTAGATCA 1020
TTATATAATA CAATAGCAGT CCTCTATTGT GTGCATCAAA GGATAGATGT AAAAGACACC 1080
AAGGAAGCCT TAGATAAGAT AGAGGAAGAG CAAAACAAAA GTAAGAAAAA GGCACAGCAA 1140
GCAGCAGCTG ACACAGGAAA CAACAGCCAG GTCAGCCAAA ATTACCCTAT AGTGCAGAAC 1200
CTCCAGGGGC AAATGGTACA TCAGGCCATA TCACCTAGAA CTTTAAATGC ATGGGTAAAA 1260
GTAGTAGAAG AGAAGGCTTT CAGCCCAGAA GTAATACCCA TGTTTTCAGC ATTATCAGAA 1320
GGAGCCACCC CACAAGATTT AAATACCATG CTAAACACAG TGGGGGGACA TCAAGCAGCC 1380
ATGCAAATGT TAAAAGAGAC CATCAATGAG GAAGCTGCAG AATGGGATAG ATTGCATCCA 1440
GTGCATGCAG GGCCTATTGC ACCAGGCCAG ATGAGAGAAC CAAGGGGAAG TGACATAGCA 1500
GGAACTACTA GTACCCTTCA GGAACAAATA GGATGGATGA CACATAATCC ACCTATCCCA 1560
```

```
GTAGGAGAAA TCTATAAAAG ATGGATAATC CTGGGATTAA ATAAATAGT  AAGAATGTAT     1620
AGCCCTACCA GCATTCTGGA CATAAGACAA GGACCAAAGG AACCCTTTAG ACTATGTA      1680
GACCGATTCT ATAAAACTCT AAGAGCCGAG CAAGCTTCAC AAGAGGTAAA AAATTGGATG    1740
ACAGAAACCT TGTTGGTCCA AAATGCGAAC CCAGATTGTA AGACTATTTT AAAAGCATTG    1800
GGACCAGGAG CGACACTAGA AGAAATGATG ACAGCATGTC AGGGAGTGGG GGGACCCGGC    1860
CATAAAGCAA GAGTTTTGGC TGAAGCAATG AGCCAAGTAA CAAATCCAGC TACCATAATG    1920
ATACAGAAAG GCAATTTTAG GAACCAAAGA AAGACTGTTA AGTGTTTCAA TTGTGGCAAA    1980
GAAGGGCACA TAGCCAAAAA TTGCAGGGCC CCTAGGAAAA AGGGCTGTTG GAAATGTGGA    2040
AAGGAAGGAC ACCAAATGAA AGATTGTACT GAGAGACAGG CTAATTTTTT AGGGAAGATC    2100
TGGCCTTCCC ACAAGGGAAG GCCAGGGAAT TTTCTTCAGA GCAGACCAGA GCCAACAGCC    2160
CCACCAGAAG AGAGCTTCAG GTTTGGGGAA GAGACAACAA CTCCCTCTCA GAAGCAGGAG    2220
CCGATAGACA AGGAACTGTA TCCTTTAGCT TCCCTCAGAT CACTCTTTGG CAGCGACCCC    2280
TCGTCACAAT AAAGATAGGG GGGCAATTAA AGGAAGCTCT ATTAGATACA GGAGCAGATG    2340
ATACAGTATT AGAAGAAATG AATTTGCCAG GAAGATGGAA ACCAAAAATG ATAGGGGGAA    2400
TTGGAGGTTT TATCAAAGTA GGACAGTATG ATCAGATACT CATAGAAATC TGCGGACATA    2460
AAGCTATAGG TACAGTATTA GTAGGACCTA CACCTGTCAA CATAATTGGA AGAAATCTGT    2520
TGACTCAGAT TGGCTGCACT TTAAATTTTC CCATTAGTCC TATTGAGACT GTACCAGTAA    2580
AATTAAAGCC AGGAATGGAT GGCCCAAAAG TTAAACAATG GCCATTGACA GAAGAAAAAA    2640
TAAAAGCATT AGTAGAAATT TGTACAGAAA TGGAAAAGGA AGGAAAAATT TCAAAAATTG    2700
GGCCTGAAAA TCCATACAAT ACTCCAGTAT TTGCCATAAA GAAAAAAGAC AGTACTAAAT    2760
GGAGAAAATT AGTAGATTTC AGAGAACTTA ATAAGAGAAC TCAAGATTTC TGGGAAGTTC    2820
AATTAGGAAT ACCACATCCT GCAGGGTTAA AACAGAAAAA ATCAGTAACA GTACTGGATG    2880
TGGGCGATGC ATATTTTTCA GTTCCCTTAG ATAAAGACTT CAGGAAGTAT ACTGCATTTA    2940
CCATACCTAG TATAAACAAT GAGACACCAG GGATTAGATA TCAGTACAAT GTGCTTCCAC    3000
AGGGATGGAA AGGATCACCA GCAATATTCC AGTGTAGCAT GACAAAAATC TTAGAGCCTT    3060
TTAGAAAACA AAATCCAGAC ATAGTCATCT ATCAATACAT GGATGATTTG TATGTAGGAT    3120
CTGACTTAGA AATAGGGCAG CATAGAACAA AAATAGAGGA ACTGAGACAA CATCTGTTGA    3180
GGTGGGGATT TACCACACCA GACAAAAAAC ATCAGAAAGA ACCTCCATTC CTTTGGATGG    3240
GTTATGAACT CCATCCTGAT AAATGGACAG TACAGCCTAT AGTGCTGCCA GAAAAGGACA    3300
GCTGGACTGT CAATGACATA CAGAAATTAG TGGGAAAATT GAATTGGGCA AGTCAGATTT    3360
ATGCAGGGAT TAAAGTAAGG CAATTATGTA AACTTCTTAG GGGAACCAAA GCACTAACAG    3420
AAGTAGTACC ACTAACAGAA GAAGCAGAGC TAGAACTGGC AGAAAACAGG GAGATTCTAA    3480
AAGAACCGGT ACATGGAGTG TATTATGACC CATCAAAAGA CTTAATAGCA GAAATACAGA    3540
AGCAGGGGCA AGGCCAATGG ACATATCAAA TTTATCAAGA GCCATTTAAA AATCTGAAAA    3600
CAGGAAAATA TGCAAGAATG AAGGGTGCCC ACACTAATGA TGTGAAACAA TTAACAGAGG    3660
CAGTACAAAA AATAGCCACA GAAAGCATAG TAATATGGGG AAAGACTCCT AAATTTAAAT    3720
TACCCATACA AAAGGAAACA TGGGAAGCAT GGTGGACAGA GTATTGGCAA GCCACCTGGA    3780
TTCCTGAGTG GGAGTTTGTC AATACCCCTC CCTTAGTGAA GTTATGGTAC CAGTTAGAGA    3840
AAGAACCCAT AATAGGAGCA GAAACTTTCT ATGTAGATGG GGCAGCCAAT AGGGAAACTA    3900
AATTAGGAAA AGCAGGATAT GTAACTGACA GAGGAAGACA AAAAGTTGTC CCCCTAACGG    3960
```

```
ACACAACAAA TCAGAAGACT GAGTTACAAG CAATTCATCT AGCTTTGCAG GATTCGGGAT    4020
TAGAAGTAAA CATAGTGACA GACTCACAAT ATGCATTGGG AATCATTCAA GCACAACCAG    4080
ATAAGAGTGA ATCAGAGTTA GTCAGTCAAA TAATAGAGCA GTTAATAAAA AAGGAAAAAG    4140
TCTACCTGGC ATGGGTACCA GCACACAAAG GAATTGGAGG AAATGAACAA GTAGATGGGT    4200
TGGTCAGTGC TGGAATCAGG AAAGTACTAT TTTTAGATGG AATAGATAAG CCCAAGAAG     4260
AACATGAGAA ATATCACAGT AATTGGAGAG CAATGGCTAG TGATTTTAAC CTACCACCTG    4320
TAGTAGCAAA AGAAATAGTA GCCAGCTGTG ATAAATGTCA GCTAAAAGGG GAAGCCATGC    4380
ATGGACAAGT AGACTGTAGC CCAGGAATAT GGCAGCTAGA TTGTACACAT TTAGAAGGAA    4440
AAGTTATCTT GGTAGCAGTT CATGTAGCCA GTGGATATAT AGAAGCAGAA GTAATTCCAG    4500
CAGAGACAGG GCAAGAAACA GCATACTTCC TCTTAAAATT AGCAGGAAGA TGGCCAGTAA    4560
AAACAGTACA TACAGACAAT GGCAGCAATT TCACCAGTAC TACAGTTAAG GCCGCCTGTT    4620
GGTGGGCGGG GATCAAGCAG GAATTTGGCA TTCCCTACAA TCCCCAAAGT CAAGGAGTAA    4680
TAGAATCTAT GAATAAAGAA TTAAAGAAAA TTATAGGACA GGTAAGAGAT CAGGCTGAAC    4740
ATCTTAAGAC AGCAGTACAA ATGGCAGTAT TCATCCACAA TTTTAAAAGA AAAGGGGGGA    4800
TTGGGGGGTA CAGTGCAGGG GAAAGAATAG TAGACATAAT AGCAACAGAC ATACAAACTA    4860
AAGAATTACA AAAACAAATT ACAAAAATTC AAAATTTTCG GGTTTATTAC AGGGACAGCA    4920
GAGATCCAGT TTGGAAAGGA CCAGCAAAGC TCCTCTGGAA AGGTGAAGGG GCAGTAGTAA    4980
TACAAGATAA TAGTGACATA AAAGTAGTGC CAAGAAGAAA AGCAAAGATC ATCAGGGATT    5040
ATGGAAAACA GATGGCAGGT GATGATTGTG TGGCAAGTAG ACAGGATGAG GATTAACACA    5100
TGGAAAAGAT TAGTAAAACA CCATATGTAT ATTTCAAGGA AAGCTAAGGA CTGGTTTTAT    5160
AGACATCACT ATGAAAGTAC TAATCCAAAA ATAAGTTCAG AAGTACACAT CCCACTAGGG    5220
GATGCTAAAT TAGTAATAAC AACATATTGG GGTCTGCATA CAGGAGAAAG AGACTGGCAT    5280
TTGGGTCAGG GAGTCTCCAT AGAATGGAGG AAAAAGAGAT ATAGCACACA AGTAGACCCT    5340
GACCTAGCAG ACCAACTAAT TCATCTGCAC TATTTTGATT GTTTTTCAGA ATCTGCTATA    5400
AGAAATACCA TATTAGGACG TATAGTTAGT CCTAGGTGTG AATATCAAGC AGGACATAAC    5460
AAGGTAGGAT CTCTACAGTA CTTGGCACTA GCAGCATTAA TAAAACCAAA ACAGATAAAG    5520
CCACCTTTGC CTAGTGTTAG GAAACTGACA GAGGACAGAT GGAACAAGCC CCAGAAGACC    5580
AAGGGCCACA GAGGGAGCCA TACAATGAAT GGACACTAGA GCTTTTAGAG GAACTTAAGA    5640
GTGAAGCTGT TAGACATTTT CCTAGGATAT GGCTCCATAA CTTAGGACAA CATATCTATG    5700
AAACTTACGG GGATACTTGG GCAGGAGTGG AAGCCATAAT AAGAATTCTG CAACAACTGC    5760
TGTTTATCCA TTTCAGAATT GGGTGTCGAC ATAGCAGAAT AGGCGTTACT CGACAGAGGA    5820
GAGCAAGAAA TGGAGCCAGT AGATCCTAGA CTAGAGCCCT GGAAGCATCC AGGAAGTCAG    5880
CCTAAAACTG CTTGTACCAA TTGCTATTGT AAAAAGTGTT GCTTTCATTG CCAAGTTTGT    5940
TTCATGACAA AAGCCTTAGG CATCTCCTAT GGCAGGAAGA AGCGGAGACA GCGACGAAGA    6000
GCTCATCAGA ACAGTCAGAC TCATCAAGCT TCTCTATCAA AGCAGTAAGT AGTACATGTA    6060
ATGCAACCTA TAATAGTAGC AATAGTAGCA TTAGTAGTAG CAATAATAAT AGCAATAGTT    6120
GTGTGGTCCA TAGTAATCAT AGAATATAGG AAAATATTAA GACAAAGAAA AATAGACAGG    6180
TTAATTGATA GACTAATAGA AAGAGCAGAA GACAGTGGCA ATGAGAGTGA AGGAGAAGTA    6240
TCAGCACTTG TGGAGATGGG GGTGGAAATG GGGCACCATG CTCCTTGGGA TATTGATGAT    6300
CTGTAGTGCT ACAGAAAAAT TGTGGGTCAC AGTCTATTAT GGGGTACCTG TGTGGAAGGA    6360
```

```
AGCAACCACC ACTCTATTTT GTGCATCAGA TGCTAAAGCA TATGATACAG AGGTACATAA      6420
TGTTTGGGCC ACACATGCCT GTGTACCCAC AGACCCCAAC CCACAAGAAG TAGTATTGGT      6480
AAATGTGACA GAAAATTTTA ACATGTGGAA AAATGACATG GTAGAACAGA TGCATGAGGA      6540
TATAATCAGT TTATGGGATC AAAGCCTAAA GCCATGTGTA AAATTAACCC CACTCTGTGT      6600
TAGTTTAAAG TGCACTGATT TGAAGAATGA TACTAATACC AATAGTAGTA GCGGGAGAAT      6660
GATAATGGAG AAAGGAGAGA TAAAAAACTG CTCTTTCAAT ATCAGCACAA GCATAAGAGA      6720
TAAGGTGCAG AAAGAATATG CATTCTTTTA TAAACTTGAT ATAGTACCAA TAGATAATAC      6780
CAGCTATAGG TTGATAAGTT GTAACACCTC AGTCATTACA CAGGCCTGTC CAAAGGTATC      6840
CTTTGAGCCA ATTCCCATAC ATTATTGTGC CCCGGCTGGT TTTGCGATTC TAAAATGTAA      6900
TAATAAGACG TTCAATGGAA CAGGACCATG TACAAATGTC AGCACAGTAC AATGTACACA      6960
TGGAATCAGG CCAGTAGTAT CAACTCAACT GCTGTTAAAT GGCAGTCTAG CAGAAGAAGA      7020
TGTAGTAATT AGATCTGCCA ATTCACAGA CAATGCTAAA ACCATAATAG TACAGCTGAA       7080
CACATCTGTA GAAATTAATT GTACAAGACC CAACAACAAT ACAAGAAAAA GTATCCGTAT      7140
CCAGAGGGGA CCAGGGAGAG CATTTGTTAC AATAGGAAAA ATAGGAAATA TGAGACAAGC      7200
ACATTGTAAC ATTAGTAGAG CAAAATGGAA TGCCACTTTA AAACAGATAG CTAGCAAATT      7260
AAGAGAACAA TTTGGAAATA ATAAAACAAT AATCTTTAAG CAATCCTCAG GAGGGGACCC      7320
AGAAATTGTA ACGCACAGTT TTAATTGTGG AGGGGAATTT TTCTACTGTA ATTCAACACA      7380
ACTGTTTAAT AGTACTTGGT TTAATAGTAC TTGGAGTACT GAAGGGTCAA ATAACACTGA      7440
AGGAAGTGAC ACAATCACAC TCCCATGCAG AATAAAACAA TTTATAAACA TGTGGCAGGA      7500
AGTAGGAAAA GCAATGTATG CCCCTCCCAT CAGTGGACAA ATTAGATGTT CATCAAATAT      7560
TACTGGGCTG CTATTAACAA GAGATGGTGG TAATAACAAC AATGGGTCCG AGATCTTCAG      7620
ACCTGGAGGA GGCGATATGA GGGACAATTG GAGAAGTGAA TTATATAAAT ATAAAGTAGT      7680
AAAAATTGAA CCATTAGGAG TAGCACCCAC CAAGGCAAAG AGAAGAGTGG TGCAGAGAGA      7740
AAAAAGAGCA GTGGGAATAG GAGCTTTGTT CCTTGGGTTC TTGGGAGCAG CAGGAAGCAC      7800
TATGGGCTGC ACGTCAATGA CGCTGACGGT ACAGGCCAGA CAATTATTGT CTGATATAGT      7860
GCAGCAGCAG AACAATTTGC TGAGGGCTAT TGAGGCGCAA CAGCATCTGT TGCAACTCAC      7920
AGTCTGGGGC ATCAAACAGC TCCAGGCAAG AATCCTGGCT GTGGAAAGAT ACCTAAAGGA      7980
TCAACAGCTC CTGGGGATTT GGGGTTGCTC TGGAAAACTC ATTTGCACCA CTGCTGTGCC      8040
TTGGAATGCT AGTTGGAGTA ATAAATCTCT GGAACAGATT TGGAATAACA TGACCTGGAT      8100
GGAGTGGGAC AGAGAAATTA ACAATTACAC AAGCTTAATA CACTCCTTAA TTGAAGAATC      8160
GCAAAACCAG CAAGAAAAGA ATGAACAAGA ATTATTGGAA TTAGATAAAT GGGCAAGTTT      8220
GTGGAATTGG TTTAACATAA CAAATTGGCT GTGGTATATA AAATTATTCA TAATGATAGT      8280
AGGAGGCTTG GTAGGTTTAA GAATAGTTTT TGCTGTACTT TCTATAGTGA ATAGAGTTAG      8340
GCAGGGATAT TCACCATTAT CGTTTCAGAC CCACCTCCCA ATCCCGAGGG GACCCGACAG      8400
GCCCGAAGGA ATAGAAGAAG AAGGTGGAGA GAGAGACAGA GACAGATCCA TTCGATTAGT      8460
GAACGGATCC TTAGCACTTA TCTGGGACGA TCTGCGGAGC CTGTGCCTCT TCAGCTACCA      8520
CCGCTTGAGA GACTTACTCT TGATTGTAAC GAGGATTGTG GAACTTCTGG GACGCAGGGG      8580
GTGGGAAGCC CTCAAATATT GGTGGAATCT CCTACAGTAT GGAGTCAGG AACTAAAGAA       8640
TAGTGCTGTT AACTTGCTCA ATGCCACAGC CATAGCAGTA GCTGAGGGGA CAGATAGGGT      8700
TATAGAAGTA TTACAAGCAG CTTATAGAGC TATTCGCCAC ATACCTAGAA GAATAAGACA      8760
```

| | | | | | |
|---|---|---|---|---|---|
| GGGCTTGGAA | AGGATTTTGC | TATAAGATGG | GTGGCAAGTG | GTCAAAAAGT | AGTGTGATTG | 8820
| GATGGCCTGC | TGTAAGGGAA | AGAATGAGAC | GAGCTGAGCC | AGCAGCAGAT | GGGGTGGGAG | 8880
| CAGTATCTCG | AGACCTAGAA | AAACATGGAG | CAATCACAAG | TAGCAATACA | GCAGCTAACA | 8940
| ATGCTGCTTG | TGCCTGGCTA | GAAGCACAAG | AGGAGGAAGA | GGTGGGTTTT | CCAGTCACAC | 9000
| CTCAGGTACC | TTTAAGACCA | ATGACTTACA | AGGCAGCTGT | AGATCTTAGC | CACTTTTTAA | 9060
| AAGAAAAGGG | GGGACTGGAA | GGGCTAATTC | ACTCCCAAAG | AAGACAAGAT | ATCCTTGATC | 9120
| TGTGGATCTA | CCACACACAA | GGCTACTTCC | CTGATTGGCA | GAACTACACA | CCAGGGCCAG | 9180
| GGGTCAGATA | TCCACTGACC | TTTGGATGGT | GCTACAAGCT | AGTACCAGTT | GAGCCAGATA | 9240
| AGGTAGAAGA | GGCCAATAAA | GGAGAGAACA | CCAGCTTGTT | ACACCCTGTG | AGCCTGCATG | 9300
| GAATGGATGA | CCCTGAGAGA | GAAGTGTTAG | AGTGGAGGTT | TGACAGCCGC | CTAGCATTTC | 9360
| ATCACGTGGC | CCGAGAGCTG | CATCCGGAGT | ACTTCAAGAA | CTGCTGACAT | CGAGCTTGCT | 9420
| ACAAGGGACT | TTCCGCTGGG | GACTTTCCAG | GGAGGCGTGG | CCTGGGCGGG | ACTGGGGAGT | 9480
| GGCGAGCCCT | CAGATGCTGC | ATATAAGCAG | CTGCTTTTTG | CCTGTACTGG | GTCTCTCTGG | 9540
| TTAGACCAGA | TCTGAGCCTG | GGAGCTCTCT | GGCTAACTAG | GGAACCCACT | GCTTAAGCCT | 9600
| CAATAAAGCT | TGCCTTGAGT | GCTTCAAGTA | GTGTGTGCCC | GTCTGTTGTG | TGACTCTGGT | 9660
| AACTAGAGAT | CCCTCAGACC | CTTTAGTCA | GTGTGGAAAA | TCTCTAGCA | | 9709

( 2 ) INFORMATION FOR SEQ ID NO: 6:

( i ) SEQUENCE CHARACTERISTICS:
        ( A ) LENGTH: 33
        ( B ) TYPE: nucleic acid
        ( C ) STRANDEDNESS: single
        ( D ) TOPOLOGY: linear ( x i ) SEQUENCE DESCRIPTION: SEQ ID NO: 6:

AAGGATTTTG CTATAATAGC CACTTTTTTA AAA        33

( 2 ) INFORMATION FOR SEQ ID NO: 7:

( i ) SEQUENCE CHARACTERISTICS:
        ( A ) LENGTH: 34
        ( B ) TYPE: nucleic acid
        ( C ) STRANDEDNESS: single
        ( D ) TOPOLOGY: linear ( x i ) SEQUENCE DESCRIPTION: SEQ ID NO: 7:

TTTTAAAAAA GTGGCTTATT ATAGCAAAAT CCTT        34

( 2 ) INFORMATION FOR SEQ ID NO: 8:

( i ) SEQUENCE CHARACTERISTICS:
        ( A ) LENGTH: 32
        ( B ) TYPE: nucleic acid
        ( C ) STRANDEDNESS: single
        ( D ) TOPOLOGY: linear ( x i ) SEQUENCE DESCRIPTION: SEQ ID NO: 8:

ACTGACCTTT GGATGGCATC CGGAGTACTT CA        32

( 2 ) INFORMATION FOR SEQ ID NO: 9:

( i ) SEQUENCE CHARACTERISTICS:
        ( A ) LENGTH: 32
        ( B ) TYPE: nucleic acid
        ( C ) STRANDEDNESS: single
        ( D ) TOPOLOGY: linear ( x i ) SEQUENCE DESCRIPTION: SEQ ID NO: 9:

TGAAGTACTC CGGATGCCAT CCAAAGGTCA GT 32

( 2 ) INFORMATION FOR SEQ ID NO: 10:

( i ) SEQUENCE CHARACTERISTICS:
        ( A ) LENGTH: 28
        ( B ) TYPE: nucleic acid
        ( C ) STRANDEDNESS: single
        ( D ) TOPOLOGY: linear ( x i ) SEQUENCE DESCRIPTION: SEQ ID NO: 10:

AATGAATGGA CACTAGTAAT AAGAATTC 28

( 2 ) INFORMATION FOR SEQ ID NO: 11:

( i ) SEQUENCE CHARACTERISTICS:
        ( A ) LENGTH: 28
        ( B ) TYPE: nucleic acid
        ( C ) STRANDEDNESS: single
        ( D ) TOPOLOGY: linear ( x i ) SEQUENCE DESCRIPTION: SEQ ID NO: 11:

GAATTCTTAT TACTAGTGTC CATTCATT 28

( 2 ) INFORMATION FOR SEQ ID NO: 12:

( i ) SEQUENCE CHARACTERISTICS:
        ( A ) LENGTH: 32
        ( B ) TYPE: nucleic acid
        ( C ) STRANDEDNESS: single
        ( D ) TOPOLOGY: linear ( x i ) SEQUENCE DESCRIPTION: SEQ ID NO: 12:

GTAAGTAGTA CATGTAATGA GAGTGAAGGA GA 32

( 2 ) INFORMATION FOR SEQ ID NO: 13:

( i ) SEQUENCE CHARACTERISTICS:
        ( A ) LENGTH: 32
        ( B ) TYPE: nucleic acid
        ( C ) STRANDEDNESS: single
        ( D ) TOPOLOGY: linear ( x i ) SEQUENCE DESCRIPTION: SEQ ID NO: 13:

TCTCCTTCAC TCTCATTACA TGTACTACTT AC 32

( 2 ) INFORMATION FOR SEQ ID NO: 14:

( i ) SEQUENCE CHARACTERISTICS:
        ( A ) LENGTH: 46
        ( B ) TYPE: nucleic acid
        ( C ) STRANDEDNESS: single
        ( D ) TOPOLOGY: linear ( x i ) SEQUENCE DESCRIPTION: SEQ ID NO: 14:

TGGTGACCTT CGAAGGATCC CATATGTCTA GAGAATTCGG TCACCA 46

( 2 ) INFORMATION FOR SEQ ID NO: 15:

( i ) SEQUENCE CHARACTERISTICS:
        ( A ) LENGTH: 28
        ( B ) TYPE: nucleic acid
        ( C ) STRANDEDNESS: single
        ( D ) TOPOLOGY: linear ( x i ) SEQUENCE DESCRIPTION: SEQ ID NO: 15:

```
GGGGGTCGAC  TGATCACTAC  AGAACAAG                                                    2 8
```

( 2 ) INFORMATION FOR SEQ ID NO: 16:

( i ) SEQUENCE CHARACTERISTICS:
        ( A ) LENGTH: 23
        ( B ) TYPE: nucleic acid
        ( C ) STRANDEDNESS: single
        ( D ) TOPOLOGY: linear ( x i ) SEQUENCE DESCRIPTION: SEQ ID NO: 16:

```
GGGGGGGCAT  GCTTCTAGAG  GGC                                                         2 3
```

( 2 ) INFORMATION FOR SEQ ID NO: 17:

( i ) SEQUENCE CHARACTERISTICS:
        ( A ) LENGTH: 34
        ( B ) TYPE: nucleic acid
        ( C ) STRANDEDNESS: single
        ( D ) TOPOLOGY: linear ( x i ) SEQUENCE DESCRIPTION: SEQ ID NO: 17:

```
GCAAGCGAGG  ATCAAAATTT  TATGAGGCTA  TGCC                                            3 4
```

( 2 ) INFORMATION FOR SEQ ID NO: 18:

( i ) SEQUENCE CHARACTERISTICS:
        ( A ) LENGTH: 34
        ( B ) TYPE: nucleic acid
        ( C ) STRANDEDNESS: single
        ( D ) TOPOLOGY: linear ( x i ) SEQUENCE DESCRIPTION: SEQ ID NO: 18:

```
GGCATAGCCT  CATAAAATTT  TGATCCTCGC  TTGC                                            3 4
```

( 2 ) INFORMATION FOR SEQ ID NO: 19:

( i ) SEQUENCE CHARACTERISTICS:
        ( A ) LENGTH: 35
        ( B ) TYPE: nucleic acid
        ( C ) STRANDEDNESS: single
        ( D ) TOPOLOGY: linear ( x i ) SEQUENCE DESCRIPTION: SEQ ID NO: 19:

```
TAGCAAGCGA  GGATCAAATT  TATGCTAGTC  CTGGA                                           3 5
```

( 2 ) INFORMATION FOR SEQ ID NO: 20:

( i ) SEQUENCE CHARACTERISTICS:
        ( A ) LENGTH: 35
        ( B ) TYPE: nucleic acid
        ( C ) STRANDEDNESS: single
        ( D ) TOPOLOGY: linear ( x i ) SEQUENCE DESCRIPTION: SEQ ID NO: 20:

```
TCCAGGACTA  GCATAAATTT  GATCCTCGCT  TGCTA                                           3 5
```

( 2 ) INFORMATION FOR SEQ ID NO: 21:

( i ) SEQUENCE CHARACTERISTICS:
        ( A ) LENGTH: 31
        ( B ) TYPE: nucleic acid
        ( C ) STRANDEDNESS: single
        ( D ) TOPOLOGY: linear ( x i ) SEQUENCE DESCRIPTION: SEQ ID NO: 21:

```
GGGGGTCGAC  TTCGAATGGC  TAAACAGAAC  A                                               3 1
```

( 2 ) INFORMATION FOR SEQ ID NO: 22:

( i ) SEQUENCE CHARACTERISTICS:
        ( A ) LENGTH: 33
        ( B ) TYPE: nucleic acid
        ( C ) STRANDEDNESS: single
        ( D ) TOPOLOGY: linear ( x i ) SEQUENCE DESCRIPTION: SEQ ID NO: 22:

CATAGCCTCA TAAAATGACA TTTTACTGCA TAG        33

( 2 ) INFORMATION FOR SEQ ID NO: 23:

( i ) SEQUENCE CHARACTERISTICS:
        ( A ) LENGTH: 33
        ( B ) TYPE: nucleic acid
        ( C ) STRANDEDNESS: single
        ( D ) TOPOLOGY: linear ( x i ) SEQUENCE DESCRIPTION: SEQ ID NO: 23:

CTATGCAGTA AAATGTCATT TTATGAGGCT ATG        33

( 2 ) INFORMATION FOR SEQ ID NO: 24:

( i ) SEQUENCE CHARACTERISTICS:
        ( A ) LENGTH: 33
        ( B ) TYPE: nucleic acid
        ( C ) STRANDEDNESS: single
        ( D ) TOPOLOGY: linear ( x i ) SEQUENCE DESCRIPTION: SEQ ID NO: 24:

ATACTGGCAT GATGAATAGT AACATGGGGC AGG        33

( 2 ) INFORMATION FOR SEQ ID NO: 25:

( i ) SEQUENCE CHARACTERISTICS:
        ( A ) LENGTH: 33
        ( B ) TYPE: nucleic acid
        ( C ) STRANDEDNESS: single
        ( D ) TOPOLOGY: linear ( x i ) SEQUENCE DESCRIPTION: SEQ ID NO: 25:

CCTGCCCCAT GTTACTATTC ATCATGCCAG TAT        33

( 2 ) INFORMATION FOR SEQ ID NO: 26:

( i ) SEQUENCE CHARACTERISTICS:
        ( A ) LENGTH: 30
        ( B ) TYPE: nucleic acid
        ( C ) STRANDEDNESS: single
        ( D ) TOPOLOGY: linear ( x i ) SEQUENCE DESCRIPTION: SEQ ID NO: 26:

ATACTGGCAT GATGATTGAT CCTCGCTTGC        30

( 2 ) INFORMATION FOR SEQ ID NO: 27:

( i ) SEQUENCE CHARACTERISTICS:
        ( A ) LENGTH: 30
        ( B ) TYPE: nucleic acid
        ( C ) STRANDEDNESS: single
        ( D ) TOPOLOGY: linear ( x i ) SEQUENCE DESCRIPTION: SEQ ID NO: 27:

GCAAGCGAGG ATCAATCATC ATGCCAGTAT        30

( 2 ) INFORMATION FOR SEQ ID NO: 28:

( i ) SEQUENCE CHARACTERISTICS:
: ( A ) LENGTH: 28
: ( B ) TYPE: nucleic acid
: ( C ) STRANDEDNESS: single
: ( D ) TOPOLOGY: linear ( x i ) SEQUENCE DESCRIPTION: SEQ ID NO: 28:

CAGAGTCCTT GGATCCTTAT GGAAAACA 28

( 2 ) INFORMATION FOR SEQ ID NO: 29:

: ( i ) SEQUENCE CHARACTERISTICS:
:: ( A ) LENGTH: 67
:: ( B ) TYPE: nucleic acid
:: ( C ) STRANDEDNESS: double
:: ( D ) TOPOLOGY: linear : ( x i ) SEQUENCE DESCRIPTION: SEQ ID NO: 29:

GATGAGGATT AACACATGGA AAAGATTAGT AAAATGACCA ACTAATTCAT CTGCACTATT TTGATTG 67

( 2 ) INFORMATION FOR SEQ ID NO: 30:

: ( i ) SEQUENCE CHARACTERISTICS:
:: ( A ) LENGTH: 11
:: ( B ) TYPE: amino acid
:: ( C ) STRANDEDNESS:
:: ( D ) TOPOLOGY: linear : ( x i ) SEQUENCE DESCRIPTION: SEQ ID NO: 30:

Met Arg Ile Asn Thr Trp Lys Arg Leu Val Lys
 1               5                  10

( 2 ) INFORMATION FOR SEQ ID NO: 31:

: ( i ) SEQUENCE CHARACTERISTICS:
:: ( A ) LENGTH: 68
:: ( B ) TYPE: nucleic acid
:: ( C ) STRANDEDNESS: double
:: ( D ) TOPOLOGY: linear : ( x i ) SEQUENCE DESCRIPTION: SEQ ID NO: 31:

AAGGGCCACA GAGGGAGCCA TACAATGAAT GGACACTAGA GTAATAAGAA TTCGGTCACC 60
ATCCTCGC 68

( 2 ) INFORMATION FOR SEQ ID NO: 32:

: ( i ) SEQUENCE CHARACTERISTICS:
:: ( A ) LENGTH: 12
:: ( B ) TYPE: amino acid
:: ( C ) STRANDEDNESS:
:: ( D ) TOPOLOGY: linear : ( x i ) SEQUENCE DESCRIPTION: SEQ ID NO: 32:

Lys Gly His Arg Gly Ser His Thr Met Asn Gly His
 1               5                  10

( 2 ) INFORMATION FOR SEQ ID NO: 33:

: ( i ) SEQUENCE CHARACTERISTICS:
:: ( A ) LENGTH: 13
:: ( B ) TYPE: amino acid
:: ( C ) STRANDEDNESS:
:: ( D ) TOPOLOGY: linear : ( x i ) SEQUENCE DESCRIPTION: SEQ ID NO: 33:

Gly Pro Gln Arg Glu Pro Tyr Asn Glu Trp Thr Leu Glu
 1               5                   10

( 2 ) INFORMATION FOR SEQ ID NO: 34:

( i ) SEQUENCE CHARACTERISTICS:
        ( A ) LENGTH: 66
        ( B ) TYPE: nucleic acid
        ( C ) STRANDEDNESS: double
        ( D ) TOPOLOGY: linear ( x i ) SEQUENCE DESCRIPTION: SEQ ID NO: 34:

GATGAGGATT AACACATGGA AAAGATTAGT AAAATAATAA GAATTCGGTC ACCATCCTCG    60

CTCACT    66

( 2 ) INFORMATION FOR SEQ ID NO: 35:

( i ) SEQUENCE CHARACTERISTICS:
        ( A ) LENGTH: 65
        ( B ) TYPE: nucleic acid
        ( C ) STRANDEDNESS: double
        ( D ) TOPOLOGY: linear ( x i ) SEQUENCE DESCRIPTION: SEQ ID NO: 35:

TCTCTATCAA AGCAGTAAGT AGTACATGTA ATTTAATTGA TAGACTAATA GAAAGAGCAG    60

AAGAC    65

( 2 ) INFORMATION FOR SEQ ID NO: 36:

( i ) SEQUENCE CHARACTERISTICS:
        ( A ) LENGTH: 4
        ( B ) TYPE: amino acid
        ( C ) STRANDEDNESS:
        ( D ) TOPOLOGY: linear ( x i ) SEQUENCE DESCRIPTION: SEQ ID NO: 36:

Ser Leu Ser Lys
 1

( 2 ) INFORMATION FOR SEQ ID NO: 37:

( i ) SEQUENCE CHARACTERISTICS:
        ( A ) LENGTH: 4
        ( B ) TYPE: amino acid
        ( C ) STRANDEDNESS:
        ( D ) TOPOLOGY: linear ( x i ) SEQUENCE DESCRIPTION: SEQ ID NO: 37:

Leu Tyr Gln Ser
 1

( 2 ) INFORMATION FOR SEQ ID NO: 38:

( i ) SEQUENCE CHARACTERISTICS:
        ( A ) LENGTH: 66
        ( B ) TYPE: nucleic acid
        ( C ) STRANDEDNESS: double
        ( D ) TOPOLOGY: linear ( x i ) SEQUENCE DESCRIPTION: SEQ ID NO: 38:

GGCAAGTGGT CAAAAAGTAG TGTGATTGGA TGATAGCCAC TTTTTAAAAG AAAAGGGGGG    60

ACTGGA    66

( 2 ) INFORMATION FOR SEQ ID NO: 39:

( i ) SEQUENCE CHARACTERISTICS:

(A) LENGTH: 10
(B) TYPE: amino acid
(C) STRANDEDNESS:
(D) TOPOLOGY: linear (xi) SEQUENCE DESCRIPTION: SEQ ID NO: 39:

Gly Lys Trp Ser Lys Ser Ser Val Ile Gly
 1               5                   10

(2) INFORMATION FOR SEQ ID NO: 40:

(i) SEQUENCE CHARACTERISTICS:
    (A) LENGTH: 65
    (B) TYPE: nucleic acid
    (C) STRANDEDNESS: double
    (D) TOPOLOGY: linear (xi) SEQUENCE DESCRIPTION: SEQ ID NO: 40:

GCTAATTCAC TCCCAAAGAA GACAAGATAT CCCATCCGGA GTACTTCAAG AACTGCTGAC    60

ATCGA    65

(2) INFORMATION FOR SEQ ID NO: 41:

(i) SEQUENCE CHARACTERISTICS:
    (A) LENGTH: 45
    (B) TYPE: nucleic acid
    (C) STRANDEDNESS: double
    (D) TOPOLOGY: linear (xi) SEQUENCE DESCRIPTION: SEQ ID NO: 41:

GAGGTGGCAT AGCCTCATAA AATGACATTT TACTGCATAG CACTT    45

(2) INFORMATION FOR SEQ ID NO: 42:

(i) SEQUENCE CHARACTERISTICS:
    (A) LENGTH: 7
    (B) TYPE: amino acid
    (C) STRANDEDNESS:
    (D) TOPOLOGY: linear (xi) SEQUENCE DESCRIPTION: SEQ ID NO: 42:

Arg Trp His Ser Leu Ile Lys
 1               5

(2) INFORMATION FOR SEQ ID NO: 43:

(i) SEQUENCE CHARACTERISTICS:
    (A) LENGTH: 45
    (B) TYPE: nucleic acid
    (C) STRANDEDNESS: double
    (D) TOPOLOGY: linear (xi) SEQUENCE DESCRIPTION: SEQ ID NO: 43:

TTGGGAATAC TGGCATGATG AATAGTAACA TGGGGCAGGG GGATG    45

(2) INFORMATION FOR SEQ ID NO: 44:

(i) SEQUENCE CHARACTERISTICS:
    (A) LENGTH: 5
    (B) TYPE: amino acid
    (C) STRANDEDNESS:
    (D) TOPOLOGY: linear (xi) SEQUENCE DESCRIPTION: SEQ ID NO: 44:

Leu Gly Ile Leu Ala
 1               5

( 2 ) INFORMATION FOR SEQ ID NO: 45:

( i ) SEQUENCE CHARACTERISTICS:
        ( A ) LENGTH: 7
        ( B ) TYPE: amino acid
        ( C ) STRANDEDNESS:
        ( D ) TOPOLOGY: linear ( x i ) SEQUENCE DESCRIPTION: SEQ ID NO: 45:

Trp Glu Tyr Trp His Asp Glu
1               5

( 2 ) INFORMATION FOR SEQ ID NO: 46:

( i ) SEQUENCE CHARACTERISTICS:
        ( A ) LENGTH: 46
        ( B ) TYPE: nucleic acid
        ( C ) STRANDEDNESS: double
        ( D ) TOPOLOGY: linear ( x i ) SEQUENCE DESCRIPTION: SEQ ID NO: 46:

CCCCCTCCAG GACTAGCATA AATTTGATCC TCGCTTGCTA ACTGCA    46

( 2 ) INFORMATION FOR SEQ ID NO: 47:

( i ) SEQUENCE CHARACTERISTICS:
        ( A ) LENGTH: 6
        ( B ) TYPE: amino acid
        ( C ) STRANDEDNESS:
        ( D ) TOPOLOGY: linear ( x i ) SEQUENCE DESCRIPTION: SEQ ID NO: 47:

Pro Pro Pro Gly Leu Ala
1               5

( 2 ) INFORMATION FOR SEQ ID NO: 48:

( i ) SEQUENCE CHARACTERISTICS:
        ( A ) LENGTH: 47
        ( B ) TYPE: nucleic acid
        ( C ) STRANDEDNESS: double
        ( D ) TOPOLOGY: linear ( x i ) SEQUENCE DESCRIPTION: SEQ ID NO: 48:

GTCTTGGGAA TACTGGCATG ATGATTGATC CTCGCTTGCT AACTGCA    47

( 2 ) INFORMATION FOR SEQ ID NO: 49:

( i ) SEQUENCE CHARACTERISTICS:
        ( A ) LENGTH: 6
        ( B ) TYPE: amino acid
        ( C ) STRANDEDNESS:
        ( D ) TOPOLOGY: linear ( x i ) SEQUENCE DESCRIPTION: SEQ ID NO: 49:

Val Leu Gly Ile Leu Ala
1               5

( 2 ) INFORMATION FOR SEQ ID NO: 50:

( i ) SEQUENCE CHARACTERISTICS:
        ( A ) LENGTH: 8
        ( B ) TYPE: amino acid
        ( C ) STRANDEDNESS:
        ( D ) TOPOLOGY: linear ( x i ) SEQUENCE DESCRIPTION: SEQ ID NO: 50:

Ser Trp Glu Tyr Trp His Asp Asp
1               5

( 2 ) INFORMATION FOR SEQ ID NO: 51:

( i ) SEQUENCE CHARACTERISTICS:
        ( A ) LENGTH: 45
        ( B ) TYPE: nucleic acid
        ( C ) STRANDEDNESS: double
        ( D ) TOPOLOGY: linear ( x i ) SEQUENCE DESCRIPTION: SEQ ID NO: 51:

GAGGTGGCAT AGCCTCATAA AATTTTGATC CTCGCTTGCT AACTG      45

( 2 ) INFORMATION FOR SEQ ID NO: 52:

( i ) SEQUENCE CHARACTERISTICS:
        ( A ) LENGTH: 8
        ( B ) TYPE: amino acid
        ( C ) STRANDEDNESS:
        ( D ) TOPOLOGY: linear ( x i ) SEQUENCE DESCRIPTION: SEQ ID NO: 52:

Arg Trp His Ser Leu Ile Lys Phe
 1                 5

( 2 ) INFORMATION FOR SEQ ID NO: 53:

( i ) SEQUENCE CHARACTERISTICS:
        ( A ) LENGTH: 41
        ( B ) TYPE: nucleic acid
        ( C ) STRANDEDNESS: double
        ( D ) TOPOLOGY: linear ( x i ) SEQUENCE DESCRIPTION: SEQ ID NO: 53:

GCTCACTCTC TTGTGAGGGA CAGTCTCATT TTATAAAGA A      41

( 2 ) INFORMATION FOR SEQ ID NO: 54:

( i ) SEQUENCE CHARACTERISTICS:
        ( A ) LENGTH: 4
        ( B ) TYPE: amino acid
        ( C ) STRANDEDNESS:
        ( D ) TOPOLOGY: linear ( x i ) SEQUENCE DESCRIPTION: SEQ ID NO: 54:

Leu Thr Leu Leu
 1

( 2 ) INFORMATION FOR SEQ ID NO: 55:

( i ) SEQUENCE CHARACTERISTICS:
        ( A ) LENGTH: 13
        ( B ) TYPE: amino acid
        ( C ) STRANDEDNESS:
        ( D ) TOPOLOGY: linear ( x i ) SEQUENCE DESCRIPTION: SEQ ID NO: 55:

Ser Leu Ser Cys Glu Gly Gln Ser His Phe Ile Lys Glu
 1             5                       10

( 2 ) INFORMATION FOR SEQ ID NO: 56:

( i ) SEQUENCE CHARACTERISTICS:
        ( A ) LENGTH: 42
        ( B ) TYPE: nucleic acid
        ( C ) STRANDEDNESS: double
        ( D ) TOPOLOGY: linear ( x i ) SEQUENCE DESCRIPTION: SEQ ID NO: 56:

-continued

```
GGAGGATGAG GAGCATTATT TAACCTTCTT AACATGGCTG AC                                42
```

( 2 ) INFORMATION FOR SEQ ID NO: 57:

( i ) SEQUENCE CHARACTERISTICS:
        ( A ) LENGTH: 13
        ( B ) TYPE: amino acid
        ( C ) STRANDEDNESS:
        ( D ) TOPOLOGY: linear ( x i ) SEQUENCE DESCRIPTION: SEQ ID NO: 57:

```
Glu Asp Glu Glu His Tyr Leu Thr Phe Leu Thr Trp Leu
 1               5                  10
```